US009932311B2

(12) United States Patent
Biftu et al.

(10) Patent No.: US 9,932,311 B2
(45) Date of Patent: *Apr. 3, 2018

(54) ANTIDIABETIC TRICYCLIC COMPOUNDS

(71) Applicant: Merck Sharp & Dohme Corp., Rahway, NJ (US)

(72) Inventors: Tesfaye Biftu, Freehold, NJ (US); Purakkattle Biju, Westwood, MA (US); Steven L. Colletti, Princeton, NJ (US); Mingxiang Cui, Shanghai (CN); William K. Hagmann, Westfield, NJ (US); Bin Hu, Shanghai (CN); Hubert Josien, Jersey City, NJ (US); Nam Fung Kar, Brooklyn, NY (US); Anilkumar Nair, Edison, NJ (US); Ravi Nargund, East Brunswick, NJ (US); Donald M. Sperbeck, East Hanover, NJ (US); Cheng Zhu, Edison, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/023,124

(22) PCT Filed: Sep. 30, 2014

(86) PCT No.: PCT/CN2014/087857
§ 371 (c)(1),
(2) Date: Mar. 18, 2016

(87) PCT Pub. No.: WO2015/051725
PCT Pub. Date: Apr. 16, 2015

(65) Prior Publication Data
US 2016/0207887 A1    Jul. 21, 2016

(30) Foreign Application Priority Data

Oct. 8, 2013 (WO) ............... PCT/CN2013/084846

(51) Int. Cl.
| | | |
|---|---|---|
| C07D 221/16 | (2006.01) |
| C07D 401/12 | (2006.01) |
| C07D 405/12 | (2006.01) |
| C07D 405/14 | (2006.01) |
| A61K 31/435 | (2006.01) |
| A61K 31/444 | (2006.01) |
| A61K 45/06 | (2006.01) |

(52) U.S. Cl.
CPC .......... C07D 221/16 (2013.01); A61K 31/435 (2013.01); A61K 31/444 (2013.01); A61K 45/06 (2013.01); C07D 401/12 (2013.01); C07D 405/12 (2013.01)

(58) Field of Classification Search
None
See application file for complete search history.

(56) References Cited

U.S. PATENT DOCUMENTS

| | | |
|---|---|---|
| 6,312,662 B1 | 11/2001 | Erion et al. |
| 6,489,476 B1 | 12/2002 | Dang et al. |
| 2005/0148643 A1 | 7/2005 | Rui et al. |
| 2006/0258722 A1 | 11/2006 | Yasuma et al. |
| 2007/0213364 A1 | 9/2007 | Yasuma et al. |
| 2012/0004187 A1 | 1/2012 | Keil et al. |

FOREIGN PATENT DOCUMENTS

| | | |
|---|---|---|
| EP | 0120403 A2 | 10/1984 |
| WO | WO9307124 A1 | 4/1993 |
| WO | WO1995029897 A1 | 11/1995 |
| WO | WO1998039342 A1 | 9/1998 |
| WO | WO1998039343 A1 | 9/1998 |
| WO | WO2000003997 A1 | 1/2000 |
| WO | WO2000014095 A1 | 3/2000 |

(Continued)

OTHER PUBLICATIONS

Tomita et al. Frontiers in Endocrinology, vol. 5, pp. 1-3 Sep. 2014.*
Mancini et al. Trends in Endocrinology and Metabolism, vol. 24, No. 8 pp. 398-407, 2013.*
Briscoe, C. P. et al., The Orphan G Protein-coupled Receptor GPR40 Is Activated by Medium and Long Chain Fatty Acids, The Journal of Biological Chemistry, 2003, 11303-11311, No. 13, 278.
Itoh, Y. et al., Free fatty acids regulate insulin secretion from pancreatic B cells through GPR40, Nature, 2003, 173-176, 422.
Kotarsky, K. et al., A human cell surface receptor activated by free fatty acids and thiazolidinedione drugs, Biochemical and Biophysical Research Communications, 2003, 406-410, 301.

*Primary Examiner* — Emily Bernhardt
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

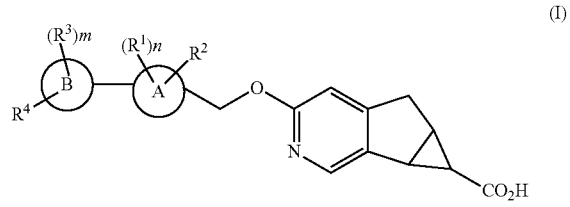

24 Claims, No Drawings

(56) References Cited

FOREIGN PATENT DOCUMENTS

| | | |
|---|---|---|
| WO | WO2001053272 A1 | 7/2001 |
| WO | WO2001053291 A1 | 7/2001 |
| WO | WO2002040019 A1 | 5/2002 |
| WO | WO2002092575 A1 | 11/2002 |
| WO | WO2003018061 A1 | 3/2003 |
| WO | WO2004022551 A1 | 3/2004 |
| WO | WO2004041266 A1 | 5/2004 |
| WO | WO2005002520 A2 | 1/2005 |
| WO | WO2005018672 A1 | 3/2005 |
| WO | WO2005051373 A1 | 6/2005 |
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006094209 A2 | 9/2006 |
| WO | WO2006127503 A2 | 11/2006 |
| WO | WO2007013689 A1 | 2/2007 |
| WO | WO2007033002 A1 | 3/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO2009111056 A1 | 9/2009 |
| WO | WO2010036613 A1 | 4/2010 |
| WO | WO2010045258 A2 | 4/2010 |
| WO | WO2010047982 A1 | 4/2010 |
| WO | WO2010051176 A1 | 5/2010 |
| WO | WO2010051206 A1 | 5/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2014019186 A1 | 2/2014 |
| WO | WO2014022528 A1 | 2/2014 |
| WO | 2015/073342 A1 * | 5/2015 |

* cited by examiner

US 9,932,311 B2

ANTIDIABETIC TRICYCLIC COMPOUNDS

CROSS-REFERENCE TO RELATED APPLICATIONS

This application is a U.S. National Phase application under 35 U.S.C. § 371 of PCT Application PCT/CN14/087857, filed Sep. 30, 2014, which claims priority from and the benefit of PCT Application PCT/CN13/084846; filed Oct. 8, 2013.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body. Patients having Type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglitide); and (5) inhibitors of incretin hormone degradation (DPP-4 inhibitors, such as sitagliptin, alogliptin, vildagliptin, linagliptin, denagliptin, and saxagliptin).

The biguanides are a class of drugs that are widely used to treat Type 2 diabetes. The two best known biguanides, phenformin and metformin, cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or an insulin secretagogue, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of Type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of Type 2 diabetes, resulting in partial or complete correction of elevated plasma glucose levels without the occurrence of hypoglycemia. PPAR-gamma agonism is believed to be responsible for the improved insulin sensititization that is observed in human patients who are treated with the glitazones. New PPAR agonists are currently being developed. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) have been made and tested, but so far none have been approved by the regulatory authorities. The currently marketed PPAR gamma agonists are modestly effective in reducing plasma glucose and HemoglobinA1C. The currently marketed compounds do not greatly improve lipid metabolism and may actually have a negative effect on the lipid profile. Selective PPAR Gamma Partial Agonists (SPPARM's) are currently being developed and may be equally effective, with fewer side effects, such as weight gain and edema. Thus, the PPAR compounds represent an important advance in diabetic therapy.

Another widely used drug treatment involves the administration of insulin secretagogues, such as the sulfonylureas (e.g. tolbutamide, glipizide, and glimepiride). These drugs increase the plasma level of insulin by stimulating the pancreatic β-cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules; whereas other extracellular signals act as potentiators or inhibitors of insulin secretion through GPCR's present on the plasma membrane. Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

Dipeptidyl peptidase IV (DPP-4) inhibitors (e.g., sitagliptin, vildagliptin, alogliptin, linagliptin, denagliptin, and saxagliptin) provide a new route for increasing insulin secretion in response to food consumption. DPP-4 is a cell surface protein with broad tissue distribution that has been implicated in a wide range of biological functions. DPP-4 is identical to the T-cell activation marker CD26 and can cleave a number of immunoregulatory, endocrine, and neurological peptides in vitro. It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Studies with DPP-4(−/−)-deficient mice and clinical trials with DPP-4 inhibitors indicate that DPP-4 inhibition increases the steady state concentrations of GLP-1 and GIP, resulting in improved glucose tolerance. Inactivation of these peptides by DPP-4 may also play a role in glucose homeostasis. DPP-4 inhibitors therefore have utility in the treatment of Type 2 diabetes and in the treatment and prevention of the numerous conditions that often accompany Type 2 diabetes, including Metabolic Syndrome, reactive hypoglycemia, and diabetic dyslipidemia. GLP-1 has other effects that help to lower blood glucose and contribute to glucose homeostasis. GLP-1 inhibits glucagon secretion from the liver. Glucagon is a hormone that increases blood glucose levels by stimulating glucose production from glycogen stores in the liver. GLP-1 also delays stomach emptying, which helps to spread glucose absorption out over time, and thus limit hyperglycemia. Also, studies in animals have shown that GLP-1 can increase the number of beta cells, either through promoting growth or by inhibiting apoptosis. Thus, potentiation of GLP-1 action by preventing its degradation offers several mechanisms to attenuate hyperglycemia associated with Type 2 diabetes.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion.

There are several potential advantages of GPR40 as a potential target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent GPR40 agonists that have pharmacokinetic and pharmacodynamic properties suitable for use as human pharmaceuticals.

Benzimidazole compounds are disclosed in WO 2010/051206; WO 2010/051176; WO 2010/047982; WO 2010/036613; WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. No. 6,312,662; U.S. Pat. No. 6,489,476; US 2005/0148643; DE 3 316 095; JP 6 298 731; EP 0 126 030; EP 0 128 862; EP 0 129 506; and EP 0 120 403.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/

091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030618, WO 2008/054674, WO 2008/054675, WO 2008/066097, WO 2008/130514, WO 2009/048527, WO 2009/111056, WO 2010/045258, WO 2010/085522, WO 2010/085525, WO 2010/085528, WO 2010/091176, WO 2010/143733 and WO 2012/0004187.

SUMMARY OF THE INVENTION

The present invention relates to novel substituted compounds of structural formula I:

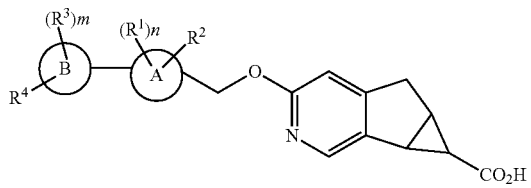

I and pharmaceutically acceptable salts thereof. The compounds of structural formula I, and embodiments thereof, are agonists of G-protein-coupled receptor 40 (GPR40) and may be useful in the treatment, prevention and suppression of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

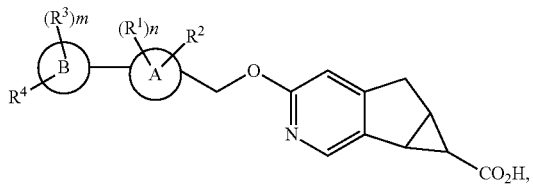

I or a pharmaceutically acceptable salt thereof; wherein
A is phenyl;
B is selected from the group consisting of:
  (1) phenyl, and
  (2) pyridyl;
$R^1$ is selected from the group consisting of:
  (1) halogen,
  (2) —CN,
  (3) —$C_{1-6}$alkyl,
  (4) —$(CH_2)_r$—$OC_{1-6}$alkyl,
  (5) —$(CH_2)_r$—$C_{3-6}$cycloalkyl, and
  (6) —$(CH_2)_r$—O—$(CH_2)_t$—$C_{3-6}$cycloalkyl,
wherein each $CH_2$, —$C_{1-6}$alkyl, —$OC_{1-6}$alkyl and —$C_{3-6}$cycloalkyl is unsubstituted or substituted with one to four substituents selected from halogen, —$C_{1-6}$alkyl and —$(CH_2)_v$—$C_{3-6}$cycloalkyl;
$R^2$ is halogen;
$R^3$ when present is selected from the group consisting of:
  (1) halogen,
  (2) —$C_{1-6}$alkyl, and
  (3) —$(CH_2)_u$—$C_{3-6}$cycloalkyl,
wherein each $C_{1-6}$alkyl and $C_{3-6}$cycloalkyl is unsubstituted or substituted with one to three substituents selected from halogen;
$R^4$ is selected from:
  (1) —$OC_{1-6}$alkyl, and
  (2) —$C_{1-6}$alkyl,
wherein —$C_{1-6}$alkyl is unsubstituted or substituted with one, two, three or four substituents selected from $R^5$;
$R^5$ is selected from the group consisting of:
  (1) —$(CH_2)_s$halogen,
  (2) —$C_{1-6}$alkyl,
  (3) —$(CH_2)_s$—O—$C_{1-6}$alkyl,
  (4) —$(CH_2)_s$OH,
  (5) —$(CH_2)_s SO_2 C_{1-6}$alkyl,
  (6) —$(CH_2)_s SO_2$—$(CH_2)_t$—$C_{3-6}$cycloalkyl,
  (7) —$(CH_2)_s C_{3-6}$cycloalkyl,
  (8) —$(CH_2)_s$—O—$(CH_2)_t$—$C_{3-6}$cycloalkyl, and

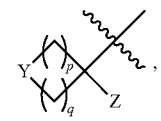

(9)

wherein each $CH_2$, $C_{1-6}$alkyl and $C_{3-6}$cycloalkyl is unsubstituted or substituted with one to three substituents selected from halogen and $(CH_2)_w OH$;
Y is selected from:
  (1) —CH(OH)—,
  (2) —C($C_{1-6}$alkyl)(OH)—,
  (3) —C[$(CH_2)_t$—$C_{3-6}$cycloalkyl](OH)—,
  (4) O,
  (5) S, and
  (6) $SO_2$, wherein each $CH_2$, $C_{1-6}$alkyl and $C_{3-6}$cycloalkyl is unsubstituted or substituted with one to three substituents selected from halogen and $(CH_2)_w OH$;

Z is selected from:
(1) hydrogen,
(2) —$C_{1-6}$alkyl,
(3) —$(CH_2)_s$—O—$C_{1-6}$alkyl,
(4) —$(CH_2)_s$—OH,
(5) —$(CH_2)_s SO_2 C_{1-6}$alkyl,
(6) —$(CH_2)_s SO_2$—$(CH_2)_t$—$C_{3-6}$cycloalkyl,
(7) —$(CH_2)_s C_{3-6}$cycloalkyl, and
(8) —$(CH_2)_s$—O—$(CH_2)_t$—$C_{3-6}$cycloalkyl, wherein each $CH_2$, $C_{1-6}$alkyl and $C_{3-6}$cycloalkyl is unsubstituted or substituted with one to three substituents selected from halogen;

m is 0, 1, 2 or 3;
n is 1 or 2;
p is 0, 1, 2 or 3;
q is 0, 1, 2 or 3, provided that p+q is at least 2;
r is 0, 1, 2 or 3;
s is 0, 1, 2 or 3;
t is 0, 1, 2 or 3;
u is 0, 1, 2 or 3;
v is 0, 1, 2 or 3; and
w is 0, 1, 2 or 3.

In another embodiment, the present invention is concerned with novel compounds of structural Formula I:

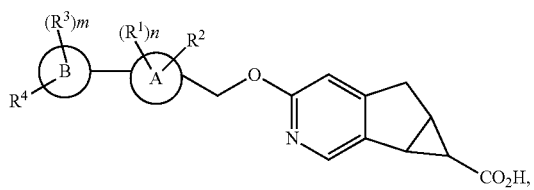

I or a pharmaceutically acceptable salt thereof; wherein
A is phenyl;
B is selected from the group consisting of:
(1) phenyl, and
(2) pyridyl;
$R^1$ is selected from the group consisting of:
(1) halogen,
(2) —CN,
(3) —$C_{1-6}$alkyl,
(4) —$(CH_2)_r$—$OC_{1-6}$alkyl,
(5) —$(CH_2)_r$—$C_{3-6}$cycloalkyl, and
(6) —$(CH_2)_r$—O—$(CH_2)_v$—$C_{3-6}$cycloalkyl, wherein each $CH_2$, —$C_{1-6}$alkyl, —$OC_{1-6}$alkyl and —$C_{3-6}$cycloalkyl is unsubstituted or substituted with one to four substituents selected from halogen, —$C_{1-6}$alkyl and —$(CH_2)$—$C_{3-6}$cycloalkyl;

$R^2$ is halogen;
$R^3$ when present is selected from the group consisting of:
(1) halogen,
(2) —$C_{1-6}$alkyl, and
(3) —$(CH_2)_u$—$C_{3-6}$cycloalkyl, wherein each $C_{1-6}$alkyl and $C_{3-6}$cycloalkyl is unsubstituted or substituted with one to three substituents selected from halogen;

$R^4$ is —$OC_{1-6}$alkyl, wherein —$C_{1-6}$alkyl is unsubstituted or substituted with one, two, three or four substituents selected from $R^5$;

$R^5$ is selected from the group consisting of:
(1) —$(CH_2)_s$halogen,
(2) —$C_{1-6}$alkyl,
(3) —$(CH_2)_s$—O—$C_{1-6}$alkyl,
(4) —$(CH_2)_s$ OH,
(5) —$(CH_2)_s SO_2 C_{1-6}$alkyl,
(6) —$(CH_2)_s SO_2$—$(CH_2)_t$—$C_{3-6}$cycloalkyl,
(7) —$(CH_2)_s C_{3-6}$cycloalkyl,
(8) —$(CH_2)_s$—O—$(CH_2)_t$—$C_{3-6}$cycloalkyl, and

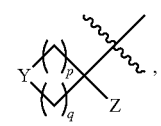

(9)

wherein each $CH_2$, $C_{1-6}$alkyl and $C_{3-6}$cycloalkyl is unsubstituted or substituted with one to three substituents selected from halogen and —$(CH_2)_w OH$;

Y is selected from:
(1) —CH(OH)—,
(2) —C($C_{1-6}$alkyl)(OH)—,
(3) —C[$(CH_2)_t$—$C_{3-6}$cycloalkyl](OH)—,
(4) O,
(5) S, and
(6) $SO_2$, wherein each $CH_2$, $C_{1-6}$alkyl and $C_{3-6}$cycloalkyl is unsubstituted or substituted with one to three substituents selected from halogen and $(CH_2)_w OH$;

Z is selected from:
(1) hydrogen,
(2) —$C_{1-6}$alkyl,
(3) —$(CH_2)_s$—O—$C_{1-6}$alkyl,
(4) —$(CH_2)_s$—OH,
(5) —$(CH_2)_s SO_2 C_{1-6}$alkyl,
(6) —$(CH_2)_s SO_2$—$(CH_2)_t$—$C_{3-6}$cycloalkyl,
(7) —$(CH_2)_s C_{3-6}$cycloalkyl, and
(8) —$(CH_2)_s$—O—$(CH_2)_t$—$C_{3-6}$cycloalkyl, wherein each $CH_2$, $C_{1-6}$alkyl and $C_{3-6}$cycloalkyl is unsubstituted or substituted with one to three substituents selected from halogen;

m is 0, 1, 2 or 3;
n is 1 or 2;
p is 0, 1, 2 or 3;
q is 0, 1, 2 or 3, provided that p+q is at least 2;
r is 0, 1, 2 or 3;
s is 0, 1, 2 or 3;
t is 0, 1, 2 or 3;
u is 0, 1, 2 or 3;
v is 0, 1, 2 or 3; and
w is 0, 1, 2 or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment of the present invention, A is phenyl. In a class of this embodiment, A is phenyl, wherein phenyl is substituted with one or two substituents selected from $R^1$, and wherein phenyl is substituted with one substituent selected from $R^2$. In another class of this embodiment, A is phenyl, wherein phenyl is substituted with two substituents selected from $R^1$, and wherein phenyl is substituted with one substituent selected from $R^2$.

In another class of this embodiment, A is phenyl, wherein phenyl is substituted with one substituent selected from $R^1$, and wherein phenyl is substituted with one substituent selected from $R^2$.

In another embodiment of the present invention, A is

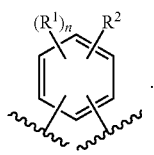

In another embodiment of the present invention, A is

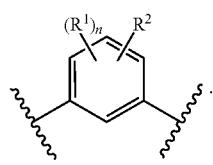

In another embodiment of the present invention, A is

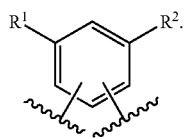

In another embodiment of the present invention, A is

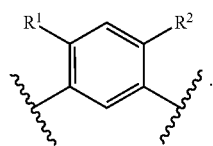

In another embodiment of the present invention, B is selected from the group consisting of: phenyl and pyridyl. In another embodiment of the present invention, B is selected from phenyl and pyridyl, wherein phenyl and pyridyl are substituted with $R^4$, and are unsubstituted or substituted with one, two or three substituents selected from $R^3$. In a class of this embodiment of the present invention, B is selected from phenyl and pyridyl, wherein phenyl and pyridyl are substituted with $R^4$, and are unsubstituted or substituted with one or two substituents selected from $R^3$. In another class of this embodiment of the present invention, B is selected from phenyl and pyridyl, wherein phenyl and pyridyl are substituted with $R^4$, and are unsubstituted or substituted with one substituent selected from $R^3$. In another class of this embodiment of the present invention, B is selected from phenyl and pyridyl.

In another embodiment of the present invention, B is pyridyl, wherein pyridyl is substituted with $R^4$, and is unsubstituted or substituted with one, two or three substituents selected from $R^3$. In a class of this embodiment of the present invention, B is pyridyl, wherein pyridyl is substituted with $R^4$, and is unsubstituted or substituted with one or two substituents selected from $R^3$. In another class of this embodiment of the present invention, B is pyridyl, wherein pyridyl is substituted with $R^4$, and is unsubstituted or substituted with one substituent selected from $R^3$. In another class of this embodiment of the present invention, B is pyridyl.

In another embodiment of the present invention, B is phenyl, wherein phenyl is substituted with $R^4$, and is unsubstituted or substituted with one, two or three substituents selected from $R^3$. In a class of this embodiment of the present invention, B is phenyl, wherein phenyl is substituted with $R^4$, and is unsubstituted or substituted with one or two substituents selected from $R^3$. In another class of this embodiment of the present invention, B is phenyl, wherein phenyl is substituted with $R^4$, and is unsubstituted or substituted with one substituent selected from $R^3$. In another class of this embodiment of the present invention, B is phenyl.

In another embodiment of the present invention, $R^1$ is selected from the group consisting of: halogen, —CN, —$C_{1-6}$alkyl, —$(CH_2)_r$—$OC_{1-6}$alkyl, —$(CH_2)_r$—$C_{3-6}$cycloalkyl, and —$(CH_2)_r$—O—$(CH_2)$—$C_{3-6}$cycloalkyl, wherein each $CH_2$, —$C_{1-6}$alkyl, —$OC_{1-6}$alkyl and —$C_{3-6}$cycloalkyl is unsubstituted or substituted with one to four substituents selected from halogen, —$C_{1-6}$alkyl and —$(CH_2)_v$—$C_{3-6}$cycloalkyl. In a class of this embodiment, each —$C_{1-6}$alkyl, —$OC_{1-6}$alkyl and —$C_{3-6}$cycloalkyl is unsubstituted or substituted with one to four substituents selected from Cl and F. In another class of this embodiment, each —$C_{1-6}$alkyl, —$OC_{1-6}$alkyl and —$C_{3-6}$cycloalkyl is unsubstituted or substituted with one to four substituents selected from Cl. In another class of this embodiment, each —$C_{1-6}$alkyl, —$OC_{1-6}$alkyl and —$C_{3-6}$cycloalkyl is unsubstituted or substituted with one to four substituents selected from F.

In another embodiment of the present invention, $R^1$ is selected from the group consisting of: halogen, —CN, —$C_{1-6}$alkyl, —$(CH_2)_r$—$OC_{1-6}$alkyl, —$(CH_2)_r$—$C_{3-6}$cycloalkyl, and —$(CH_2)_r$—O—$(CH_2)$—$C_{3-6}$cycloalkyl, wherein each $CH_2$, —$C_{1-6}$alkyl, —$OC_{1-6}$alkyl and —$C_{3-6}$cycloalkyl is unsubstituted or substituted with one to four substituents selected from halogen. In a class of this embodiment, each —$C_{1-6}$alkyl, —$OC_{1-6}$alkyl and —$C_{3-6}$cycloalkyl is unsubstituted or substituted with one to four substituents selected from Cl and F. In another class of this embodiment, each —$C_{1-6}$alkyl, —$OC_{1-6}$alkyl and —$C_{3-6}$cycloalkyl is unsubstituted or substituted with one to four substituents selected from Cl. In another class of this embodiment, each —$C_{1-6}$alkyl, —$OC_{1-6}$alkyl and —$C_{3-6}$cycloalkyl is unsubstituted or substituted with one to four substituents selected from F.

In another embodiment of the present invention, $R^1$ is selected from the group consisting of: halogen, —CN, —$C_{1-6}$alkyl, —$OC_{1-6}$alkyl and —$C_{3-6}$cycloalkyl, wherein each —$C_{1-6}$alkyl, —$OC_{1-6}$alkyl and —$C_{3-6}$cycloalkyl is unsubstituted or substituted with one to four substituents selected from halogen. In a class of this embodiment, each —$C_{1-6}$alkyl, —$OC_{1-6}$alkyl and —$C_{3-6}$cycloalkyl is unsubstituted or substituted with one to four substituents selected from Cl and F. In another class of this embodiment, each —$C_{1-6}$alkyl, —$OC_{1-6}$alkyl and —$C_{3-6}$cycloalkyl is unsubstituted or substituted with one to four substituents selected from Cl. In another class of this embodiment, each —$C_{1-6}$alkyl, —$OC_{1-6}$alkyl and —$C_{3-6}$cycloalkyl is unsubstituted or substituted with one to four substituents selected from F.

In another embodiment of the present invention, $R^1$ is selected from the group consisting of: halogen and —$C_{1-6}$alkyl, wherein —$C_{1-6}$alkyl is unsubstituted or substituted with one to four substituents selected from halogen. In a class of this embodiment, —$C_{1-6}$alkyl is unsubstituted or substituted with one to four substituents selected from Cl and F. In another class of this embodiment, —$C_{1-6}$alkyl is unsubstituted or substituted with one to four substituents selected from Cl. In another class of this embodiment, —$C_{1-6}$alkyl is unsubstituted or substituted with one to four substituents selected from F.

In another embodiment of the present invention, $R^1$ is selected from the group consisting of: halogen and —$C_{1-6}$alkyl, wherein each —$C_{1-6}$alkyl is unsubstituted or substituted with one, two or three substituents selected from halogen. In a class of this embodiment, each —$C_{1-6}$alkyl is unsubstituted or substituted with one, two or three substituents selected from Cl and F. In another class of this embodiment, each —$C_{1-6}$alkyl is unsubstituted or substituted with one, two or three substituents selected from Cl. In another class of this embodiment, each —$C_{1-6}$alkyl is unsubstituted or substituted with one, two or three substituents selected from F. In another class of this embodiment, each —$C_{1-6}$alkyl is substituted with one, two or three substituents selected from Cl and F. In another class of this embodiment, each —$C_{1-6}$alkyl is substituted with one, two or three substituents selected from Cl. In another class of this embodiment, each —$C_{1-6}$alkyl is substituted with one, two or three substituents selected from F.

In another embodiment of the present invention, $R^1$ is selected from the group consisting of: F, Cl, $CF_3$, and $CHF_2$. In another embodiment of the present invention, $R^1$ is selected from the group consisting of: F and $CF_3$. In another embodiment of the present invention, $R^1$ is halogen. In a class of this embodiment, $R^1$ is selected from F and Cl. In another class of this embodiment, $R^1$ is Cl. In another class of this embodiment, $R^1$ is F.

In another embodiment of the present invention, $R^1$ is —$C_{1-6}$alkyl, wherein each —$C_{1-6}$alkyl is substituted with one, two or three substituents selected from halogen. In a class of this embodiment, $R^1$ is —$C_{1-6}$alkyl, wherein —$C_{1-6}$alkyl is unsubstituted or substituted with one, two or three substituents selected from Cl and F. In another class of this embodiment, $R^1$ is —$C_{1-6}$alkyl, wherein —$C_{1-6}$alkyl is unsubstituted or substituted with one, two or three substituents selected from Cl. In another class of this embodiment, $R^1$ is —$C_{1-6}$alkyl, wherein —$C_{1-6}$alkyl is unsubstituted or substituted with one, two or three substituents selected from F.

In another class of this embodiment, $R^1$ is —$C_{1-6}$alkyl, wherein —$C_{1-6}$alkyl is substituted with one, two or three substituents selected from Cl and F. In another class of this embodiment, $R^1$ is —$C_{1-6}$alkyl, wherein —$C_{1-6}$alkyl is substituted with one, two or three substituents selected from Cl. In another class of this embodiment, $R^1$ is —$C_{1-6}$alkyl, wherein —$C_{1-6}$alkyl is substituted with one, two or three substituents selected from F.

In another embodiment of the present invention, $R^1$ is —$CF_3$ or —$CHF_2$. In another embodiment of the present invention, $R^1$ is —$CF_3$. In another embodiment of the present invention, $R^1$ is —$CHF_2$.

In another embodiment of the present invention, $R^2$ is halogen. In another embodiment of the present invention, $R^2$ is selected from: Br, I, F and Cl. In another embodiment of the present invention, $R^2$ is selected from F and Cl. In another embodiment of the present invention, $R^2$ is F. In another embodiment of the present invention, $R^2$ is Cl.

In another embodiment of the present invention, $R^3$ when present is selected from the group consisting of: halogen, and —$C_{1-6}$alkyl, wherein each $C_{1-6}$alkyl is unsubstituted or substituted with one to three substituents selected from halogen. In another embodiment of the present invention, $R^3$ when present is selected from the group consisting of: halogen, and —$C_{1-6}$alkyl. In another embodiment of the present invention, $R^3$ when present is selected from the group consisting of: F, Cl, $CH_3$, and $CHF_2$. In another embodiment of the present invention, $R^3$ when present is selected from the group consisting of: F and $CH_3$.

In another embodiment of the present invention, $R^3$ when present is selected from the group consisting of: halogen, —$C_{1-6}$alkyl and —$(CH_2)_u$—$C_{3-6}$cycloalkyl, wherein each $C_{1-6}$alkyl and $C_{3-6}$cycloalkyl is unsubstituted or substituted with one to three substituents selected from halogen. In another embodiment of the present invention, $R^3$ when present is selected from the group consisting of: halogen, —$C_{1-6}$alkyl, and —$C_{3-6}$cycloalkyl, wherein each $C_{1-6}$alkyl and $C_{3-6}$cycloalkyl is unsubstituted or substituted with one to three substituents selected from halogen. In a class of this embodiment, each $C_{1-6}$alkyl is unsubstituted or substituted with one to three substituents selected from Cl and F. In another class of this embodiment, each $C_{1-6}$alkyl is unsubstituted or substituted with one to three substituents selected from Cl. In another class of this embodiment, each $C_{1-6}$alkyl is unsubstituted or substituted with one to three substituents selected from F.

In another embodiment of the present invention, $R^3$ when present is selected from the group consisting of: halogen, and —$C_{1-6}$alkyl, wherein each $C_{1-6}$alkyl is unsubstituted or substituted with one to three substituents selected from halogen. In a class of this embodiment, each $C_{1-6}$alkyl is unsubstituted or substituted with one to three substituents selected from Cl and F. In another class of this embodiment, each $C_{1-6}$alkyl is unsubstituted or substituted with one to three substituents selected from Cl. In another class of this embodiment, each $C_{1-6}$alkyl is unsubstituted or substituted with one to three substituents selected from F.

In another embodiment of the present invention, $R^3$ when present is selected from the group consisting of: F, —$CF_3$, —$CHF_2$, and —$CH_3$. In another embodiment of the present invention, $R^3$ is selected from the group consisting of: F, —$CF_3$, —$CHF_2$, and —$CH_3$.

In another embodiment of the present invention, $R^3$ is halogen. In a class of this embodiment, $R^3$ is selected from Cl and F. In another class of this embodiment, $R^3$ is Cl. In another class of this embodiment, $R^3$ is F.

In another embodiment of the present invention, $R^3$ is —$C_{1-6}$alkyl, wherein each $C_{1-6}$alkyl is unsubstituted or substituted with one to three substituents selected from halogen. In a class of this embodiment, each $C_{1-6}$alkyl is unsubstituted or substituted with one to three substituents selected from Cl and F. In another class of this embodiment, each $C_{1-6}$alkyl is unsubstituted or substituted with one to three substituents selected from Cl. In another class of this embodiment, each $C_{1-6}$alkyl is unsubstituted or substituted with one to three substituents selected from F.

In another embodiment of the present invention, $R^3$ is —$C_{1-6}$alkyl. In another embodiment of the present invention, $R^3$ is —$C_{1-6}$alkyl, wherein each $C_{1-6}$alkyl is substituted with one to three substituents selected from halogen. In a class of this embodiment, each $C_{1-6}$alkyl is substituted with one to three substituents selected from Cl and F. In another class of this embodiment, each $C_{1-6}$alkyl is substituted with one to three substituents selected from Cl. In another class of this embodiment, each $C_{1-6}$alkyl is substituted with one to three substituents selected from F.

In another embodiment of the present invention, $R^3$ when present is selected from the group consisting of: $-CF_3$, $-CHF_2$, and $-CH_3$. In another embodiment of the present invention, $R^3$ is selected from the group consisting of: $-CF_3$, $-CHF_2$, and $-CH_3$. In another embodiment of the present invention, $R^3$ is $-CF_3$. In another embodiment of the present invention, $R^3$ is $-CHF_2$. In another embodiment of the present invention, $R^3$ is $-CH_3$.

In another embodiment of the present invention, $R^4$ is selected from: $-OC_{1-6}$alkyl, and $-C_{1-6}$alkyl, wherein $-C_{1-6}$alkyl is unsubstituted or substituted with one, two, three or four substituents selected from $R^5$. In another embodiment of the present invention, $R^4$ is selected from: $-O-(CH_2)_2CH(OH)(C(CH_3)_2OH)$, $-O-(CH_2)_2C(OH)(CH_3)CH_2OH$, $-O-CH_2CH(C(CH_3)_2OH)_2$, $-(CH_2)_2C(OH)(CH_3)CH_2OH$, $-O-(CH_2)_2CH(OH)CH_2OH$, $-O-(CH_2)_2C(OH)(CH_3)CH_3$, $-O-(CH_2)_3SO_2CH_3$, $-O-(CH_2)_2C(CH_3)_2OH$, $-O-(CH_2)_2C(OH)(CH_3)CHF_2$, and $-O-(CH_2)_2$-oxetane-OH. In another embodiment of the present invention, $R^4$ is selected from: $-O-(CH_2)_2CH(OH)(C(CH_3)_2OH)$, $-O-(CH_2)_2C(OH)(CH_3)CH_2OH$, $-O-CH_2CH(C(CH_3)_2OH)_2$, $-O-(CH_2)_2CH(OH)CH_2OH$, $-O-(CH_2)_2C(OH)(CH_3)CH_3$, $-O-(CH_2)_3SO_2CH_3$, $-O-(CH_2)_2C(CH_3)_2OH$, $-O-(CH_2)_2C(OH)(CH_3)CHF_2$, and $-O-(CH_2)_2$- oxetane-OH. In another embodiment of the present invention, $R^4$ is selected from the group consisting of: $-O-(CH_2)_2C(OH)(CH_3)CH_2OH$, $-O-(CH_2)_2C(CH_3)_2OH$, and $-O-(CH_2)_2C(OH)(CH_3)CHF_2$. In another embodiment of the present invention, $R^4$ is $-(CH_2)_2C(OH)(CH_3)CH_2OH$.

In another embodiment of the present invention $R^4$ is $-C_{1-6}$alkyl, wherein $-C_{1-6}$alkyl is unsubstituted or substituted with one, two, three or four substituents selected from $R^5$. In another embodiment of the present invention $R^4$ is $-C_{1-6}$alkyl, wherein $-C_{1-6}$alkyl is unsubstituted or substituted with three substituents selected from $R^5$. In another embodiment of the present invention $R^4$ is $-C_4$alkyl, wherein $-C_4$alkyl is unsubstituted or substituted with three substituents selected from $R^5$.

In another embodiment of the present invention, $R^4$ is $-OC_{1-6}$alkyl, wherein $-C_{1-6}$alkyl is unsubstituted or substituted with one, two, three or four substituents selected from $R^5$. In another embodiment of the present invention, $R^4$ is $-OC_{1-6}$alkyl. In another embodiment of the present invention, $R^4$ is $-OC_{1-6}$alkyl, wherein $-C_{1-6}$alkyl is substituted with one, two, three or four substituents selected from $R^5$. In another embodiment of the present invention, $R^4$ is $-OC_{1-6}$alkyl, wherein $-C_{1-6}$alkyl is substituted with one, two or three substituents selected from $R^5$. In another embodiment of the present invention, $R^4$ is $-OC_{1-6}$alkyl, wherein $-C_{1-6}$alkyl is substituted with one or two substituents selected from $R^5$. In another embodiment of the present invention, $R^4$ is $-OC_{1-6}$alkyl, wherein $-C_{1-6}$alkyl is substituted with one substituent selected from $R^5$. In another embodiment of the present invention, $R^4$ is $-OC_{1-3}$alkyl, wherein $-C_{1-3}$alkyl is substituted with one substituent selected from $R^5$. In another embodiment of the present invention, $R^4$ is $-OC_{2-3}$alkyl, wherein $-C_{2-3}$alkyl is substituted with one substituent selected from $R^5$. In another embodiment of the present invention, $R^4$ is $-OC_2$alkyl, wherein $-C_2$alkyl is substituted with one substituent selected from $R^5$. In another embodiment of the present invention, $R^4$ is $-OC_3$alkyl, wherein $-C_3$alkyl is substituted with one substituent selected from $R^5$.

In another embodiment of the present invention, $R^5$ is selected from the group consisting of: $-(CH_2)_s$halogen, $-C_{1-6}$alkyl, $-(CH_2)_s-O-C_{1-6}$alkyl, $-(CH_2)_sOH$, $-(CH_2)_sSO_2C_{1-6}$alkyl, $-(CH_2)_sSO_2-(CH_2)_t-C_{3-6}$cycloalkyl, $-(CH_2)_sC_{3-6}$cycloalkyl, $-(CH_2)_s-O-(CH_2)_t-C_{3-6}$cycloalkyl, and wherein each $CH_2$, $C_{1-6}$alkyl and $C_{3-6}$cycloalkyl is unsubstituted or substituted with one to three substituents selected from halogen and $-(CH_2)_wOH$. In a class of this embodiment, each $CH_2$, $C_{1-6}$alkyl and $C_{3-6}$cycloalkyl is unsubstituted or substituted with one to three substituents selected from halogen. In a class of this embodiment, each $CH_2$, $C_{1-6}$alkyl and $C_{3-6}$cycloalkyl is unsubstituted or substituted with one to three substituents selected from Cl and F. In another class of this embodiment, each $CH_2$, $C_{1-6}$alkyl and $C_{3-6}$cycloalkyl is unsubstituted or substituted with one to three substituents selected from Cl. In another class of this embodiment, each $CH_2$, $C_{1-6}$alkyl and $C_{3-6}$cycloalkyl is unsubstituted or substituted with one to three substituents selected from F.

In another embodiment of the present invention, $R^5$ is selected from the group consisting of: $-(CH_2)_s$halogen, $-C_{1-6}$alkyl, $-(CH_2)_s-O-C_{1-6}$alkyl, $-(CH_2)_sOH$, $-(CH_2)_sSO_2C_{1-6}$alkyl, $-(CH_2)_sSO_2-(CH_2)_t-C_{3-6}$cycloalkyl, $-(CH_2)_sC_{3-6}$cycloalkyl, $-(CH_2)_s-O-(CH_2)_t-C_{3-6}$cycloalkyl, and wherein each $CH_2$, $C_{1-6}$alkyl and $C_{3-6}$cycloalkyl is unsubstituted or substituted with one to three substituents selected from halogen. In a class of this embodiment, each $CH_2$, $C_{1-6}$alkyl and $C_{3-6}$cycloalkyl is unsubstituted or substituted with one to three substituents selected from Cl and F. In another class of this embodiment, each $CH_2$, $C_{1-6}$alkyl and $C_{3-6}$cycloalkyl is unsubstituted or substituted with one to three substituents selected from Cl. In another class of this embodiment, each $CH_2$, $C_{1-6}$alkyl and $C_{3-6}$cycloalkyl is unsubstituted or substituted with one to three substituents selected from F.

In another embodiment of the present invention, $R^5$ is selected from the group consisting of: $-C_{1-6}$alkyl, $-(CH_2)_sOH$, $-(CH_2)_sSO_2C_{1-6}$alkyl, $-(CH_2)_s$halogen, $-(CH_2)_sOC_{1-6}$alkyl, $-(CH_2)_sC_{3-6}$cycloalkyl, and wherein each $CH_2$, $C_{1-6}$alkyl and $C_{3-6}$cycloalkyl is unsubstituted or substituted with one to three substituents selected from halogen and $-(CH_2)_wOH$. In a class of this embodiment, each $CH_2$, $C_{1-6}$alkyl and $C_{3-6}$cycloalkyl is unsubstituted or substituted with one to three substituents selected from Cl and F. In another class of this embodiment, each CH$_2$, C$_{1-6}$alkyl and C$_{3-6}$cycloalkyl is unsubstituted or substituted with one to three substituents selected from Cl. In another class of this embodiment, each CH$_2$, C$_{1-6}$alkyl and C$_{3-6}$cycloalkyl is unsubstituted or substituted with one to three substituents selected from F.

In another embodiment of the present invention, R$^5$ is selected from the group consisting of: —C$_{1-6}$alkyl, —(CH$_2$)$_s$OH, —(CH$_2$)$_s$SO$_2$C$_{1-6}$alkyl, —(CH$_2$)$_s$halogen, —(CH$_2$)$_s$OC$_{1-6}$alkyl, —(CH$_2$)$_s$C$_{3-6}$cycloalkyl, and

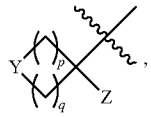

wherein each CH$_2$, C$_{1-6}$alkyl and C$_{3-6}$cycloalkyl is unsubstituted or substituted with one to three substituents selected from halogen. In a class of this embodiment, each CH$_2$, C$_{1-6}$alkyl and C$_{3-6}$cycloalkyl is unsubstituted or substituted with one to three substituents selected from Cl and F. In another class of this embodiment, each CH$_2$, C$_{1-6}$alkyl and C$_{3-6}$cycloalkyl is unsubstituted or substituted with one to three substituents selected from Cl. In another class of this embodiment, each CH$_2$, C$_{1-6}$alkyl and C$_{3-6}$cycloalkyl is unsubstituted or substituted with one to three substituents selected from F.

In another embodiment of the present invention, R$^5$ is selected from the group consisting of: —C$_{1-6}$alkyl, —(CH$_2$)$_s$OH, —(CH$_2$)$_s$SO$_2$C$_{1-6}$alkyl, and

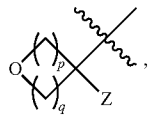

wherein each CH$_2$ and C$_{1-6}$alkyl is unsubstituted or substituted with one to three substituents selected from halogen. In a class of this embodiment, each CH$_2$ and C$_{1-6}$alkyl is unsubstituted or substituted with one to three substituents selected from Cl and F. In another class of this embodiment, each CH$_2$ and C$_{1-6}$alkyl is unsubstituted or substituted with one to three substituents selected from Cl. In another class of this embodiment, each CH$_2$ and C$_{1-6}$alkyl is unsubstituted or substituted with one to three substituents selected from F.

In another embodiment of the present invention, R$^5$ is selected from the group consisting of: halogen, —C$_{1-6}$alkyl, —OH, —SO$_2$C$_{1-6}$alkyl, and

In another embodiment of the present invention, R$^5$ is selected from the group consisting of: F, —CH$_3$, —OH, —SO$_2$CH$_3$, and

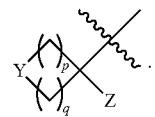

In another embodiment of the present invention, R$^5$ is selected from the group consisting of: F, —CH$_3$, —OH, —SO$_2$CH$_3$, and

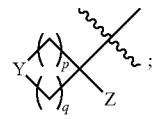

and wherein Y is oxygen, Z is —OH, p is 1 and q is 1.

In another embodiment of the present invention, R$^5$ is selected from the group consisting of: —C$_{1-6}$alkyl, —OH, —SO$_2$C$_{1-6}$alkyl, and

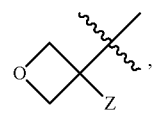

wherein each CH$_2$ and C$_{1-6}$alkyl is unsubstituted or substituted with one to three substituents selected from halogen. In a class of this embodiment, each CH$_2$ and C$_{1-6}$alkyl is unsubstituted or substituted with one to three substituents selected from Cl and F. In another class of this embodiment, each CH$_2$ and C$_{1-6}$alkyl is unsubstituted or substituted with one to three substituents selected from Cl. In another class of this embodiment, each CH$_2$ and C$_{1-6}$alkyl is unsubstituted or substituted with one to three substituents selected from F.

In another embodiment of the present invention, R$^5$ is selected from the group consisting of: —CH$_3$, —OH, —SO$_2$CH$_3$, and

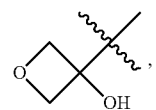 [SMILES: *C1(O)COC1]

wherein each CH$_3$ and CH$_2$ is unsubstituted or substituted with one to three substituents selected from halogen. In a class of this embodiment, each CH$_3$ and CH$_2$ is unsubstituted or substituted with one to three substituents selected from Cl and F. In another class of this embodiment, each CH$_3$ and CH$_2$ is unsubstituted or substituted with one to three substituents selected from Cl. In another class of this embodiment, each CH$_3$ and CH$_2$ is unsubstituted or substituted with one to three substituents selected from F.

In another embodiment of the present invention, R$^5$ is selected from the group consisting of: —C$_{1-6}$alkyl, and —(CH$_2$)$_s$OH, wherein each CH$_2$ and C$_{1-6}$alkyl is unsubstituted or substituted with one to three substituents selected from halogen. In a class of this embodiment, R$^5$ is selected from the group consisting of: —CH$_3$ and —OH, wherein each CH$_3$ is unsubstituted or substituted with one to three substituents selected from halogen. In another class of this embodiment, each CH$_3$ is unsubstituted or substituted with one to three substituents selected from Cl and F. In another class of this embodiment, each $CH_3$ is unsubstituted or substituted with one to three substituents selected from Cl. In another class of this embodiment, each $CH_3$ is unsubstituted or substituted with one to three substituents selected from F.

In another embodiment of the present invention, $R^5$ is selected from: $-(CH_2)_sSO_2C_{1-6}$alkyl, wherein each $CH_2$ and $C_{1-6}$alkyl is unsubstituted or substituted with one to three substituents selected from halogen. In a class of this embodiment, $R^5$ is $-SO_2CH_3$, wherein each $CH_3$ is unsubstituted or substituted with one to three substituents selected from halogen. In another class of this embodiment, each $CH_3$ is unsubstituted or substituted with one to three substituents selected from Cl and F. In another class of this embodiment, each $CH_3$ is unsubstituted or substituted with one to three substituents selected from Cl. In another class of this embodiment, each $CH_3$ is unsubstituted or substituted with one to three substituents selected from F.

In another embodiment of the present invention, $R^5$ is selected from the group consisting of:

wherein each $CH_2$ is unsubstituted or substituted with one to three substituents selected from halogen. In a class of this embodiment, $R^5$ is wherein each $CH_2$ is unsubstituted or substituted with one to three substituents selected from halogen. In another class of this embodiment, each $CH_2$ is unsubstituted or substituted with one to three substituents selected from Cl and F. In another class of this embodiment, each $CH_2$ is unsubstituted or substituted with one to three substituents selected from Cl. In another class of this embodiment, each $CH_2$ is unsubstituted or substituted with one to three substituents selected from F.

In another embodiment of the present invention, Y is selected from: $-CH(OH)-$, $-C(C_{1-6}alkyl)(OH)-$, $-C[(CH_2)_t-C_{3-6}cycloalkyl](OH)-$, O, S and $SO_2$, wherein each $CH_2$, $C_{1-6}$alkyl and $C_{3-6}$cycloalkyl is unsubstituted or substituted with one to three substituents selected from halogen and $(CH_2)_wOH$. In a class of this embodiment, each $CH_2$, $C_{1-6}$alkyl and $C_{3-6}$cycloalkyl is unsubstituted or substituted with one to three substituents selected from halogen. In another class of this embodiment, each $CH_2$, $C_{1-6}$alkyl and $C_{3-6}$cycloalkyl is unsubstituted or substituted with one to three substituents selected from Cl and F. In another class of this embodiment, each $CH_2$, $C_{1-6}$alkyl and $C_{3-6}$cycloalkyl is unsubstituted or substituted with one to three substituents selected from Cl. In another class of this embodiment, each $CH_2$, $C_{1-6}$alkyl and $C_{3-6}$cycloalkyl is unsubstituted or substituted with one to three substituents selected from F.

In another embodiment of the present invention, Y is selected from: $-CH(OH)-$, $-C(CH_3)(OH)-$, O, S and $SO_2$, wherein each $CH_3$ is unsubstituted or substituted with one to three substituents selected from halogen and $(CH_2)_wOH$. In a class of this embodiment, each $CH_3$ is unsubstituted or substituted with one to three substituents selected from halogen. In another class of this embodiment, each $CH_3$ is unsubstituted or substituted with one to three substituents selected from Cl and F. In another class of this embodiment, each $CH_3$ is unsubstituted or substituted with one to three substituents selected from Cl. In another class of this embodiment, each $CH_3$ is unsubstituted or substituted with one to three substituents selected from F.

In another embodiment of the present invention, Y is selected from: $-CH(OH)-$, $-C(CH_3)(OH)-$, O, S, and $SO_2$. In another embodiment of the present invention, Y is selected from: $-CH(OH)-$ and $-C(CH_3)(OH)-$. In another embodiment of the present invention, Y is selected from: O, S and $SO_2$. In another embodiment of the present invention, Y is selected from: S and $SO_2$. In another embodiment of the present invention, Y is sulfur. In another embodiment of the present invention, Y is $SO_2$. In another embodiment of the present invention, Y is oxygen.

In another embodiment of the present invention, Z is selected from: hydrogen, $-C_{1-6}$alkyl, $-(CH_2)_s-O-C_{1-6}$alkyl, $-(CH_2)_s-OH$, $-(CH_2)_sSO_2C_{1-6}$alkyl, $-(CH_2)_sSO_2-(CH_2)_t-C_{3-6}$cycloalkyl, $-(CH_2)_sC_{3-6}$cycloalkyl, and $-(CH_2)_s-O-(CH_2)_t-C_{3-6}$cycloalkyl, wherein each $CH_2$, $C_{1-6}$alkyl and $C_{3-6}$cycloalkyl is unsubstituted or substituted with one to three substituents selected from halogen.

In another embodiment of the present invention, Z is selected from: $-C_{1-6}$alkyl, $-(CH_2)_s-O-C_{1-6}$alkyl, $-(CH_2)_s-OH$, $-(CH_2)_sSO_2C_{1-6}$alkyl, $-(CH_2)_sSO_2-(CH_2)_t-C_{3-6}$cycloalkyl, $-(CH_2)_sC_{3-6}$cycloalkyl, and $-(CH_2)_s-O-(CH_2)_t-C_{3-6}$cycloalkyl, wherein each $CH_2$, $C_{1-6}$alkyl and $C_{3-6}$cycloalkyl is unsubstituted or substituted with one to three substituents selected from halogen.

In another embodiment of the present invention, Z is selected from: hydrogen, $-C_{1-6}$alkyl, $-(CH_2)_s-O-C_{1-6}$alkyl, $-(CH_2)_s-OH$ and $-(CH_2)_sC_{3-6}$cycloalkyl, wherein each $CH_2$, $C_{1-6}$alkyl and $C_{3-6}$cycloalkyl is unsubstituted or substituted with one to three substituents selected from halogen.

In another embodiment of the present invention, Z is selected from: $-C_{1-6}$alkyl, $-(CH_2)_s-O-C_{1-6}$alkyl, $-(CH_2)_s-OH$ and $-(CH_2)_sC_{3-6}$cycloalkyl, wherein each $CH_2$, $C_{1-6}$alkyl and $C_{3-6}$cycloalkyl is unsubstituted or substituted with one to three substituents selected from halogen.

In another embodiment of the present invention, Z is selected from: hydrogen, $-C_{1-6}$alkyl, $-(CH_2)_s-O-C_{1-6}$alkyl and $-(CH_2)_s-OH$, wherein each $CH_2$, and $C_{1-6}$alkyl is unsubstituted or substituted with one to three substituents selected from halogen.

In another embodiment of the present invention, Z is selected from: $-C_{1-6}$alkyl, $-(CH_2)_s-O-C_{1-6}$alkyl and $-(CH_2)_s-OH$, wherein each $CH_2$, and $C_{1-6}$alkyl is unsubstituted or substituted with one to three substituents selected from halogen.

In another embodiment of the present invention, Z is selected from: hydrogen, $-C_{1-6}$alkyl, and $-(CH_2)_s-OH$, wherein each $CH_2$, and $C_{1-6}$alkyl is unsubstituted or substituted with one to three substituents selected from halogen.

In another embodiment of the present invention, Z is selected from: $-C_{1-6}$alkyl, and $-(CH_2)_5-OH$, wherein each $CH_2$, and $C_{1-6}$alkyl is unsubstituted or substituted with one to three substituents selected from halogen.

In another embodiment of the present invention, Z is hydrogen.

In another embodiment of the present invention, Z is selected from: —$C_{1-6}$alkyl, wherein $C_{1-6}$alkyl is unsubstituted or substituted with one to three substituents selected from halogen. In another embodiment of the present invention, Z is selected from —$(CH_2)_s$—OH, wherein each $CH_2$ is unsubstituted or substituted with one to three substituents selected from halogen. In another embodiment of the present invention, Z is selected from —$(CH_2)_s$—OH. In another embodiment of the present invention, Z is —OH.

In another embodiment of the present invention, m is 0, 1, 2 or 3. In another embodiment of the present invention, m is 0, 1 or 2. In another embodiment of the present invention, m is 0, 1 or 3. In another embodiment of the present invention, m is 0, 2 or 3. In another embodiment of the present invention, m is 0 or 2. In another embodiment of the present invention, m is 0 or 1. In another embodiment of the present invention, m is 0 or 3. In another embodiment of the present invention, m is 1, 2 or 3. In another embodiment of the present invention, m is 1 or 3. In another embodiment of the present invention, m is 1 or 2. In another embodiment of the present invention, m is 0. In another embodiment of the present invention, m is 1. In another embodiment of the present invention, m is 2. In another embodiment of the present invention, m is 3.

In another embodiment of the present invention, n=1 or 2. In another embodiment of the present invention, n is 1. In another embodiment of the present invention, n is 2.

In another embodiment of the present invention, p=0, 1, 2 or 3. In another embodiment of the present invention, p is 0, 1 or 2. In another embodiment of the present invention, p is 0, 1 or 3. In another embodiment of the present invention, p is 0, 2 or 3. In another embodiment of the present invention, p is 0 or 2. In another embodiment of the present invention, p is 0 or 1. In another embodiment of the present invention, p is 0 or 3. In another embodiment of the present invention, p is 1, 2 or 3. In another embodiment of the present invention, p is 1 or 3. In another embodiment of the present invention, p is 1 or 2. In another embodiment of the present invention, p is 2 or 3. In another embodiment of the present invention, p is 0. In another embodiment of the present invention, p is 1. In another embodiment of the present invention, p is 2. In another embodiment of the present invention, p is 3.

In another embodiment of the present invention, q=0, 1, 2 or 3. In another embodiment of the present invention, q is 0, 1 or 2. In another embodiment of the present invention, q is 0, 1 or 3. In another embodiment of the present invention, q is 0, 2 or 3. In another embodiment of the present invention, q is 0 or 2. In another embodiment of the present invention, q is 0 or 1. In another embodiment of the present invention, q is 0 or 3. In another embodiment of the present invention, q is 1, 2 or 3. In another embodiment of the present invention, q is 1 or 3. In another embodiment of the present invention, q is 1 or 2. In another embodiment of the present invention, q is 2 or 3. In another embodiment of the present invention, q is 0. In another embodiment of the present invention, q is 1. In another embodiment of the present invention, q is 2. In another embodiment of the present invention, q is 3.

In another embodiment p+q is at least 2. In another embodiment, p+q is 2 or greater. In another embodiment, p+q is 2, 3, 4, 5 or 6. In another embodiment, p is 1 and q is 1. In another embodiment, p is 0 and q is 2. In another embodiment, p is 2 and q is 0. In another embodiment, p is 2 and q is 1. In another embodiment, p is 1 and q is 2. In another embodiment p is 2 and q is 2. In another embodiment, p is 3 and q is 2. In another embodiment, p is 2 and q is 3. In another embodiment, p is 3 and q is 3. In another embodiment, p is 0 and q is 3. In another embodiment, p is 3 and q is 0. In another embodiment, p is 1 and q is 3. In another embodiment, p is 3 and q is 1.

In another embodiment of the present invention, r=0, 1, 2 or 3. In another embodiment of the present invention, r is 0, 1 or 2. In another embodiment of the present invention, r is 0, 1 or 3. In another embodiment of the present invention, r is 0, 2 or 3. In another embodiment of the present invention, r is 0 or 2. In another embodiment of the present invention, r is 0 or 1. In another embodiment of the present invention, r is 0 or 3. In another embodiment of the present invention, r is 1, 2 or 3. In another embodiment of the present invention, r is 1 or 3. In another embodiment of the present invention, r is 1 or 2. In another embodiment of the present invention, r is 2 or 3. In another embodiment of the present invention, r is 0. In another embodiment of the present invention, r is 1. In another embodiment of the present invention, r is 2. In another embodiment of the present invention, r is 3.

In another embodiment of the present invention, s=0, 1, 2 or 3. In another embodiment of the present invention, s is 0, 1 or 2. In another embodiment of the present invention, s is 0, 1 or 3. In another embodiment of the present invention, s is 0, 2 or 3. In another embodiment of the present invention, s is 0 or 2. In another embodiment of the present invention, s is 0 or 1. In another embodiment of the present invention, s is 0 or 3. In another embodiment of the present invention, s is 1, 2 or 3. In another embodiment of the present invention, s is 1 or 3. In another embodiment of the present invention, s is 1 or 2. In another embodiment of the present invention, s is 2 or 3. In another embodiment of the present invention, s is 0. In another embodiment of the present invention, s is 1. In another embodiment of the present invention, s is 2. In another embodiment of the present invention, s is 3.

In another embodiment of the present invention, t=0, 1, 2 or 3. In another embodiment of the present invention, t is 0, 1 or 2. In another embodiment of the present invention, t is 0, 1 or 3. In another embodiment of the present invention, t is 0, 2 or 3. In another embodiment of the present invention, t is 0 or 2. In another embodiment of the present invention, t is 0 or 1. In another embodiment of the present invention, t is 0 or 3. In another embodiment of the present invention, t is 1, 2 or 3. In another embodiment of the present invention, t is 1 or 3. In another embodiment of the present invention, t is 1 or 2. In another embodiment of the present invention, t is 2 or 3. In another embodiment of the present invention, t is 0. In another embodiment of the present invention, t is 1. In another embodiment of the present invention, t is 2. In another embodiment of the present invention, t is 3.

In another embodiment of the present invention, u=0, 1, 2 or 3. In another embodiment of the present invention, u is 0, 1 or 2. In another embodiment of the present invention, u is 0, 1 or 3. In another embodiment of the present invention, u is 0, 2 or 3. In another embodiment of the present invention, u is 0 or 2. In another embodiment of the present invention, u is 0 or 1. In another embodiment of the present invention, u is 0 or 3. In another embodiment of the present invention, u is 1, 2 or 3. In another embodiment of the present invention, u is 1 or 3. In another embodiment of the present invention, u is 1 or 2. In another embodiment of the present invention, u is 2 or 3. In another embodiment of the present invention, u is 0. In another embodiment of the present invention, u is 1. In another embodiment of the present invention, u is 2. In another embodiment of the present invention, u is 3.

In another embodiment of the present invention, v=0, 1, 2 or 3. In another embodiment of the present invention, v is 0, 1 or 2. In another embodiment of the present invention, v is 0, 1 or 3. In another embodiment of the present invention, v is 0, 2 or 3. In another embodiment of the present invention, v is 0 or 2. In another embodiment of the present invention, v is 0 or 1. In another embodiment of the present invention, v is 0 or 3. In another embodiment of the present invention, v is 1, 2 or 3. In another embodiment of the present invention, v is 1 or 3. In another embodiment of the present invention, v is 1 or 2. In another embodiment of the present invention, v is 2 or 3. In another embodiment of the present invention, v is 0. In another embodiment of the present invention, v is 1. In another embodiment of the present invention, v is 2. In another embodiment of the present invention, v is 3.

In another embodiment of the present invention, w=0, 1, 2 or 3. In another embodiment of the present invention, w is 0, 1 or 2. In another embodiment of the present invention, w is 0, 1 or 3. In another embodiment of the present invention, w is 0, 2 or 3. In another embodiment of the present invention, w is 0 or 2. In another embodiment of the present invention, w is 0 or 1. In another embodiment of the present invention, w is 0 or 3. In another embodiment of the present invention, w is 1, 2 or 3. In another embodiment of the present invention, w is 1 or 3. In another embodiment of the present invention, w is 1 or 2. In another embodiment of the present invention, w is 2 or 3. In another embodiment of the present invention, w is 0. In another embodiment of the present invention, w is 1. In another embodiment of the present invention, w is 2. In another embodiment of the present invention, w is 3.

In another embodiment of the present invention, the invention relates to compounds of structural formula Ia:

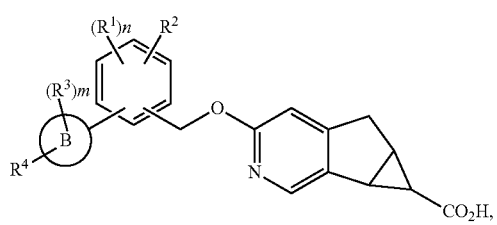

Ia wherein B is selected from: phenyl and pyridyl; or a pharmaceutically acceptable salt thereof.

In another embodiment of the present invention, the invention relates to compounds of structural formula Ib:

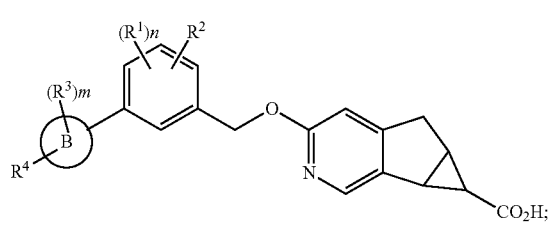

Ib wherein B is selected from: phenyl and pyridyl; or a pharmaceutically acceptable salt thereof.

In another embodiment of the present invention, the invention relates to compounds of structural formula Ic:

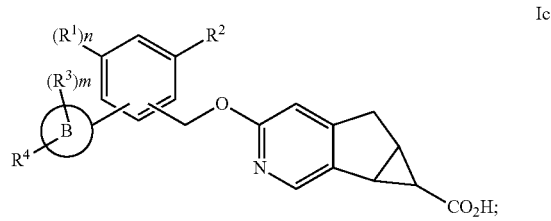

Ic wherein B is selected from: phenyl and pyridyl; or a pharmaceutically acceptable salt thereof.

In another embodiment of the present invention, the invention relates to compounds of structural formula Id:

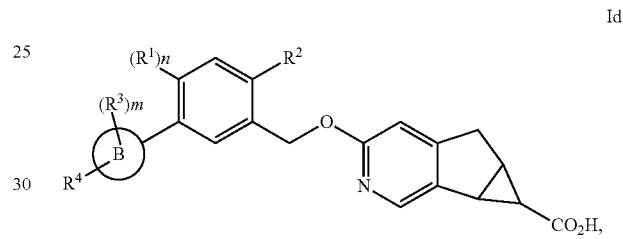

Id wherein B is selected from: phenyl and pyridyl; or a pharmaceutically acceptable salt thereof.

In another embodiment of the present invention, the invention relates to compounds of structural formula If:

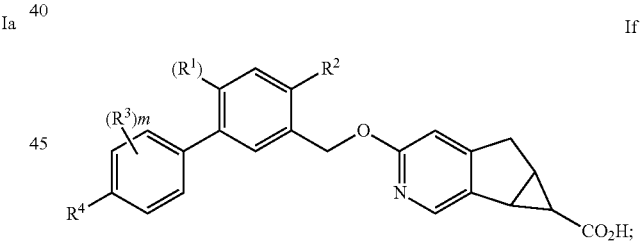

If or a pharmaceutically acceptable salt thereof.

In another embodiment of the present invention, the invention relates to compounds of structural formula Ig:

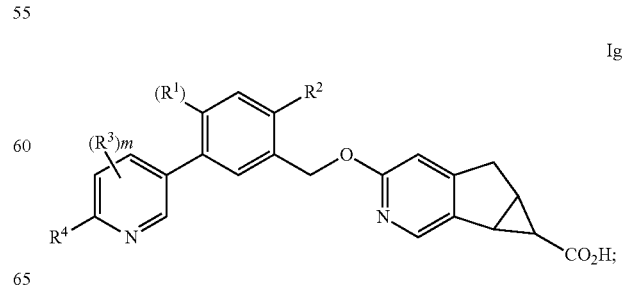

Ig or a pharmaceutically acceptable salt thereof.

The compound of structural formula I, includes the compounds of structural formulas Ia, Ib, Ic, Id, Ie, If and Ig, and pharmaceutically acceptable salts, hydrates and solvates thereof.

Another embodiment of the present invention relates to compounds of structural formula I wherein:
A is phenyl;
B is selected from the group consisting of:
  (1) phenyl, and
  (2) pyridyl;
$R^1$ is selected from the group consisting of:
  (1) halogen, and
  (2) —$C_{1-6}$alkyl,
wherein each —$C_{1-6}$alkyl is unsubstituted or substituted with one to four substituents selected from halogen;
$R^2$ is halogen;
$R^3$ when present is selected from the group consisting of:
  (1) halogen, and
  (2) —$C_{1-6}$alkyl,
wherein each $C_{1-6}$alkyl is unsubstituted or substituted with one to three substituents selected from halogen;
$R^4$ is selected from:
  (1) —$OC_{1-6}$alkyl, and
  (2) —$C_{1-6}$alkyl,
wherein —$C_{1-6}$alkyl is unsubstituted or substituted with one, two, three or four substituents selected from $R^5$;
$R^5$ is selected from the group consisting of:
  (1) halogen,
  (2) —$C_{1-6}$alkyl,
  (3) —OH,
  (4) —$SO_2C_{1-6}$alkyl, and

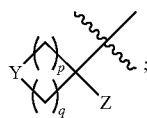

Y is O;
Z is —OH;
m is 0, 1, 2 or 3;
n is 1 or 2;
p is 1; and
q is 1.

Another embodiment of the present invention relates to compounds of structural formula I wherein:
A is phenyl;
B is phenyl;
$R^1$ is selected from the group consisting of:
  (1) halogen, and
  (2) —$C_{1-6}$alkyl,
wherein each —$C_{1-6}$alkyl is unsubstituted or substituted with one to four substituents selected from halogen;
$R^2$ is halogen;
$R^3$ when present is selected from the group consisting of:
  (1) halogen, and
  (2) —$C_{1-6}$alkyl,
wherein each $C_{1-6}$alkyl is unsubstituted or substituted with one to three substituents selected from halogen;
$R^4$ is selected from:
  (1) —$OC_{1-6}$alkyl, and
  (2) —$C_{1-6}$alkyl,
wherein —$C_{1-6}$alkyl is unsubstituted or substituted with one, two, three or four substituents selected from $R^5$;
$R^5$ is selected from the group consisting of:
  (1) halogen,
  (2) —$C_{1-6}$alkyl,
  (3) —OH,
  (4) —$SO_2C_{1-6}$alkyl, and

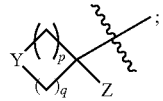

Y is O;
Z is —OH;
m is 0, 1, 2 or 3;
n is 1 or 2;
p is 1; and
q is 1.

Another embodiment of the present invention relates to compounds of structural formula I wherein:
A is phenyl;
B is pyridyl;
$R^1$ is selected from the group consisting of:
  (1) halogen, and
  (2) —$C_{1-6}$alkyl,
wherein each —$C_{1-6}$alkyl is unsubstituted or substituted with one to four substituents selected from halogen;
$R^2$ is halogen;
$R^3$ when present is selected from the group consisting of:
  (1) halogen, and
  (2) —$C_{1-6}$alkyl;
$R^4$ is —$OC_{1-6}$alkyl, wherein —$C_{1-6}$alkyl is unsubstituted or substituted with one, two, three or four substituents selected from $R^5$;
$R^5$ is selected from the group consisting of:
  (1) halogen,
  (2) —$C_{1-6}$alkyl,
  (3) —OH,
  (4) —$SO_2C_{1-6}$alkyl, and

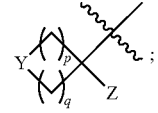

Y is O;
Z is OH;
m is 0, 1, 2 or 3;
n is 1 or 2;
p is 1; and
q is 1.

Another embodiment of the present invention relates to compounds of structural formula I wherein:
A is phenyl;
B is phenyl or pyridyl;
$R^1$ is selected from the group consisting of:
  (1) halogen, and
  (2) —$C_{1-6}$alkyl,
wherein —$C_{1-6}$alkyl is unsubstituted or substituted with one to four substituents selected from halogen;
$R^2$ is halogen;
$R^3$ is selected from the group consisting of:
  (1) halogen, and
  (2) —$C_{1-6}$alkyl,
wherein each $C_{1-6}$alkyl is unsubstituted or substituted with one to three substituents selected from halogen;

$R^4$ is $OC_{1-6}$alkyl, wherein —$C_{1-6}$alkyl is substituted with one substituent selected from $R^5$;
$R^5$ is selected from the group consisting of:
(1) —$C_{1-6}$alkyl,
(2) —$(CH_2)_s$OH,
(3) —$(CH_2)_sSO_2C_{1-6}$alkyl, and

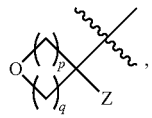
(4)

wherein each $CH_2$ and $C_{1-6}$alkyl is unsubstituted or substituted with one to three substituents selected from halogen; and
Z is selected from:
(1) hydrogen,
(2) —$C_{1-6}$alkyl,
(3) —$(CH_2)_s$—O—$C_{1-6}$alkyl, and
(4) —$(CH_2)_s$—OH,
wherein each $CH_2$, and $C_{1-6}$alkyl is unsubstituted or substituted with one to three substituents selected from halogen;
or a pharmaceutically acceptable salt thereof.

Another embodiment of the present invention relates to compounds of structural formula I wherein:

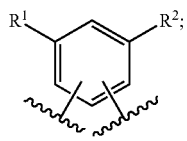

A is:
B is phenyl or pyridyl;
$R^1$ is selected from the group consisting of:
(1) halogen, and
(2) —$C_{1-6}$alkyl,
wherein —$C_{1-6}$alkyl is unsubstituted or substituted with one to four substituents selected from halogen;
$R^2$ is halogen;
$R^3$ is selected from the group consisting of:
(1) halogen, and
(2) —$C_{1-6}$alkyl,
wherein each $C_{1-6}$alkyl is unsubstituted or substituted with one to three substituents selected from halogen;

$R^4$ is $OC_{1-6}$alkyl, wherein —$C_{1-6}$alkyl is substituted with one substituent selected from $R^5$;
$R^5$ is selected from the group consisting of:
(1) —$C_{1-6}$alkyl,
(2) —OH,
(3) —$SO_2C_{1-6}$alkyl, and

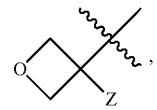
(4)

wherein each $CH_2$ and $C_{1-6}$alkyl is unsubstituted or substituted with one to three substituents selected from halogen;
Z is —$(CH_2)_s$—OH;
or a pharmaceutically acceptable salt thereof.

Another embodiment of the present invention relates to compounds of structural formula I wherein:
A is

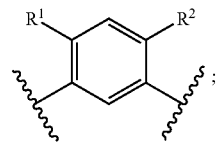

B is phenyl;
$R^1$ is —$C_{1-6}$alkyl, wherein each —$C_{1-6}$alkyl is substituted with one, two or three substituents selected from halogen;
$R^2$ is F;
$R^3$ is selected from the group consisting of:
(1) halogen, and
(2) —$C_{1-6}$alkyl,
wherein each $C_{1-6}$alkyl is unsubstituted or substituted with one to three substituents selected from halogen;
$R^4$ is $OC_{1-6}$alkyl, wherein —$C_{1-6}$alkyl is substituted with one substituent selected from $R^5$;
$R^5$ is selected from the group consisting of:
(1) —$C_{1-6}$alkyl, and
(2) —$(CH_2)_s$OH,
wherein each $CH_2$ and $C_{1-6}$alkyl is unsubstituted or substituted with one to three substituents selected from halogen;
or a pharmaceutically acceptable salt thereof.

Illustrative, but non-limiting, examples of the compounds of the present invention that are useful as agonists of G-protein-coupled receptor 40 (GPR40) are the following compounds:

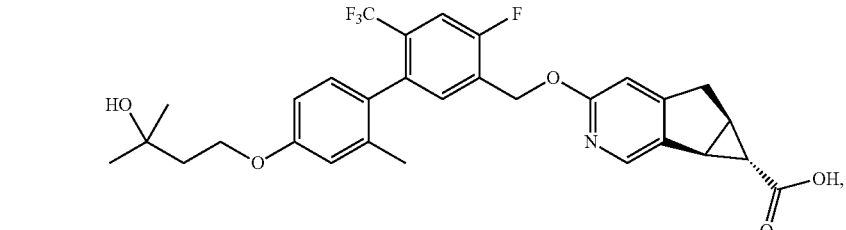

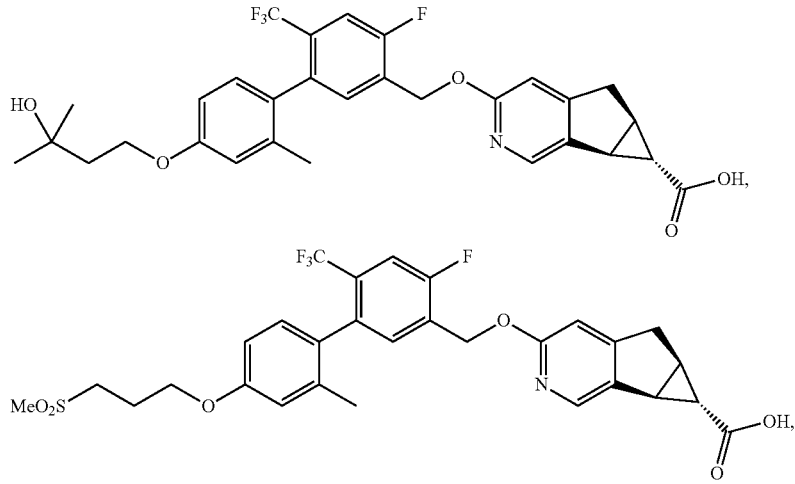

-continued
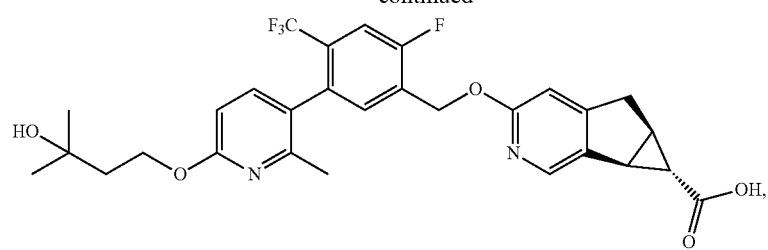
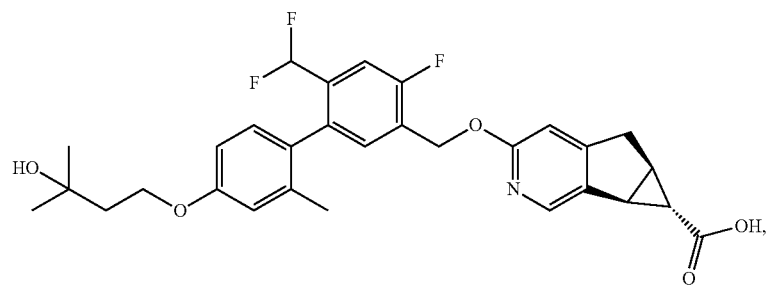
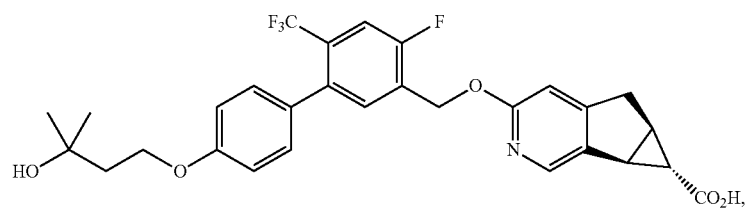
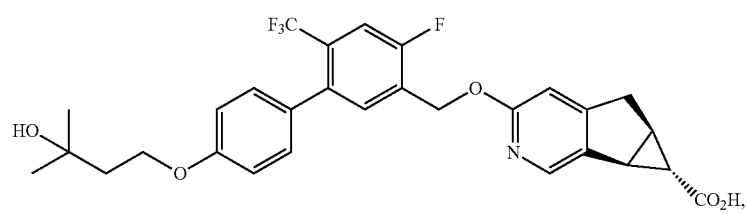
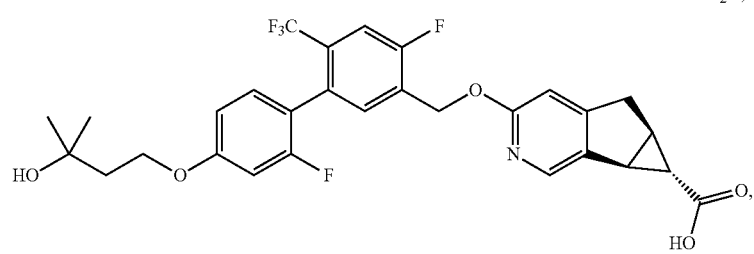
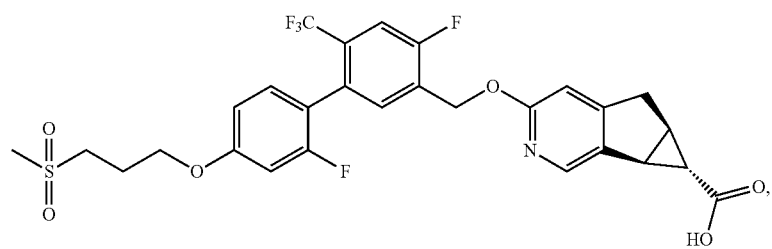
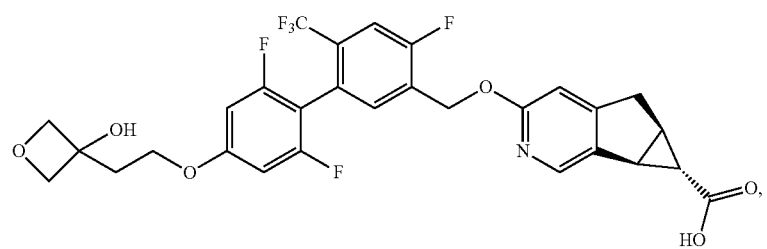

-continued
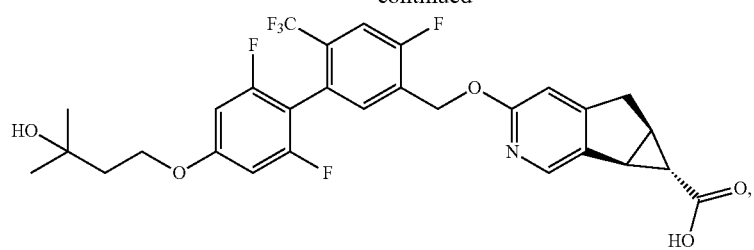
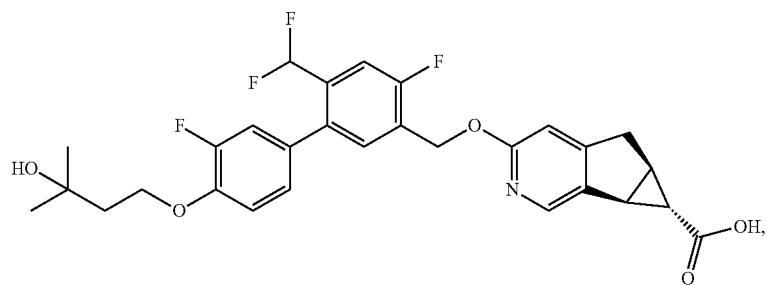
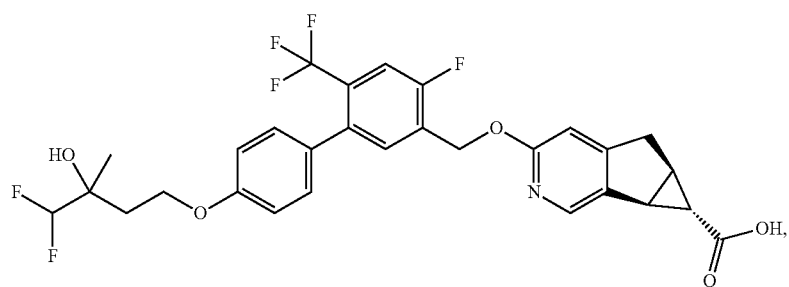
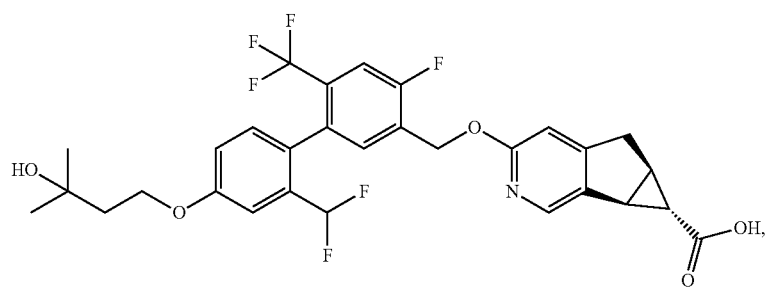
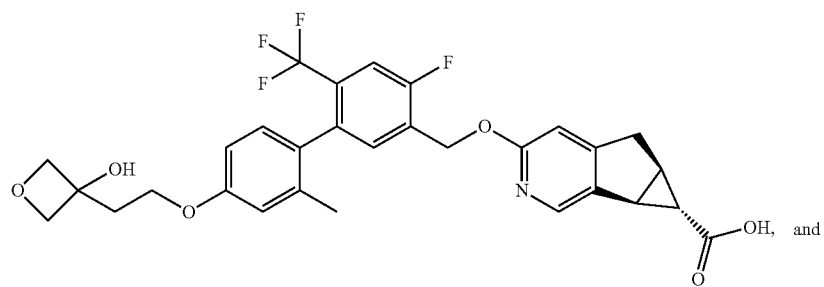

-continued

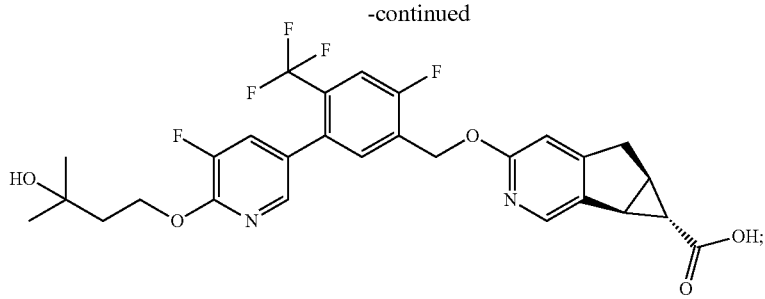

and pharmaceutically acceptable salts thereof.

In one embodiment of the present invention, the compounds of formula I have the absolute stereochemistry at the two stereogenic carbon centers as indicated in the compound of structural formula Ie:

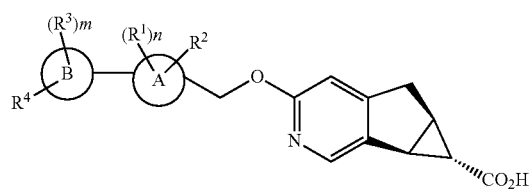

and pharmaceutically acceptable salts thereof.

Although the specific stereochemistries described above are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(=O)-$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclobutyl, cyclopentyl, cyclohexyl, cycloheptyl, and the like. In one embodiment of the present invention, cycloalkyl is selected from: cyclopropane, cyclobutane and cyclohexane. In another embodiment of the present invention, cycloalkyl is cyclopropane.

"Halogen" includes fluorine, chlorine, bromine and iodine. In another embodiment of the present invention, halogen includes fluorine, chlorine and iodine. In another embodiment of the present invention, halogen includes fluorine and chlorine. In another embodiment of the present invention, halogen is chlorine. In another embodiment of the present invention, halogen is fluorine.

"Me" represents methyl.

When any variable (e.g., $R^1$, Ra, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

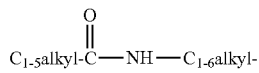

In choosing compounds of the present invention, one of ordinary skill in the art will recognize that the various substituents, i.e., $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases: (1) non-insulin dependent diabetes mellitus (Type 2 diabetes); (2) hyperglycemia; (3) insulin resistance; (4) Metabolic Syndrome; (5) obesity; (6) hypercholesterolemia; (7) hypertriglyceridemia (elevated levels of triglyceride-rich-lipoproteins); (8) mixed or diabetic dyslipidemia; (9) low HDL cholesterol; (10) high LDL cholesterol; (11) hyperapo-B-liproteinemia; and (12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases: (1) Type 2 diabetes, and specifically hyperglycemia associated with Type 2 diabetes; (2) Metabolic Syndrome; (3) obesity; and (4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hypperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

Certain compounds of the present invention of formula Id have the unexpected benefit of lower clearance in standard pharmacokinetic assays done in preclinical species, such as dogs and rats, compared to the corresponding compounds with no $R^1$ and $R^2$ substituents. Due to the lower clearance, these compounds of the present invention exhibit a longer half life (or a longer mean residence time).

Certain compounds of the present invention such as compounds in which the A ring is substituted with one $R^2$ substituent selected from halogen, and the A ring is also substituted with at least one $R^1$ substituent, and in which the B-ring is pyridyl substituted with at least one $R^3$ substituent have the unexpected benefit of improved potency compared to the corresponding compounds in which the A ring is unsubstituted (i.e. compounds with no $R^1$ and $R^2$ substituents on the A ring) and in which the B-ring is pyridyl substituted with at least one $R^3$ substituent.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated ($\geq 140$ mmHg/$\geq 90$ mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared ($kg/m^2$). "Obesity" refers to a condition whereby an otherwise healthy subject has a Body Mass Index (BMI) greater than or equal to 30 $kg/m^2$, or a condition whereby a subject with at least one co-morbidity has a BMI greater than or equal to 27 $kg/m^2$. An "obese subject" is an otherwise healthy subject with a Body Mass Index (BMI) greater than or equal to 30 $kg/m^2$ or a subject with at least one co-morbidity with a BMI greater than or equal to 27 $kg/m^2$. An overweight subject is a subject at risk of obesity. A "subject at risk of obesity" is an otherwise healthy subject with a BMI of 25 $kg/m^2$ to less than 30 $kg/m^2$ or a subject with at least one co-morbidity with a BMI of 25 $kg/m^2$ to less than 27 $kg/m^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m². In Asian countries, including Japan, an "obese subject" refers to a subject with at least one obesity-induced or obesity-related co-morbidity that requires weight reduction or that would be improved by weight reduction, with a BMI greater than or equal to 25 kg/m². In Asia-Pacific, a "subject at risk of obesity" is a subject with a BMI of greater than 23 kg/m² to less than 25 kg/m².

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual, human or other mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

Additionally, in the treatment or prevention of conditions which require agonism of GPR40 receptor activity, an appropriate dosage level will generally be about 0.01 to 500 mg per kg patient body weight per week, which can be administered in single or multiple doses. Preferably, the dosage level will be about 0.1 to about 250 mg/kg per week; more preferably about 0.5 to about 100 mg/kg per week. A suitable dosage level may be about 0.01 to 250 mg/kg per week, about 0.05 to 100 mg/kg per week, or about 0.1 to 50 mg/kg per week. Within this range the dosage may be 0.05 to 0.5, 0.5 to 5 or 5 to 50 mg/kg per week. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may also be administered on a regimen of 1 to 4 times per week, preferably once or twice per week.

When treating or preventing diabetes mellitus and/or hyperglycemia or hypertriglyceridemia or other diseases for which compounds of the present invention are indicated, generally satisfactory results are obtained when the compounds of the present invention are administered at a weekly dosage of from about 0.1 mg to about 100 mg per kilogram of animal body weight, preferably given as a single weekly dose or in divided doses two to six times a week, or in sustained release form. For most large mammals, the total weekly dosage is from about 1.0 mg to about 1000 mg, preferably from about 1 mg to about 50 mg. In the case of a 70 kg adult human, the total weekly dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have Type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPARγ agonists, when the patient's glycemic levels are not adequately responding to treatment.

When a compound of the present invention is used contemporaneously with one or more other drugs, a pharmaceutical composition in unit dosage form containing such other drugs and the compound of the present invention is preferred. However, the combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients that may be administered separately or in the same pharmaceutical composition in combination with a compound of the formulas described herein include, but are not limited to:

(1) other dipeptidyl peptidase-IV (DPP-4) inhibitors (e.g., sitagliptin, alogliptin, linagliptin, vildagliptin, saxagliptin, teneligliptin, omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors, (e.g., avasimibe);

(11) HDL-raising drugs, (e.g., niacin and nicotinic acid receptor agonists, and extended-release versions thereof;

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, MR 1704, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501.

Other suitable active ingredients/pharmaceutical agents that may be administered in combination with a compound of the present invention, and either administered separately or in the same pharmaceutical composition, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, ATl-802, E3080, and the like; (26) carnitine palmitoyl transferase inhibitors such as ST 1327, and ST 1326, and the like; (27) Fructose 1,6-bisphosphohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3 (methylsulfonyl)propoxy)phenyl)phenyl)methoxy)-phenyl)iso, 5-(4-((3-(2-methyl-6-(3-hydroxypropoxy)pyridine-3-yl)-2-methylphenyl)methoxy)-phenyl)isothiazole-3-ol 1-oxide, and 5-[4-[[3-[4-(3-aminopropoxy)-2,6-dimethylphenyl]-phenyl]methoxy]phenyl]isothiazole-3-ol 1-oxide), and those disclosed in WO 11/078371.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin, atorvastatin or rosuvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705

(Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTCO179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), S8921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as taranabant, rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), O1691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate, clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552, 524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436, 272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone 13 agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mr1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, rosuvastatin, sitagliptin, metformin, sibutramine, orlistat, Qnexa, topiramate, naltrexone, bupriopion, phentermine, and losartan, losartan with hydrochlorothiazide.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2, 4'-piperidin]-6-yl}nicotinic acid; 1'-(8-methoxy-4-morpholin-4-yl-2-naphthoyl)-6-(1H-tetrazol-5-yl)spiro [chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof.

Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from Januvia, 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxyl phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4 (3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methylpropane-nitrile; and pharmaceutically acceptable salts thereof.

Suitable neurokinin-1 (NK-1) receptor antagonists may be favorably employed with the AMP-kinase activators of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention also provides a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The following Examples are provided to illustrate the invention and are not to be construed as limiting the invention in any manner. The scope of the invention is defined by the appended claims.

Methods of Synthesis of the Compounds of the Present Invention:

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

The compounds of the present invention can be prepared according to the procedures of the following Examples, using appropriate materials. The compounds illustrated in the examples are not, however, to be construed as forming the only genus that is considered as the invention. The Examples further illustrate details for the preparation of the compounds of the present invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

LIST OF ABBREVIATIONS

Ac is acetyl; ACN is acetonitrile; AcO is acetoxy; AcOH is acetic acid; AcONa is sodium acetate; Alk is alkyl; APCI is atmospheric pressure chemical ionization; $Ag_2CO_3$ is silver carbonate; aq or aq. is aqueous; Ar is aryl; br is broad; BrettPhos Precatalyst is chloro[2-(dicyclohexylphosphino)-3,6-dimethoxy-2',4',6'-triisopropyl-1,1'-biphenyl][2-(2-aminoethyl)phenyl]-palladium(II); bu is butyl; ° C. is degrees Celsius; $CH_2Cl_2$ is dichloromethane; $CCl_4$ is carbon tetrachloride; conc or conc. is concentrated; d is doublet; DAST is (diethylamino)sulfur trifluoride; DIAD is diisopropyl azodicarboxylate; DCM is dichloromethane; DMAP is 4-dimethylaminopyridine; DMF is N,N-dimethylformamide; DMSO is dimethylsulfoxide; dppf is 1,1'-bis(diphenyl-phosphino)ferrocene; ESI is electrospray ionization; EA or EtOAc is ethyl acetate; et is ethyl; EtOH is ethanol; g or gm is gram(s); h or hr or hrs is hour(s); HPLC is high pressure liquid chromatography; kg is kilogram(s); KHMDS is potassium hexamethyl disilazide; $K_2CO_3$ is potassium carbonate; KOAc is potassium acetate; L is liter; LiOH is lithium hydroxide; m is multiplet; mL or ml is milliliter; min or mins is minute(s); mol is mole(s); mmol is mmole(s); mg is milligram(s); M is molar; MCPBA, mCPBA or m-CPBA is meta-chloro-peroxybenzoic acid; me is methyl; MeOH is methyl alcohol; MgSO$_4$ is magnesium sulfate; MS is mass spectroscopy; MsCl or Ms-Cl is methane sulfonyl chloride or mesyl chloride; MTBE is methyl tert-butyl ether; N is normal; NaOH is sodium hydroxide; Na$_2$SO$_4$ is sodium sulfate; NBS is N-bromo succinamide; NIS is N-iodo succinamide; NMP is 1-methyl-2-pyrrolidinone; NMR is nuclear magnetic resonance spectroscopy; PE is petroleum ether; Pd(dppf)Cl$_2$ is [1,1'-bis(diphenyl-phosphino)ferrocene]-dichloro-palladium (II); Pd(dtbpf)Cl$_2$ is [1,1'-bis(di-tert-butylphosphino)-ferrocene]dichloro-palladium (II); PMB is para-methoxybenzyl; PMBCl is para-methoxybenzyl chloride; Pd(PPh$_3$)$_4$ is tetrakis triphenyl phosphine palladium; prep. TLC or prep-TLC, or preparative TCL is preparative thin layer chromatography; rt or r.t. or RT is room temperature; sat. is saturated; s is singlet; t is triplet; TEA is triethyl amine; THF is tetrahydrofuran; TFA is trifluoroacetic acid; TLC is thin-layer chromatography; TosCl is p-toluene sulfonyl chloride; t-BuOK is potassium tert-butoxide; and X-Phos Second Generation Precatalyst is chloro(2-dicyclohexylphosphino-2',4',6'-triisopropyl-1,1'-biphenyl)[2-(2'-amino-1,1'-biphenyl)]palladium(II), THF adduct.

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention. All temperatures are degrees Celsius unless otherwise noted.

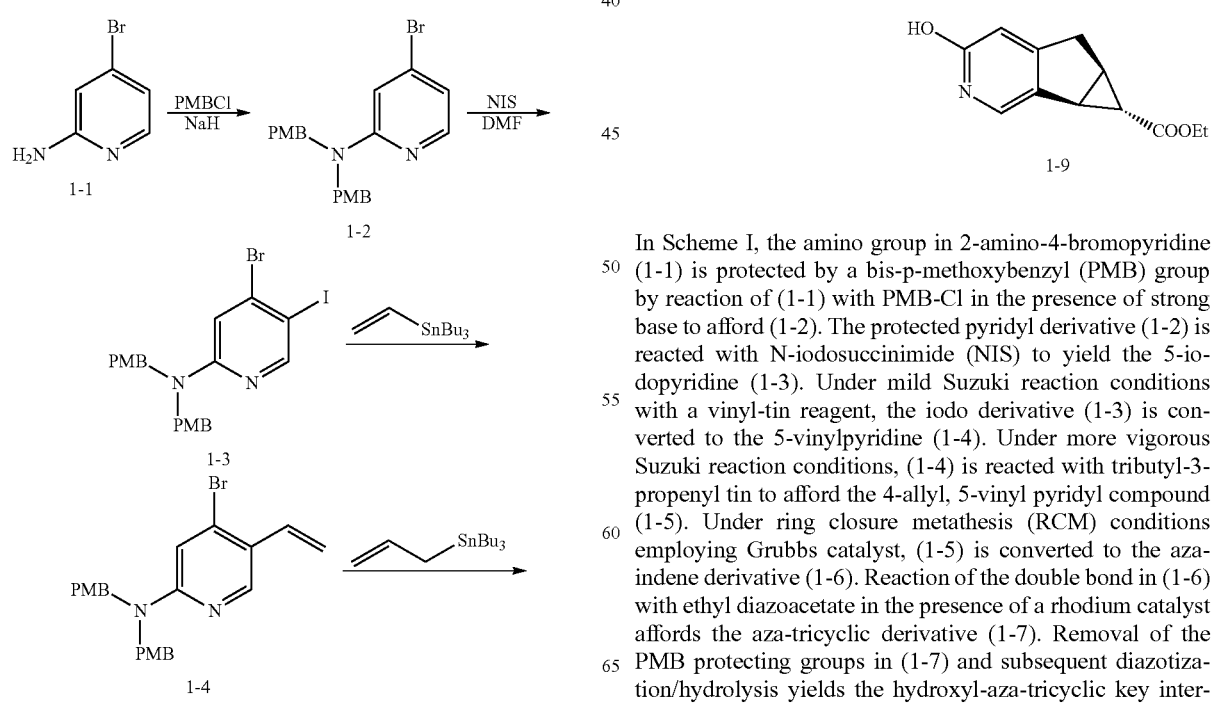

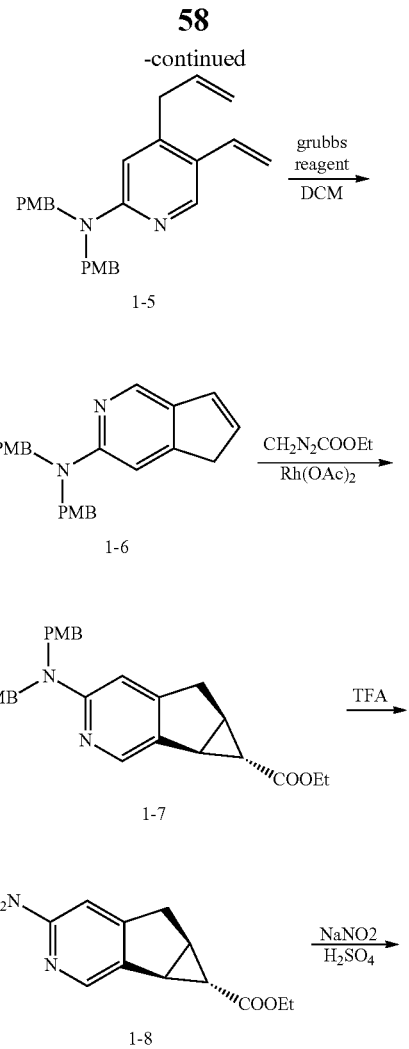

In Scheme I, the amino group in 2-amino-4-bromopyridine (1-1) is protected by a bis-p-methoxybenzyl (PMB) group by reaction of (1-1) with PMB-Cl in the presence of strong base to afford (1-2). The protected pyridyl derivative (1-2) is reacted with N-iodosuccinimide (NIS) to yield the 5-iodopyridine (1-3). Under mild Suzuki reaction conditions with a vinyl-tin reagent, the iodo derivative (1-3) is converted to the 5-vinylpyridine (1-4). Under more vigorous Suzuki reaction conditions, (1-4) is reacted with tributyl-3-propenyl tin to afford the 4-allyl, 5-vinyl pyridyl compound (1-5). Under ring closure metathesis (RCM) conditions employing Grubbs catalyst, (1-5) is converted to the aza-indene derivative (1-6). Reaction of the double bond in (1-6) with ethyl diazoacetate in the presence of a rhodium catalyst affords the aza-tricyclic derivative (1-7). Removal of the PMB protecting groups in (1-7) and subsequent diazotization/hydrolysis yields the hydroxyl-aza-tricyclic key intermediate (1-9).

Scheme II.

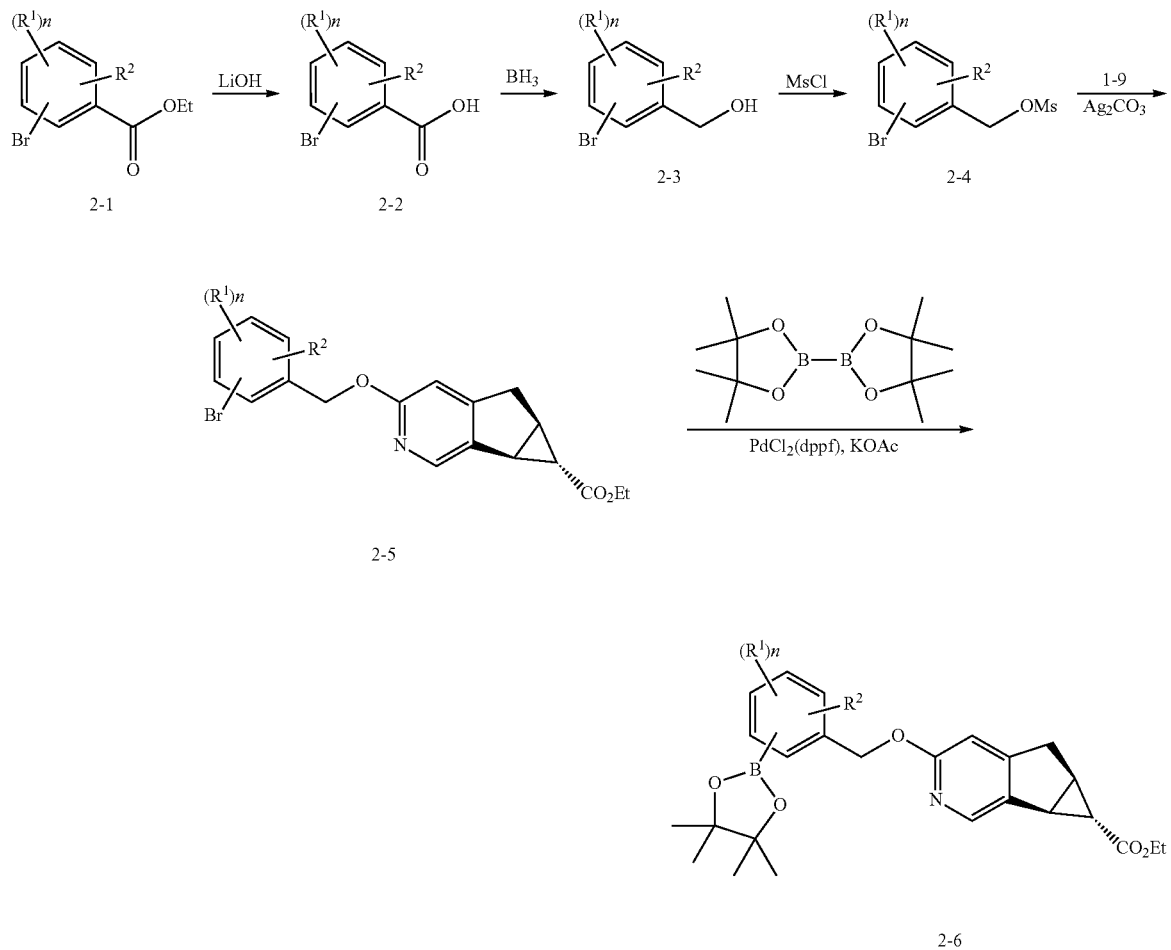

In Scheme II, bromoester (2-1) is hydrolysed to acid (2-2) with a base such as lithium hydroxide then reduced to alcohol (2-3) with a reducing agent such as borane. The benzylic alcohol (2-3) is then converted to mesylate (2-4) using mesyl chloride in the presence of a base such as triethylamine then reacted with key intermediate (1-9) in the presence of silver carbonate to yield bromo intermediate (2-5). This bromo intermediate (2-5) can be used as is or it can be converted into another intermediate, key boronate intermediate (2-6), using bis(pinacolato)diboron in the presence of a palladium catalyst such as Pd(dppf)Cl$_2$.

Scheme III.

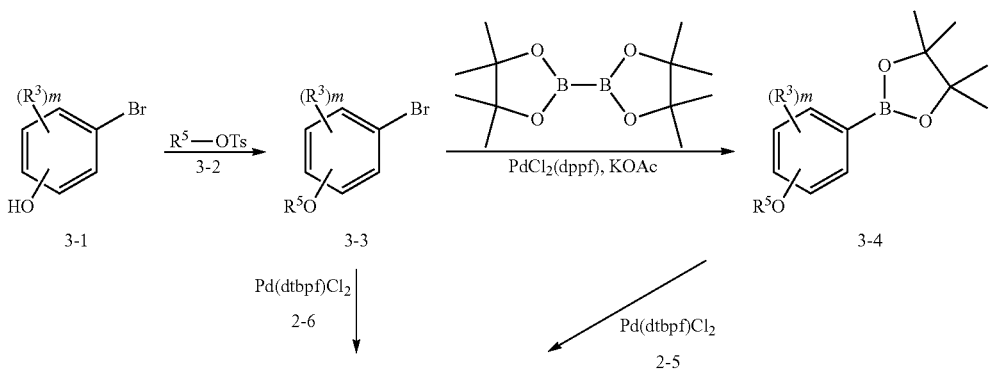

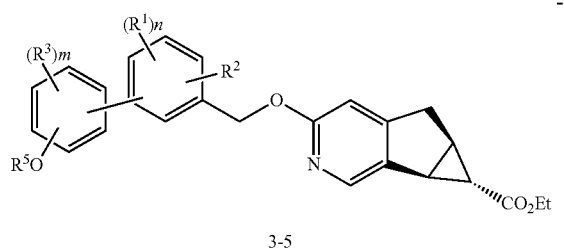

3-5

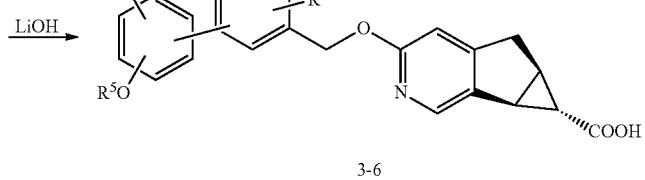

3-6

In Scheme III, bromophenol (3-1) is treated with tosylate (3-2) in the presence of a base such as $K_2CO_3$ to afford bromophenoxide (3-3). This intermediate (3-3) can be cross-coupled with key intermediate (2-6) under Suzuki conditions in the presence of a palladium catalyst such as $Pd(dtbpf)Cl_2$ to provide ester (3-5). Alternatively, intermediate (3-3) can be converted into boronate intermediate (3-4) using bis(pinacolato)diboron in the presence of a palladium catalyst such as $Pd(dppf)Cl_2$, and intermediate (3-4) can in turn be cross-coupled with key intermediate (2-5) under Suzuki conditions in the presence of a palladium catalyst such as $Pd(dtbpf)Cl_2$ to provide ester (3-5). Ester (3-5) is then hydrolysed using base such as sodium or lithium hydroxide to yield the compound of Formula (I).

Intermediate 1

4-Hydroxy-1,1a,6,6a-tetrahydro-3-aza-cyclopropa[a]indene-1-carboxylic acid ethyl ester

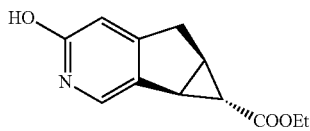 [SMILES: CCOC(=O)[C@H]1[C@@H]2Cc3cc(O)ncc3[C@@H]21]

Step A. (4-Bromo-pyridin-2-yl)-bis-(4-methoxy-benzyl)-amine

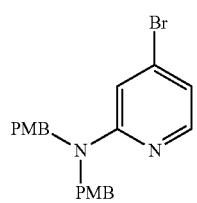

To a suspension of sodium hydride (60% in oil, 93 g, 2.32 mol) in DMF (1.8 L) was added 2-amino-4-bromopyridine (100 g, 0.58 mol) in DMF (500 mL) slowly at 0° C. Then the resulting mixture was allowed to stir at r.t. for 0.5 h under $N_2$ protection. PMBCl (227 g, 1.45 mol) was added to the reaction mixture and the reaction was maintained at 0-10° C. After addition, the mixture was allowed to stir at r.t. for 2 h. Then the mixture was poured into ice water carefully. The resulting solid precipitate was collected and washed with PE (150 mL×3), and the filtrate was concentrated to afford the title compound. $^1$HNMR (400 MHz, CDCl$_3$) δ: 7.99 (d, 1H, J=2.4 Hz), 7.12 (d, 4H, J=4.0 Hz), 6.84 (d, 4H, J=4.0 Hz), 6.71 (d, 1H, J=2.4 Hz), 6.64 (s, 1H), 4.66 (s, 4H), 3.79 (s, 6H).

Step B. (4-Bromo-5-iodo-pyridin-2-yl)-bis-(4-methoxy-benzyl)-amine

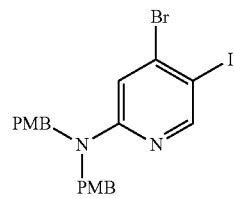

To a stirred solution of product from Step A (140 g, 0.34 mol) in DMF (2.8 L), was added NIS (115 g, 0.51 mmol) in several portions. The resulting mixture was heated to 40° C. and stirred for 24 h. The mixture was cooled and poured into ice water and stirred constantly. The resulting solid precipitate was collected and washed with PE (100 mL×3). The filtrate was concentrated under vacuum to afford the title compound. $^1$HNMR (400 MHz, CDCl$_3$) δ: 8.40 (s, 1H), 7.09 (d, 4H, J=4.0 Hz), 6.84-6.80 (m, 5H), 4.62 (s, 4H), 3.78 (s, 6H).

Step C. (4-Bromo-5-vinyl-pyridin-2-yl)-bis-(4-methoxy-benzyl)-amine

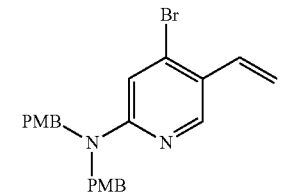

To a stirred solution of product from Step B (144 g, 267 mmol) in toluene (2 L), was added tributyl (vinyl) tin (85 g, 267 mmol), Pd(PPh$_3$)$_4$ (15.4 g, 13.4 mmol), KF (31 g, 534 mmol). The resulting mixture was heated to reflux for 18 h under $N_2$. The mixture was then cooled and KF (300 mL, 2 mol/L) was added. The reaction mixture was stirred for 20 minutes, and then filtered. The filtrate was separated, and the resulting organic layer was collected and evaporated under vacuum to give the crude product, which was purified by column chromatography on silica gel (eluting with PE:EA=20:1) to give the title compound. $^1$HNMR (400 MHz, CDCl$_3$) δ: 8.36 (s, 1H), 7.13 (d, 4H, J=4.0 Hz), 6.86-6.82 (m, 5H), 6.68 (s, 1H), 5.59 (d, 1H, J=8.0 Hz), 5.17 (d, 1H, J=6.4 Hz), 4.67 (s, 4H), 3.78 (s, 6H).

Step D. (4-Allyl-5-vinyl-pyridin-2-yl)-bis-(4-methoxy-benzyl)-amine

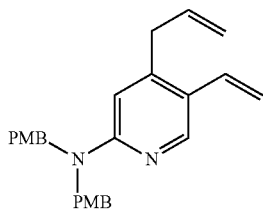

To a stirred solution of the product from Step C (90 g, 205 mmol) in THF (2 L), was added Cs$_2$CO$_3$ (134 g, 410 mmol), Pd(dppf)Cl$_2$ (7.5 g, 10.3 mmol), and allyltributyltin (136 g, 410 mmol). The resulting mixture was heated to reflux for 18 h under N$_2$. Then the mixture was cooled, and KF (300 mL, 2 mol/L) was added. The reaction mixture was stirred for 20 minutes. The mixture was filtered and the filtrate was separated. The resulting organic layer was collected and evaporated under vacuum to give the crude product, which was purified by chromatography over silica gel (eluting with PE:EA=30:1) to give the title compound. $^1$HNMR (400 MHz, CDCl$_3$) δ: 8.34 (s, 1H), 7.14 (d, 4H, J=4.0 Hz), 6.83 (d, 4H, J=4.0 Hz), 6.75 (dd, 1H, J=11.2 and 17.6 Hz), 6.29 (s, 1H), 5.86-5.79 (m, 1H), 5.53 (d, 2H, J=8.0 Hz), 5.14-4.96 (m, 3H), 4.69 (s, 4H), 3.79 (s, 6H), 3.27 (d, 2H, J=4.0 Hz). MS (ESI) m/e (M+H$^+$): 440.1

Step E: Bis-(4-methoxy-benzyl)-(5H-[2]pyrindin-3-yl)-amine

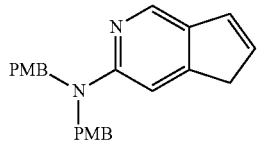

To a stirred solution of the product from Step D (55 g, 138 mmol) in DCM (700 mL), was added Grubbs reagent (II) (3.5 g, 4.14 mmol) in one portion. Then the resulting mixture was heated to reflux for 3 h under N$_2$. The mixture was then cooled and used in the next step directly. MS (ESI) m/e (M+H$^+$): 373.2.

Step F: 4-[Bis-(4-methoxy-benzyl)-amino]-1,1a,6,6a-tetrahydro-3-aza-cyclopropa[a]-indene-1-carboxylic acid ethyl ester

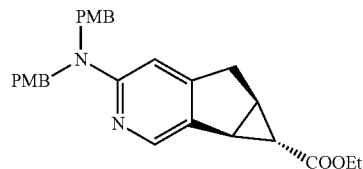

To a stirred solution of the product from Step E (52 g, 138 mmol) in DCM (0.7 L), was added Rh(OAc)$_2$ (1.6 g, 6.9 mmol) in one portion and the mixture was stirred for 15 minutes. Then ethyl diazoacetate (126 g, 1.1 mol) was added slowly to the mixture under gentle reflux conditions over 3 h. The resulting mixture was allowed to stir at r.t for 1 h. The reaction mixture was evaporated under vacuum to give the crude product, which was purified by column chromatography over silica gel (PE:EA=10:1) to give a cis-isomeric mixture of title compound as a racemate. The racemic mixture was separated by chiral column chromatography (eluting with PE:EA) to give the title compound. $^1$HNMR (400 MHz, CD$_3$OD) δ: 8.01 (s, 1H), 7.08 (d, 4H, J=4.0 Hz), 6.81. (d, 4H, J=4.0 Hz), 6.45 (s, 1H), 4.63 (s, 4H), 4.07 (dd, 2H, J=7.2 and 14.4 Hz), 3.74 (s, 6H), 3.13 (dd, 1H, J=6.0 and 12.0 Hz), 2.89 (d, 1H, J=8.0 Hz), 2.84 (d, 1H, J=2.4 Hz), 2.33-2.30 (m, 1H), 1.28-1.15 (m, 4H). MS (ESI) m/e (M+H$^+$): 459.1.

Step G: 4-Amino-1,1a,6,6a-tetrahydro-3-aza-cyclopropa[a]indene-1-carboxylic acid ethyl ester

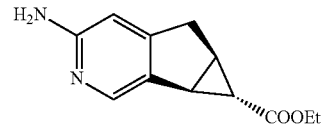 [SMILES: CCOC(=O)[C@H]1[C@@H]2Cc3cc(N)ncc3[C@@H]21]

To a stirred solution of product from Step F (19 g, 41.4 mmol) in DCM (130 mL), was added TFA (130 mL) in one portion. Then the resulting mixture was stirred at r.t overnight. LCMS showed reagent was consumed completely. The mixture was evaporated under vacuo to give the title compound, which was used in the next step directly. MS (ESI) m/e (M+H$^+$): 219.1.

Step H: 4-Hydroxy-1,1a,6,6a-tetrahydro-3-aza-cyclopropa[a]indene-1-carboxylic acid ethyl ester

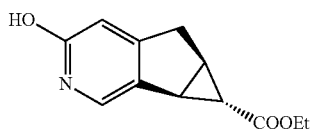 [SMILES: CCOC(=O)[C@H]1[C@@H]2Cc3cc(O)ncc3[C@@H]21]

To a stirred solution of product from Step G (23 g, crude) in H$_2$SO$_4$ (200 mL, 15%), was added NaNO$_2$ (14.4 g, 209 mmol) in portions at 0° C. Then the resulting mixture was allowed to stir at r.t for 2 h. LCMS showed reagent was consumed. The mixture was filtered, the solid filtered was purified by column (DCM:MeOH=20:1), the filtrate was basified with 2N NaOH to pH=5-6, then aqueous NaHCO$_3$ was added to adjust the pH=7, then extracted with DCM (300 mL×3), washed with brine, dried over Na$_2$SO$_4$, concentrated to afford the title compound. $^1$HNMR (400 MHz, CDCl$_3$) δ: 12.52 (s, 1H), 7.28 (s, 1H), 6.38. (s, 1H), 4.14 (dd, 2H, J=7.2 and 14.4 Hz), 3.18 (dd, 1H, J=6.0 and 12.0 Hz), 2.94 (d, 1H, J=8.8 Hz), 2.77 (dd, 1H, J=2.4 and 6.4 Hz), 2.43-2.39 (m, 1H), 1.28-1.25 (m, 4H). MS (ESI) m/e (M+H$^+$): 220 (M+H$^+$).

Intermediate 2

3-hydroxy-3-methylbutyl 4-methylbenzenesulfonate

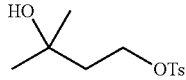

To a solution of 3-methylbutan-1,3-diol (10.0 g, 96.1 mmol) in DCM (100 mL) was added 4-methylbenzene-1-sulfonyl chloride (20.1 g, 106 mmol) and TEA (24.3 g, 240 mmol). The reaction mixture was stirred at room temperature for 12 h. Then the mixture was extracted with DCM (150 mL×3). The combined organic layers were washed with water and brine, dried over MgSO$_4$, and filtered. The filtrate was concentrated under reduced pressure. The resulting residue was purified by chromatography over silica gel (eluting with PE:EA=5:1) to give the title compound.

Intermediate 3

2-(3-hydroxyoxetan-3-yl)ethyl 4-methylbenzenesulfonate

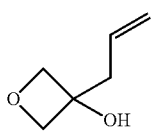

Step A: 3-allyloxetan-3-ol

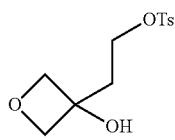

To a stirred solution of 3-oxetanone (10.0 g, 139 mmol) in THF (80 mL), was added allylmagnesium bromide (210 mL, 209 mmol) dropwise at −60° C. under N$_2$. Then the reaction mixture was stirred at −50 to −60° C. for 3 h. The reaction was neutralized with 2 N HCl, extracted with EtOAc (100 mL×3), and the combined organic layers were washed with brine, dried over Na$_2$SO$_4$, and concentrated to afford a crude product, which was purified by chromatography over silica gel (eluting with PE:EA=5:1) to give the title compound as a colorless oil. $^1$HNMR (400 MHz, CDCl$_3$) δ: 5.89-5.79 (m, 1H), 5.25 (s, 1H), 5.21 (d, J=2.4 Hz, 1H), 4.61 (d, J=6.7 Hz, 2H), 4.51 (d, J=7.0 Hz, 2H), 2.62 (d, J=3.6 Hz, 3H), 2.41 (s, 1H).

Step B: 2-(3-hydroxyoxetan-3-yl)acetaldehyde

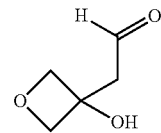

Ozone was bubbled into a solution of the product from Step A (2.00 g, 17.6 mmol) in DCM (30 mL) at −50° C. for 5 min After excess O$_3$ was purged by N$_2$ for 10 min, Me$_2$S (6.00 g, 100 mmol) was added and the reaction was stirred for 3 h at r.t. The reaction mixture was evaporated under vacuum to afford the title compound, which was used in the next step without purification.

Step C: 3-(2-hydroxyethyl)oxetan-3-ol

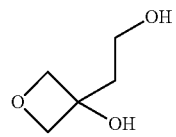

To a stirred suspension of LiAlH$_4$ (1.0 g, 26 mmol) in THF (50 mL), was added dropwise the product from Step B (3 g, crude) in THF (20 mL) at 0° C. The resulting mixture was stirred for 2 h at 0° C., then quenched by slow addition of H$_2$O (4 mL), followed by the addition of 15% aqueous NaOH (1 mL) After stirring at r.t for 30 min, the resulting solid was removed by filtration. The filtrate was then concentrated to dryness to give the title compound. $^1$HNMR (400 MHz, CDCl$_3$) δ: 4.64 (d, J=6.7 Hz, 2H), 4.49 (d, J=7.0 Hz, 2H), 4.08 (s, 1H), 3.92 (q, J=5.0 Hz, 2H), 2.29 (br. s., 1H), 2.14 (t, J=5.3 Hz, 2H).

Step D: 2-(3-hydroxyoxetan-3-yl)ethyl 4-methylbenzenesulfonate

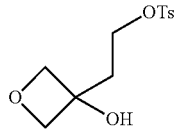 [SMILES: Cc1ccc(S(=O)(=O)OCCC2(O)COC2)cc1]

To a stirred suspension of the product from Step C (300 mg, 2.55 mmol) in DCM (4 mL) was added pyridine (0.95 mL, 10.2 mmol), TosCl (728 mg, 3.83 mmol) portionwise, and DMAP (30 mg). The resulting mixture was allowed to stir at r.t. overnight. The reaction mixture was then diluted with H$_2$O (10 mL), extracted with EtOAc (30 mL×3), and the organic layers were washed with brine, dried over Na$_2$SO$_4$, and concentrated to afford a crude product, which was purified by chromatography over silica gel (eluting with PE:EA=1:1) to give the title compound. $^1$HNMR (400 MHz, CDCl$_3$) δ: 7.77 (d, J=8.2 Hz, 2H), 7.35 (d, J=8.2 Hz, 2H), 4.62-4.48 (m, 4H), 4.22 (t, J=6.1 Hz, 2H), 2.95 (d, J=3.9 Hz, 1H), 2.45 (s, 3H), 2.21 (t, J=6.1 Hz, 2H).

Intermediate 4

4,4-difluoro-3-hydroxy-3-methyl-4-(phenylsulfonyl)butyl 4-methylbenzenesulfonate

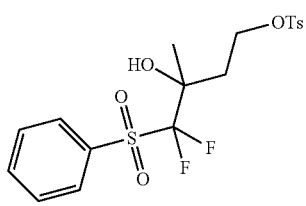 [SMILES: Cc1ccc(S(=O)(=O)OCCC(C)(O)C(F)(F)S(=O)(=O)c2ccccc2)cc1]

Step A: 4,4-difluoro-3-methyl-4-(phenylsulfonyl)butane-1,3-diol

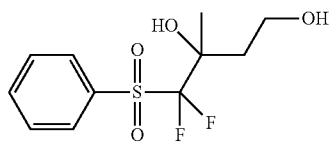 [SMILES: CC(O)(CCO)C(F)(F)S(=O)(=O)c1ccccc1]

To a solution of ((difluoromethyl)sulfonyl)benzene (10.0 g, 52.0 mol) and 4-hydroxybutan-2-one (6.87 g, 78.0 mol) under nitrogen in anhydrous THF (100 mL) at −78° C. was added dropwise KHMDS (78.0 mL, 78.0 mmol). The reaction mixture was stirred at −78° C. for 3 hours, and then quenched with water at −78° C. The reaction mixture was extracted with EtOAc (100 mL×3). The combined organic layers were washed with water and brine, dried over MgSO$_4$, and filtered. The filtrate was concentrated under reduced pressure to give the title compound, which was used without purification in the next step. MS (ESI) m/e (M+H$^+$): 281.

Step B: 4,4-difluoro-3-hydroxy-3-methyl-4-(phenylsulfonyl)butyl 4-methylbenzene sulfonate

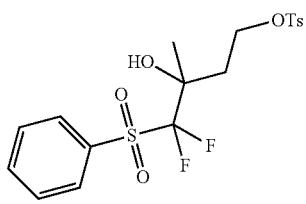 [SMILES: Cc1ccc(S(=O)(=O)OCCC(C)(O)C(F)(F)S(=O)(=O)c2ccccc2)cc1]

To a solution of the product from Step A (15.4 g, 55.0 mmol) in DCM (200 mL) was added Et$_3$N (16.7 g, 165 mmol) and 4-methylbenzene-1-sulfonyl chloride (10.5 g, 55.0 mmol) under nitrogen. The reaction mixture was stirred at room temperature for 16 h. Then the reaction mixture was diluted with DCM (150 mL), and the organic layer was washed with water and brine, dried over MgSO$_4$, and filtered. The filtrate was concentrated under reduced pressure. The resulting residue was purified by chromatography over silica gel (eluting with PE:EA=15:1) to give the title compound. MS (ESI) m/e (M+H$^+$): 435.

Intermediate 5

(5aR,6S,6aS)-ethyl 3-((5-bromo-2-fluoro-4-(trifluoromethyl)benzyl)oxy)-5,5a,6,6a-tetrahydrocyclopropa[4,5]cyclopenta[1,2-c]pyridine-6-carboxylate

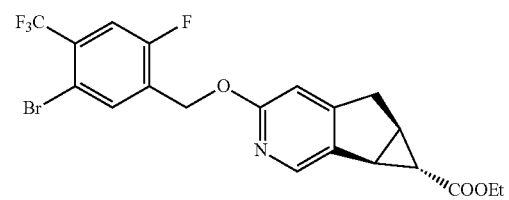 [SMILES: CCOC(=O)[C@H]1[C@@H]2Cc3cc(OCc4cc(Br)c(C(F)(F)F)cc4F)ncc3[C@@H]21]

Step A: methyl 2-fluoro-4-(trifluoromethyl)benzoate

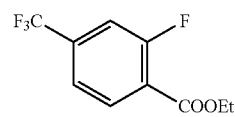 [SMILES: CCOC(=O)c1ccc(C(F)(F)F)cc1F]

To a mixture of 1-bromo-2-fluoro-4-(trifluoromethyl)benzene (5.0 g, 0.02 mol) in EtOH (10 mL) was added Pd(dppf)Cl$_2$ (1.46 g, 0.2 mmol) and AcONa (3.37 g, 0.041 mol), and the resulting mixture was stirred at 80° C. under an atmosphere of CO (50 psi) for 8 hours. The mixture was then filtrated and the filtrate was partitioned with ethyl acetate and water. The aqueous layer was separated and extracted with ethyl acetate twice. The combined organic layers were washed with brine, dried over anhydrous Na$_2$SO$_4$ and concentrated in vacuo. The resulting residue was purified by column chromatography on silica gel (eluting with PE:EA=10:1) to give the title compound. $^1$H NMR (400 MHz, CDCl$_3$) g: 8.04-8.08 (t, 1H, J=7.6 Hz), 7.49-7.47 (d, 1H, J=8.0 Hz), 7.43-7.40 (d, 1H, J=10.4 Hz), 4.44-4.40 (q, 2H, J=7.2 Hz), 1.43-1.38 (t, 3H, J=7.2 Hz).

Step B: ethyl 2-fluoro-5-nitro-4-(trifluoromethyl)benzoate

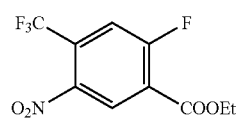

To a stirred solution of the product from Step A (120 g, 0.51 mol) in concentrated H$_2$SO$_4$ (0.5 L), was added dropwise fuming HNO$_3$ (50 ml) at 0° C. The resulting mixture was stirred at 25° C. for 1 h, then cooled and poured into ice water and stirred. The solid that precipitated was collected and washed with PE (100 mL×3). The filtrate was concentrated under vacuum to afford the title compound. $^1$HNMR (400 MHz, CDCl$_3$) δ: 8.54-8.45 (d, 1H, J=6.8 Hz), 7.63-7.60 (d, 1H, J=10.4 Hz), 4.48-4.43 (q, 2H, J=7.2 Hz), 1.55-1.39 (t, 3H, J=7.2 Hz).

Step C: ethyl 5-amino-2-fluoro-4-(trifluoromethyl)benzoate

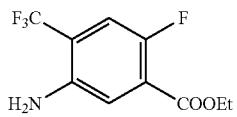

To a solution of the product from Step B (80 g, 0.28 mol) in MeOH (1 L) was added Pd/C (8 g). The mixture was degassed via vacuum and purged with $H_2$ several times, then the mixture was stirred under a $H_2$ balloon for 16 hours at room temperature. The mixture was filtered; and the filtrate was concentrated to give the title compound. MS (ESI) m/e (M+H$^+$): 273.1, 293.2.

Step D: ethyl 5-bromo-2-fluoro-4-(trifluoromethyl)benzoate

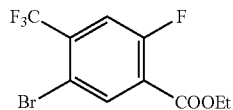

To a stirred solution of the product from Step C (60 g, 0.24 mol) in ACN (600 mL), was added $CuBr_2$ (59 g, 0.26 mol) and isopentyl nitrite (36 g, 0.31 mol). The resulting mixture was stirred at 25° C. for 18 h under $N_2$. The mixture was then cooled and filtered, and the filtrate was separated. The organic layer was collected and evaporated under vacuum to give a crude product, which was purified by column chromatography over silica gel (eluting with PE:EA=30:1) to give the title compound. $^1$HNMR (400 MHz, CDCl$_3$) δ: 8.24-8.05 (d, 1H, J=6.8 Hz), 7.53-7.50 (d, 1H, J=10.4 Hz), 4.48-4.43 (q, 2H, J=7.2 Hz), 1.45-1.39 (t, 3H, J=7.2 Hz).

Step E: 5-bromo-2-fluoro-4-(trifluoromethyl)benzoic acid

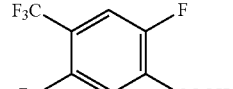

To a solution of the product from Step D (17.5 g, 55.7 mmol) in EtOH/$H_2O$ (200/20 mL) was added LiOH (12 g, 0.28 mol). The reaction mixture was stirred at room temperature for 18 h. Then HCl (2 mol/L) was added to the reaction to adjust the pH to 5. The reaction mixture was concentrated under vacuum to remove the EtOH, and the remaining mixture was extracted with EtOAc (50 mL×3). The combined organic layers were concentrated to afford the title compound.

Step F: (5-bromo-2-fluoro-4-(trifluoromethyl)phenyl)methanol

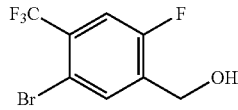

To a solution of the product from Step E (17.08 g, 59.7 mmol) in THF (170 mL) was added $BH_3(Me_2S)$ (18 mL) at 0° C. The reaction was stirred at 17-19° C. for 18 h. Then the reaction was quenched with MeOH at 0° C. The reaction mixture was concentrated and the resulting crude residue was purified by chromatography over silica gel (eluting with PE:EA=5:1) to give the title compound.

Step G: 5-bromo-2-fluoro-4-(trifluoromethyl)benzyl methanesulfonate

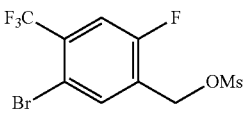 [SMILES: CS(=O)(=O)OCc1cc(Br)c(C(F)(F)F)cc1F]

To a solution of the product from Step F (4 g, 14.65 mmol) in DCM (20 ml) was added TEA (2.22 g, 22 mmol). The reaction mixture was cooled in an ice bath, then MsCl (1.5 g, 22 mmol) was added dropwise to the reaction. The reaction was stirred at 0° C. for 20 min, then water (30 mL) was added to the reaction mixture at 0° C. The resulting mixture was extracted with DCM (10 mL×3). The combined organic layers was dried over $Na_2SO_4$ and concentrated under vacuum to give the title compound.

Step H: (5aR,6S,6aS)-ethyl 3-((5-bromo-2-fluoro-4-(trifluoromethyl)benzyl)oxy)-5,5a,6,6a-tetrahydrocyclopropa[4,5]cyclopenta[1,2-c]pyridine-6-carboxylate

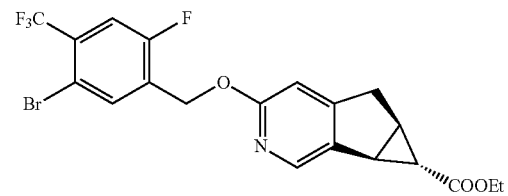 [SMILES: CCOC(=O)[C@H]1[C@@H]2Cc3cc(OCc4cc(Br)c(C(F)(F)F)cc4F)ncc3[C@@H]21]

To a solution of the product from Step G (5 g crude) in toluene (50 ml) were added Intermediate 1 (3.1 g, 14.1 mmol) and $Ag_2CO_3$ (11.66 g, 42.3 mmol). The reaction was stirred at 100° C. for 18 h. Then the reaction mixture was cooled to room temperature and filtered. The filtrate was concentrated in vacuo and the crude was purified by chromatography over silica gel (eluting with PE:EA=10:1) to give the title compound. $^1$HNMR (400 MHz, MeOH-d$_4$) δ: 8.05 (s, 1H), 7.81 (d, J=6.7 Hz, 1H), 7.39 (d, J=9.8 Hz, 1H), 6.64 (s, 1H), 5.41 (s, 2H), 4.13 (q, J=7.0 Hz, 2H), 3.23 (dd, J=6.3, 18.4 Hz, 1H), 3.00 (d, J=18.4 Hz, 1H), 2.91 (d, J=5.1 Hz, 1H), 2.48-2.40 (m, 1H), 1.25 (t, J=7.2 Hz, 3H), 1.22 (d, J=3.1 Hz, 1H). MS (ESI) m/e (M+H$^+$): 474, 476.

Intermediate 6

5aR,6S,6aS)-ethyl3-((2-fluoro-5-(4,4,5,5-tetramethyl-1,3,2-dioxaborolan-2-yl)-4-(trifluoromethyl)benzyl)oxy)-5,5a,6,6a-tetrahydrocyclopropa[4,5]cyclopenta[1,2-c]pyridine-6-carboxylate

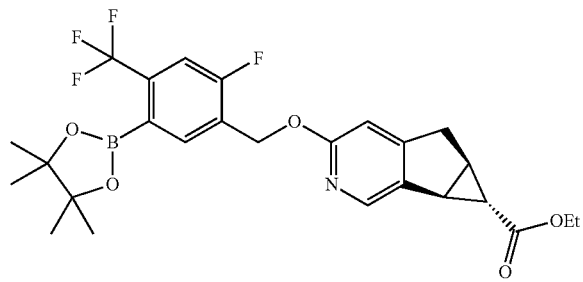 [SMILES: CCOC(=O)[C@H]1[C@@H]2Cc3cc(OCc4cc(B5OC(C)(C)C(C)(C)O5)c(C(F)(F)F)cc4F)ncc3[C@@H]21]

Bis(pinacolato)diboron (0.803 g, 3.16 mmol), potassium acetate (0.414 g, 4.22 mmol), Pd(dppf)Cl$_2$ (0.154 g, 0.211 mmol), and Intermediate 5 (1.00 g, 2.11 mmol) were dissolved in DMF (0.8 mL) and dioxane (2.5 mL), then placed in a sealed tube and heated in a microwave oven at 150° C. for 30 min. The reaction mixture was cooled and the solvent was evaporated under reduced pressure. The resulting residue was purified by column chromatography on silica gel (eluting with PE:EA=5:1) to give the title compound as a colorless gum. $^1$HNMR (400 MHz, CDCl$_3$) δ: 8.12-8.05 (m, 1H), 7.94-7.87 (m, 1H), 7.44-7.36 (m, 1H), 6.66-6.61 (m, 1H), 5.41 (s, 2H), 4.20-4.12 (m, 2H), 3.28-3.19 (m, 1H), 3.06-2.90 (m, 2H), 2.51-2.41 (m, 1H), 1.36 (s, 12H), 1.28 (t, J=6.3 Hz, 3H), 1.24-1.21 (m, 1H).

Intermediate 7

5aR,6S,6aS)-ethyl 3-((5-bromo-4-(difluoromethyl)-2-fluorobenzyl)oxy)-5,5a,6,6a-tetrahydro-cyclopropa[4,5]cyclopenta[1,2-c]pyridine-6-carboxylate

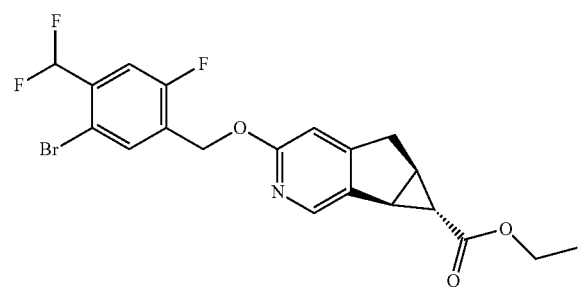 [SMILES: CCOC(=O)[C@H]1[C@@H]2Cc3cc(OCc4cc(Br)c(C(F)F)cc4F)ncc3[C@@H]21]

Step A: 5-bromo-2-fluoro-4-methylbenzoic acid

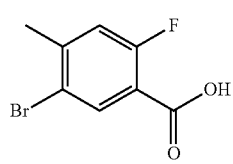

2-fluoro-4-methylbenzoic acid (10 g, 64.9 mmol) was added in portions to a mixture of bromine (145 g, 908 mmol) and iron (1.812 g, 32.4 mmol), and the reaction mixture was stirred in a sealed vial for 28 h. The reaction mixture was then poured into aqueous saturated sodium thiosulfate and extracted with ethyl acetate (50 ml×2). The combined ethyl acetate extracts were washed with brine, dried over magnesium sulfate and concentrated. The resulting residue was suspended in ethyl acetate and the insoluble impurity was filtered off. Then the filtrate was concentrated to dryness under vacuum to give the title compound as a yellow solid, which was used in the next step without further purification.

Step B: methyl 5-bromo-2-fluoro-4-methylbenzoate

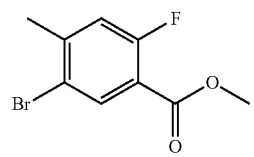

To a mixture of product from Step A (16 g, 68.7 mmol) in MeOH (20 ml) was added concentrated sulfuric acid (0.673 g, 6.87 mmol) at room temperature. The mixture was stirred at reflux overnight. After cooling down, the solvent was evaporated off to give a crude oil. The oil was purified by column chromatography over silica gel (eluting with PE:EA=20:1) to give the title compound as a colorless oil. $^1$HNMR (400 MHz, CDCl$_3$) δ: 8.09 (d, J=7.2 Hz, 1H), 7.04 (d, J=11.2 Hz, 1H), 3.93 (s, 3H), 2.43 (s, 3H).

Step C: methyl 5-bromo-4-(dibromomethyl)-2-fluorobenzoate

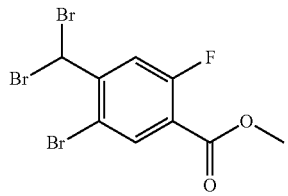

To a mixture of the product from Step 13 (1.6 g, 6.425 mmol) in CCl$_4$ (20 mL) was added NBS (3.46 g, 19.43 mmol) and benzoic peroxyanhydride (0.157 g, 0.648 mmol). The reaction mixture was stirred at 90° C. overnight. The mixture was then cooled and filtrated through a Celite™ pad and the insoluble solid was washed with PE twice. The combined organic layers were concentrated in vacuo to give a crude oil, which was purified by column chromatography over silica gel (eluting with PE:EA=20:1) to give the title compound as a light yellow oil. $^1$HNMR (400 MHz, CDCl$_3$) δ: 8.10 (d, J=7.0 Hz, 1H), 7.82 (d, J=11.2 Hz, 1H), 6.95 (s, 1H), 3.96 (s, 3H).

Step D: methyl 5-bromo-2-fluoro-4-formylbenzoate

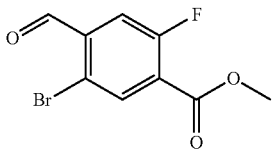

To a suspension of the product from Step C (2.5 g, 6.18 mmol) in THF (20 mL) and water (7 mL) was added AgNO₃ (3.15 g, 18.53 mmol). The reaction mixture was stirred at 80° C. for 2 hours. After cooling down, the mixture was filtrated through Celite™, washed with DCM, and the combined organic layers were concentrated in vacuo. The resulting residue was purified by flash chromatography over silica gel (eluting with PE/EA=10%) to give the title compound as a yellow solid, which was used in the next step without further purification.

Step E: methyl 5-bromo-4-(difluoromethyl)-2-fluorobenzoate

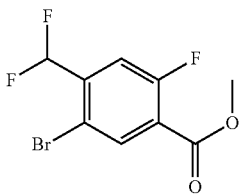

To a solution of the product from Step D (0.5 g, 1.915 mmol) in DCM (5.0 mL), in an ice bath, was added DAST (0.72 g, 4.8 mmol). The reaction mixture was allowed to warm to r.t. and stirred at room temperature overnight. The reaction was then poured into ice water, and extracted with DCM (10 mL×3). The combined organic layers were washed with brine, dried over Na₂SO₄ and concentrated in vacuo to give the title compound as a light yellow oil, which was used in the next step without further purification. ¹HNMR (400 MHz, CDCl₃) δ: 8.18 (d, J=6.6 Hz, 1H), 7.47 (d, J=10 Hz, 1H), 6.85 (m, 1H), 3.95 (s, 3H).

Step F: (5-bromo-4-(difluoromethyl)-2-fluorophenyl)methanol

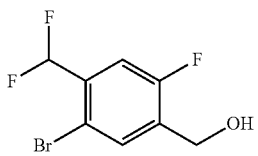 [SMILES: OCc1cc(Br)c(C(F)F)cc1F]

To a mixture of the product from Step E (0.3 g, 1.060 mmol) and NaBH₄ (0.120 g, 3.18 mmol) in THF (3.0 mL), in an ice bath, was added MeOH (0.1 mL) The reaction mixture was stirred at 60° C. for 2 hrs, and then partitioned between H₂O and EtOAc. The aqueous layer was separated and extracted by EtOAc twice. The combined organic layers were washed with brine, dried over Na₂SO₄, and concentrated in vacuo to give a crude oil, which was purified by chromatography over silica gel (eluting with PE:EA=5:1) to give the title compound as a light yellow oil.

Step G: 1-bromo-5-(bromomethyl)-2-(difluoromethyl)-4-fluorobenzene

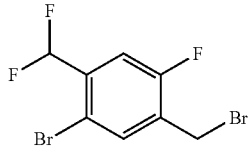

To a solution of the product from Step F (200 mg, 0.784 mmol) in DCM (3 mL) at 0° C. was added tribromophosphine (212 mg, 0.784 mmol). The mixture was stirred at 0° C. for 1 hour. The reaction was then quenched with H₂O and extracted with DCM twice. The combined organic layers were washed with brine, dried over Na₂SO₄ and concentrated in vacuo to give the title compound as a colorless oil, which was used in the next step without purification.

Step H: (5aR,6S,6aS)-ethyl 3-((5-bromo-4-(difluoromethyl)-2-fluorobenzyl)oxy)-5,5a,6,6a-tetrahydrocyclopropa[4,5]cyclopenta[1,2-c]pyridine-6-carboxylate

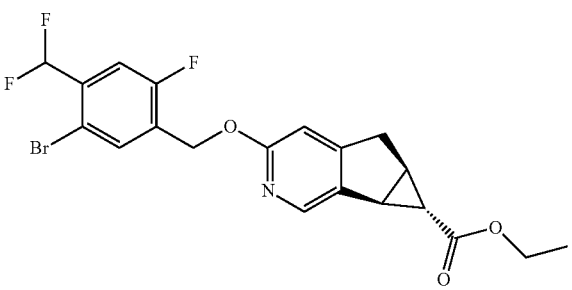 [SMILES: CCOC(=O)[C@H]1[C@@H]2Cc3cc(OCc4cc(Br)c(C(F)F)cc4F)ncc3[C@@H]21]

To a solution of the product from Step G (130 mg, 0.409 mmol) in toluene (2 mL), was added Ag₂CO₃ (169 mg, 0.613 mmol) and Intermediate 1 (98 mg, 0.409 mmol). The mixture was stirred at 120° C. for 4 hours. Then the reaction mixture was filtrated through a Celite™ pad and washed with DCM. The combined filtrates were concentrated in vacuo to give a residue, which was purified by chromatography on silica gel (eluting with PE:EA=5:1) to give the title compound as a colorless oil. MS (ESI) m/e (M+H⁺): 456.2.

Intermediate 8

3-(methylsulfonyl)propyl 4-methylbenzenesulfonate

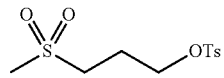

Step A: 3-(methylthio)propyl 4-methylbenzenesulfonate

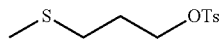 [SMILES: CSCCCOS(=O)(=O)c1ccc(C)cc1]

To a solution of the 3-(methylthio)propan-1-ol (50 g, 0.47 mol) and triethylamine (95 g, 0.94 mol) in DCM (500 mL) was added TsCl (90 g, 0.47 mol) portionwise at 0° C. After completion of addition, the reaction mixture was allowed to warm to room temperature slowly and stirred at this temperature for 16 h. Then the reaction was quenched with 1N HCl to adjust the pH to pH 7-8, and the mixture was extracted three times with EtOAc. The combined organic layers were washed with brine, dried over Na$_2$SO$_4$, filtered and concentrated in vacuo to give a residue which was purified by chromatography over silica gel (eluting with PE:EA=5:1) to afford the title compound.

Step B: 3-(methylsulfonyl)propyl 4-methylbenzenesulfonate

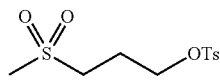 [SMILES: Cc1ccc(S(=O)(=O)OCCCS(C)(=O)=O)cc1]

To a solution of product from Step A (35 g, 135 mmol) in dry DCM (400 mL) in an ice-bath was added MCPBA (46.5 g, 270 mmol) portionwise. The resulting mixture was stirred at 0° C. for 1 h, and then warmed to the room temperature and stirred for 20 h. The reaction was quenched by addition of aqueous solution of NaHSO$_3$ and the DCM layer was washed with Na$_2$CO$_3$ (aq.), water and brine, respectively, and concentrated to afford a residue, which was purified by chromatography on silica gel (eluting with PE:EA=3:1) to give the title compound.

Intermediate 9

(5aR,6S,6aS)-tert-butyl 3-hydroxy-5,5a,6,6a-tetrahydrocyclopropa[4,5]cyclopenta[1,2-c]pyridine-6-carboxylate

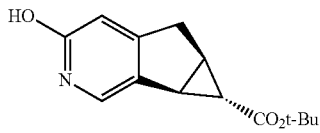

Step A: (E)-methyl 5-(3-(tert-butoxy)-3-oxoprop-1-en-1-yl)-2-chloroisonicotinate

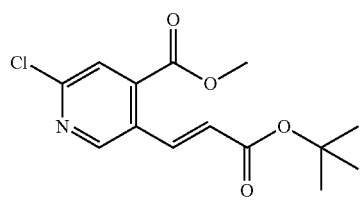 [SMILES: COC(=O)c1cc(Cl)ncc1/C=C/C(=O)OC(C)(C)C]

To a solution of 5-bromo-2-chloroisonicotinic acid (Combi-Blocks, 100 g, 423 mmol) in THF (200 mL) and toluene (800 mL) was added DMF (1.6 mL, 21.15 mmol). To the resulting slurry was added slowly oxalyl chloride (47 mL, 529 mmol). The reaction was stirred over the weekend at room temperature. Then MeOH (100 mL) was added slowly while cooling in a water bath. After 2 h at room temperature, aqueous K$_2$HPO$_4$ (1 M, 423 mL, 423 mmol) was added slowly while cooling in a water bath. The layers were separated and the aqueous layer was extracted with toluene (1×250 mL) The combined organic layers were filtered through Solca-Floc™ cellulose, then washed with water (1×200 mL), dried over MgSO$_4$ and concentrated in vacuo to give the crude methyl ester intermediate. To the methyl ester intermediate in toluene (2 L) was added chloro[tris(2-methylphenyl)phosphine][2-(2'-amino-1,1'-biphenyl)]palladium(II) (2.6 g, 4.23 mmol, 1%) and N,N-dicyclohexylmethylamine (226 mL, 1057 mmol). The reaction was degassed for 1 h, then t-butyl acrylate was added in a single portion and the reaction mixture was heated to 80° C. overnight. Then additional chloro[tris(2-methylphenyl)phosphine][2-(2'-amino-1,1'-biphenyl)]palladium(II) (1.3 g, 2.12 mmol, 0.5%) was added and the reaction was heated at 80° C. for 3 h. The reaction mixture was then cooled to room temperature and quenched with water (500 mL) The organic layer was separated, washed with saturated brine (1×500 ml), then filtered through a plug of silica gel (150 g) and rinsed with 20% EtOAc in hexanes. The filtrate was concentrated in vacuo to give a crude oil, which was recrystallized from EtOAc in hexane (1:1) at −10° C. to provide the title compound. MS (ESI) m/e (M+H$^+$): 242.2.

Step B: (E)-5-(3-(tert-butoxy)-3-oxoprop-1-en-1-yl)-2-chloroisonicotinic acid

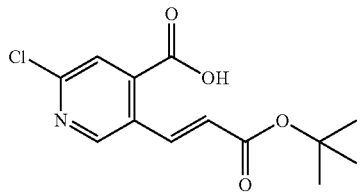 [SMILES: CC(C)(C)OC(=O)/C=C/c1cnc(Cl)cc1C(=O)O]

To a solution of (E)-methyl 5-(3-(tert-butoxy)-3-oxoprop-1-en-1-yl)-2-chloroisonicotinate (1 g, 3.36 mmol) in THF (10 ml) was added a solution of lithium hydroxide hydrate (0.155 g, 3.69 mmol) in water (2 ml), and the reaction was stirred at room temperature overnight. The reaction was then concentrated in vacuo and the resulting residue was diluted with 5 mL water, and slowly acidified with ice-cold 1N HCl solution (4.03 mL) The resulting white solid was filtered and dried under high vacuum to provide the title compound. MS (ESI) m/e (M+H$^+$): 284.2.

Step C: (E)-tert-butyl 3-(6-chloro-4-((E)-2-chloro-2-hydrazonoacetyl)pyridin-3-yl)acrylate

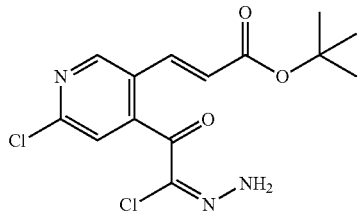 [SMILES: CC(C)(C)OC(=O)/C=C/c1cnc(Cl)cc1C(=O)/C(Cl)=N\N]

DMF (25 μl, 0.323 mmol) was added to a suspension of (E)-5-(3-(tert-butoxy)-3-oxoprop-1-en-1-yl)-2-chloroisonicotinic acid (1.73 g, 6.10 mmol) in dichloromethane (55 mL) and the reaction mixture was stirred at room temperature for 1 hour. The reaction mixture was then concentrated in vacuo, and co-evaporated with 1,2-dichloroethane. Then DCM (24 ml) was added to the resulting residue, and the resulting solution was added to a solution of (isocyanoimino)-triphenylphosphorane (2.77 g, 9.15 mmol) in DCM (14 mL) over 10 min. The reaction mixture was stirred at room temperature for 2 hours. Then water (6.6 ml, 366 mmol) was added and the mixture was stirred at room temperature overnight. Then the organic layer was separated, dried over MgSO₄ and concentrated in vacuo to provide a residue, which was purified by column chromatography over silica gel (eluting with EtOAc:hexanes=0:100 to 30:70) to give the title compound. MS (ESI) m/e (M+H$^+$): 344, 346, 348.

Step D: (E)-tert-butyl 3-(6-chloro-4-(2-diazoacetyl)pyridin-3-yl)acrylate

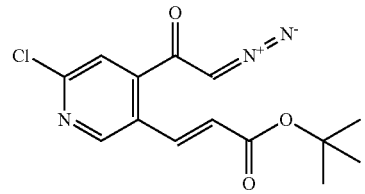 [SMILES: CC(C)(C)OC(=O)/C=C/c1cnc(Cl)cc1C(=O)C=[N+]=[N-]]

Anhydrous zinc bromide (325 mg, 1.443 mmol) was added to a solution of compound (E)-tert-butyl 3-(6-chloro-4-((E)-2-chloro-2-hydrazonoacetyl)pyridin-3-yl)acrylate (2.09 g, 6.07 mmol) in DCM (20 ml), followed by the dropwise addition of diisopropylethylamine (1.2 ml, 8.42 mmol). The reaction was stirred at room temperature for 1 hour, and then diluted with EtOAc. The organic layer was washed with 1% ethylenediamine tetraacetic acid tetrasodium salt, dried over anhydrous MgSO₄, and concentrated in vacuo. The resulting crude residue was purified by column chromatography over silica gel (eluting with EtOAc:hexanes=0:100 to 30:70) to give the title compound. MS (ESI) m/e (M+H$^+$): 308, 310.

Step E: (5aR,6R,6aS)-tert-butyl 3-chloro-5-oxo-5,5a,6,6a-tetrahydrocyclopropa-[4,5]cyclopenta-[1,2-c]pyridine-6-carboxylate

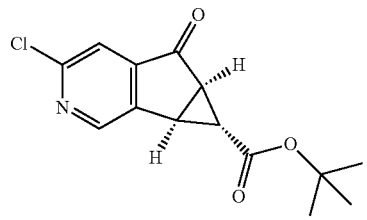 [SMILES: CC(C)(C)OC(=O)[C@H]1[C@@H]2C(=O)c3cc(Cl)ncc3[C@H]12]

A solution of 2,2-bis((S)-4-phenyl-4,5-dihydrooxazol-2-yl)acetonitrile (5.17 mg, 0.016 mmol), copper(I)trifluoromethanesulfonate toluene complex (3.36 mg, 6.50 μmol) and 2,6-di-tert-butylpyridine (29.2 μl, 0.130 mmol) in THF (1 mL) was warmed to 25° C., then (E)-tert-butyl 3-(6-chloro-4-(2-diazoacetyl)pyridin-3-yl)acrylate (400 mg, 1.300 mmol) in THF (3 mL) was added dropwise over 5 min. After 2.5 hours, the reaction mixture was diluted with EtOAc (3 mL) and MTBE (3 mL), washed with 0.5 M aqueous citric acid (6 mL), and concentrated in vacuo to provide a residue. The residue was purified by chromatography over silica gel (eluting with EtOAc:hexanes=0:100 to 30:70) to provide the title compound. The ee of the title compound was upgraded to 95% by dissolution in EtOAc (6 mL/g) and removal of the racemate by filtration. MS (ESI) m/e (M+H$^+$): 267.1.

Step F: (5aR,6S,6aS)-tert-butyl 3-chloro-5,5a,6,6a-tetrahydrocyclopropa[4,5]cyclopenta-[1,2-c]pyridine-6-carboxylate

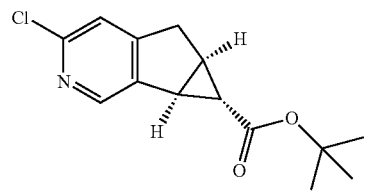 [SMILES: CC(C)(C)OC(=O)[C@H]1[C@@H]2Cc3cc(Cl)ncc3[C@@H]21]

Sodium borohydride (1.6 mg, 0.071 mmol) was added to a solution of (5aR,6R,6aS)-tert-butyl 3-chloro-5-oxo-5,5a,6,6a-tetrahydrocyclopropa[4,5]cyclopenta-[1,2-c]pyridine-6-carboxylate (20 mg, 0.071 mmol) in MeOH (0.4 mL) at 0° C. After 30 minutes, the reaction was quenched with saturated aqueous NH₄Cl and concentrated in vacuo. The resulting residue was re-dissolved in MTBE and washed once with water. The organic layer was separated, dried over MgSO₄ and concentrated in vacuo to give the alcohol intermediate. The alcohol intermediate was dissolved in THF (400 μL) and treated with trifluoroacetic anhydride (2 equiv, 0.142 mmol) for 30 minutes. The reaction was then cooled to 0° C., and concentrated aqueous HCl (5 equiv, 0.355 mmol) was added, followed by the portionwise addition of zinc dust (9.3 mg, 0.142 mmol) over 5 minutes. After stirring for 15 minutes, the reaction was diluted with water and extracted with MTBE twice. The combined organic layers were dried over MgSO₄ and concentrated in vacuo to give a residue, which was purified by column chromatography over silica gel (eluting with EtOAc:hexanes=10:90 to 20:80) to provide the title compound. $^1$H NMR (400 MHz, CDCl₃): δ 8.27 (s, 1H), 7.05 (s, 1H), 3.18 (dd, J=6.35 Hz, 12.2 Hz, 1H), 2.97 (d, J=18.5 Hz, 1H), 2.83 (d, J=6.35 Hz, 1H), 2.37 (m, 1H), 1.39 (s, 9H), 1.09 (br.s, 1H). MS (ESI) m/e (M+H$^+$): 280.1.

Step G: (5aR,6S,6aS)-tert-butyl 3-(2-(trimethylsilyl)ethoxy)-5,5a,6,6a-tetrahydrocyclopropa[4,5]cyclopenta[1,2-c]pyridine-6-carboxylate

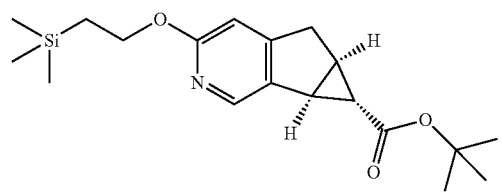 [SMILES: CC(C)(C)OC(=O)[C@H]1[C@@H]2Cc3cc(OCC[Si](C)(C)C)ncc3[C@@H]21]

To (5aR,6S,6aS)-tert-butyl 3-chloro-5,5a,6,6a-tetrahydrocyclopropa[4,5]cyclopenta[1,2-c]pyridine-6-carboxylate (0.5 g, 1.882 mmol), cesium carbonate (1.533 g, 4.70 mmol), and BrettPhos Precatalyst (0.075 g, 0.094 mmol) in a vial under nitrogen was added toluene (5 ml) and water (0.102 ml, 5.64 mmol). The reaction was degassed with bubbling nitrogen for 5 min, then 2-(trimethylsilyl)ethanol (0.405 ml, 2.82 mmol) was added and the reaction was stirred at 80° C. for 16 hours. Then water (10 mL) and EtOAc (30 ml) were added and the aqueous layer was separated and extracted with EtOAc twice. The organic layers were combined and washed with brine, dried over anhydrous Na$_2$SO$_4$, filtered, and concentrated in vacuo to give the title compound, which was used in the next step without further purification.

Step H: (5aR,6S,6aS)-tert-butyl 3-hydroxy-5,5a,6,6a-tetrahydrocyclopropa[4,5]-cyclopenta[1,2-c]pyridine-6-carboxylate

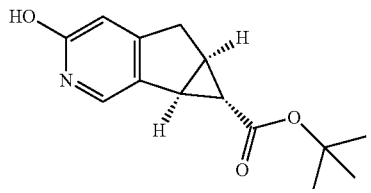 [SMILES: CC(C)(C)OC(=O)[C@H]1[C@@H]2Cc3cc(O)ncc3[C@@H]21]

To a solution of (5aR,6S,6aS)-tert-butyl 3-(2-(trimethylsilyl)ethoxy)-5,5a,6,6a-tetrahydro-cyclopropa[4,5]cyclopenta[1,2-c]pyridine-6-carboxylate (200 mg, 0.575 mmol) in acetonitrile (5 ml) was added water (5 ml), followed by phosphoric acid (0.146 ml, 2.014 mmol). The reaction was stirred at room temperature for 19.5 h, then concentrated in vacuo. The resulting residue was diluted with water and extracted with dichloromethane. The combined organic layers were washed with brine, dried over Na$_2$SO$_4$, filtered, and the filtrate solvent was evaporated in vacuo to give the title compound. $^1$H NMR (400 MHz, CD3CL): 6: ppm 7.26 (s, 1H), 6.38 (s, 1H), 3.14-3.24 (m, J=18.39, 6.26 Hz, 1H), 2.95-2.91 (m, 1H), 2.70-2.69 (d, J=5.1 Hz, 1H), 2.32-2.31 (m, 1H), 0.83 (br. s., 1H). MS (ESI) m/e (M+H$^+$): 248.1.

Intermediate 10

(5aR,6S,6aS)-tert-butyl 3-((2-fluoro-5-(4,4,5,5-tetramethyl-1,3,2-dioxaborolan-2-yl)-4-(trifluoromethyl)benzyl)oxy)-5,5a,6,6a-tetrahydrocyclopropa[4,5]cyclopenta[1,2-c]pyridine-6-carboxylate

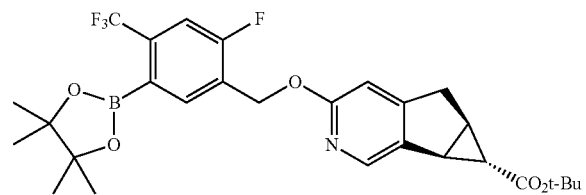 [SMILES: CC(C)(C)OC(=O)[C@H]1[C@@H]2Cc3cc(OCc4cc(B5OC(C)(C)C(C)(C)O5)c(C(F)(F)F)cc4F)ncc3[C@@H]21]

Intermediate 10 was prepared according to a procedure similar to the procedure of Intermediate 6 starting from the appropriate starting materials and using the appropriate reagents. $^1$H NMR (400 MHz, CDCl$_3$) δ: 8.03-8.12 (m, 1H), 7.81-7.93 (m, J=7.43 Hz, 1H), 7.31-7.44 (m, J=10.17 Hz, 1H), 6.51-6.65 (m, 1H), 5.38 (s, 2H), 3.14-3.24 (m, J=18.39, 6.26 Hz, 1H), 2.93-3.05 (m, J=18.39 Hz, 1H), 2.80-2.88 (m, J=5.09 Hz, 1H), 2.30-2.43 (m, 1H), 1.57 (s, 6H), 1.34 (s, 12H), 1.12 (br. s., 1H). MS (ESI) m/e (M+H$^+$): 549.8.

Intermediate 11

(5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydrocyclopropa[4,5]cyclopenta[1,2-c]pyridine-6-carboxylate

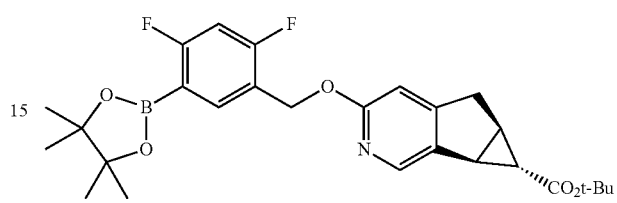

Step A: 5-Bromo-2,4-difluoro-benzoic acid

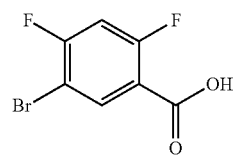 [SMILES: O=C(O)c1cc(Br)c(F)cc1F]

To a stirred solution of 2,4-difluorobenzoic acid (40 g, 0.26 mol) in concentrated H$_2$SO$_4$/TFA (1:5, 600 mL) at 0° C. was added NBS (45 g, 0.26 mmol) in portions. The resulting mixture was heated at 60° C. overnight, then the reaction was cooled to room temperature and most of the TFA was removed by evaporation. The resulting residue was carefully partitioned between EtOAc and water. The aqueous layer was separated and extracted with EtOAc twice. The combined organic layers were washed with brine, dried over anhydrous Na$_2$SO$_4$, and concentrated to give the crude product. The crude product was suspended in water and PE. The resulting solid was collected by filtration, and then re-crystallized from ethanol to give the title compound. $^1$H NMR (400 MHz, CDCl$_3$) δ: 7.02 (dd, J=9.78, 8.61 Hz, 1H), 8.28 (t, J=7.63 Hz, 1H).

Step B: (5-Bromo-2,4-difluoro-phenyl)-methanol

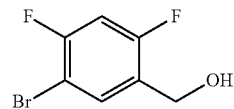

To a solution of 5-bromo-2,4-difluoro-benzoic acid (45.2 g, 190 mmol) in anhydrous THF (500 mL) cooled in an ice-bath was added (CH$_3$)$_2$S BH$_3$ (57 mL, 570 mmol). The resulting mixture was allowed to stir at room temperature overnight. Then methanol (500 mL) was carefully added to quench the reaction, and the mixture was stirred at 60° C. for 1 h. The mixture was then acidified with HCl (1N) to pH-5 and extracted with EtOAc twice. The combined organic layers were washed with brine, dried over anhydrous Na$_2$SO$_4$ and concentrated. The resulting residue was purified via silica gel chromatography (PE/EtOAc=8/1) to give the title compound. 1H NMR (400 MHz, CDCl$_3$) δ: 4.77 (br. s., 2H), 6.95 (t, J=8.78 Hz, 1H), 7.71 (t, J=7.53 Hz, 1H).

Step C:
1-Bromo-5-bromomethyl-2,4-difluoro-benzene

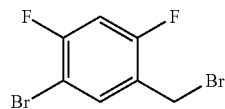

To a solution of (5-bromo-2,4-difluoro-phenyl)-methanol (35.2 g, 158 mmol) in anhydrous DCM (800 mL) cooled in an ice-bath was added PBr$_3$ (42.7 g, 157.8 mmol) dropwise. The reaction mixture was stirred at 0° C. for 1 h and at room temperature for 3 h. Then the reaction was quenched with water, and the aqueous layer was extracted with DCM twice. The combined organic layers were washed with brine, dried over anhydrous Na$_2$SO$_4$ and concentrated. The resulting residue was purified by column chromatography on silica gel (PE/EtOAc=50/1) to afford the title compound. $^1$H NMR (400 MHz, CDCl$_3$) δ: 4.43 (s, 2H), 6.92 (s, 1H), 7.60 (t, J=7.43 Hz, 1H).

Step D: (5aR,6S,6aS)-tert-butyl 3-((5-bromo-2,4-difluorobenzyl)oxy)-5,5a,6,6a-tetrahydrocyclopropa[4,5]cyclopenta[1,2-c]pyridine-6-carboxylate

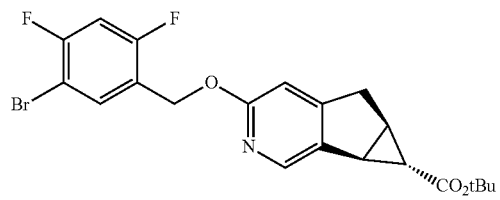 [SMILES: CC(C)(C)OC(=O)[C@H]1[C@@H]2Cc3cc(OCc4cc(Br)c(F)cc4F)ncc3[C@@H]21]

A mixture of 1-bromo-5-bromomethyl-2,4-difluoro-benzene (26.3 g, 77.4 mmol), Intermediate 4 (19.1 g, 77.4 mmol) and Ag$_2$CO$_3$ (64 g, 232 mmol) in dry toluene (600 mL) was heated at 110° C. for 12 h under a N$_2$ atmosphere. Then the reaction mixture was cooled to room temperature, diluted with DCM (500 mL), and the resulting precipitate was filtered off. The filtrate was concentrated and the resulting residue was purified by column chromatography on silica gel (PE/EtOAc=10/1 to 5/1) to give the title compound. $^1$H NMR (400 MHz, CDCl$_3$) δ: 1.16 (br. s., 1H), 1.47 (s, 9H), 1.57 (s, 1H), 2.37-2.41 (m, 1H), 2.87 (d, J=5.09 Hz, 1H), 2.98-3.03 (m, 1H), 3.22 (dd, J=18.39, 6.26 Hz, 1H), 5.35 (s, 2H) 6.61 (s, 1H), 6.92 (t, J=8.80 Hz, 1H), 7.67-7.74 (m, 1H), 8.09 (s, 1H). MS (ESI) m/e (M+H$^+$): 452.3/454.3.

Step E: (5aR,6S,6aS)-tert-butyl 3-((2,4-difluoro-5-(4,4,5,5-tetramethyl-1,3,2-dioxaborolan-2-yl)benzyl)oxy)-5,5a,6,6a-tetrahydrocyclopropa[4,5]cyclopenta[1,2-c]pyridine-6-carboxylate

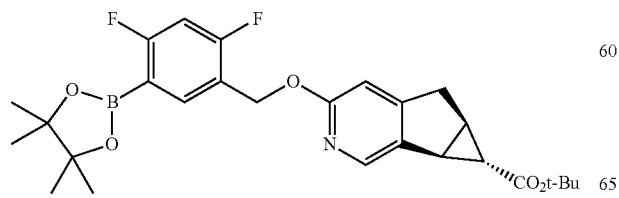

A mixture of (5aR,6S,6aS)-tert-butyl 3-((5-bromo-2,4-difluorobenzyl)oxy)-5,5a,6,6a-tetrahydrocyclopropa[4,5]cyclopenta[1,2-c]pyridine-6-carboxylate (3.0 g, 7.07 mmol), boronate 4,4,4',4',5,5,5',5'-octamethyl-2,2'-bi(1,3,2-dioxaborolane) (2.69 g, 10.6 mmol), KOAc (1.39 g, 14.14 mmol), and Pd(dppf)Cl$_2$ (517 mg, 0.71 mmol) in anhydrous DMF (2 mL)/anhydrous dioxane (6 mL) was charged in a sealed tube under a N$_2$ atmosphere and heated at 150° C. under microwave irradiation for 30 min. The mixture was then cooled to room temperature and diluted with EtOAc (50 mL) The organic layer was separated, washed with water and brine, dried over anhydrous Na$_2$SO$_4$ and concentrated. The resulting residue was purified by column chromatography on silica gel (PE/EtOAc=3/1) to give the title compound. MS (ESI) m/e (M+H$^+$): 500.2

Example 1

5aR,6S,6aS)-3-((4-fluoro-4'-(3-hydroxy-3-methylbutoxy)-2'-methyl-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid

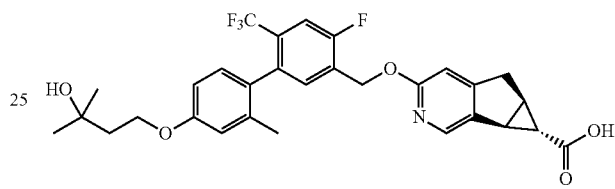

Step A:
4-(4-bromo-3-methylphenoxy)-2-methylbutan-2-ol

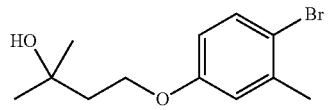

To a solution of Intermediate 2 (5.00 g, 19.4 mmol) in DMF (100 m) was added 4-bromo-3-methylphenol (3.00 g, 16.1 mmol) and K$_2$CO$_3$ (6.67 g, 48.3 mmol) under nitrogen. The reaction mixture was stirred at room temperature for 12 h. The mixture was then extracted with EtOAc (50 mL×3). The combined organic layers were washed with water and brine, dried over MgSO$_4$, and filtered. The filtrate was concentrated under reduced pressure. The resulting residue was purified by chromatography over silica gel (eluting with PE:EA=20:1) to give the title compound. $^1$H NMR (400 MHz, CDCl$_3$) δ: 7.11 (t, 2H, J=3.6 Hz), 6.77 (dd, 1H, J$_{13}$=8.8 Hz, J$_{12}$=2.4 Hz), 4.12 (t, 2H, J=6.2 Hz), 2.31 (s, 3H), 2.04 (br, 1H), 1.98 (t, 2H, J=6.4 Hz), 1.31 (s, 6H).

Step B: 2-methyl-4-(3-methyl-4-(4,4,5,5-tetramethyl-1,3,2-dioxaborolan-2-yl)phenoxy)butan-2-ol

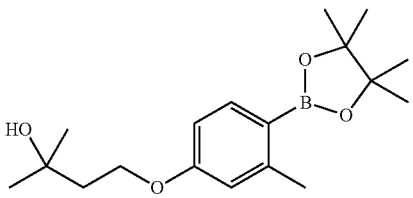 [SMILES: Cc1cc(OCCC(C)(C)O)ccc1B1OC(C)(C)C(C)(C)O1]

To a solution of the product from Step A (3.50 g, 12.9 mmol) in dioxane (55 mL) was added bis(pinacolato)diboron (4.91 g, 19.3 mmol), KOAc (3.79 g, 38.7 mmol) and Pd(dppf)Cl$_2$ (943 mg, 1.29 mmol) under nitrogen. The reaction mixture was stirred at 90° C. for 3 h, then cooled to room temperature, and extracted with EtOAc (30 mL×3). The combined organic layers were washed with water and brine, dried over MgSO$_4$, and filtered. The filtrate was concentrated under reduced pressure. The resulting residue was purified by chromatography over silica gel (eluting with PE:EA=50:1) to give the title compound as white solid. $^1$H NMR (400 MHz, CDCl$_3$) δ: 7.31 (d, 1H, J=2.8 Hz), 7.09 (d, 1H, J=8.4 Hz), 6.89 (dd, 1H, J$_{13}$=8.0 Hz, J$_{12}$=2.8 Hz), 4.20 (t, 2H, J=6.0 Hz), 2.56 (s, 3H), 1.99 (t, 2H, J=6.0 Hz), 1.35 (s, 12H), 1.31 (s, 6H)

Step C: (5aR,6S,6aS)-ethyl 3-((4-fluoro-4'-(3-hydroxy-3-methylbutoxy)-2'-methyl-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylate

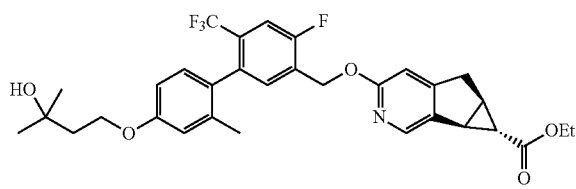 [SMILES: CCOC(=O)[C@H]1[C@@H]2Cc3cc(OCc4cc(-c5ccc(OCCC(C)(C)O)cc5C)c(C(F)(F)F)cc4F)ncc3[C@@H]21]

To a solution of Intermediate 5 (30.0 mg, 0.0634 mmol) in THF (1.5 mL) and H$_2$O (0.3 mL) were added the product from Step B (41.0 mg, 0.127 mmol), K$_3$PO$_4$ (40.0 mg, 0.190 mmol) and Pd(dtbpf)Cl$_2$ (4.00 mg, 0.006 mmol) under nitrogen. The reaction mixture was stirred at 100° C. for 3 h, then cooled to room temperature, and extracted with EtOAc (3 mL×3). The combined organic layers were washed with water and brine, dried over MgSO$_4$, and filtered. The filtrate was concentrated under reduced pressure. The resulting residue was purified by chromatography over silica gel (eluting with PE:EA=5:1) to give the title compound. MS (ESI) m/e (M+H$^+$): 588.2.

Step D: (5aR,6S,6aS)-3-((4-fluoro-4'-(3-hydroxy-3-methylbutoxy)-2'-methyl-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylic acid

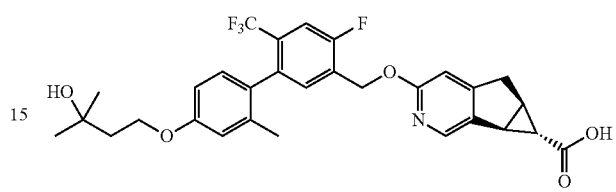

To a solution of the product from Step C (31.0 mg, 0.0528 mmol) in THF/MeOH/H$_2$O (1 mL/1 mL/1 mL) was added LiOH (22 mg, 0.528 mmol). The reaction mixture was stirred at room temperature for 2 h. Then HCl (1 mol/L) was added to the solution to adjust pH to 5 and the solution was extracted with EtOAc (5 mL×3). The combined organic layers were concentrated under reduced pressure. The resulting residue was purified by preparative HPLC [preparative HPLC on a GILSON 281 instrument fitted with a YMC-pack ODS-AQ (150×30 mm×5 um) column, using water and acetonitrile as the eluents. Mobile phase A: water, mobile phase B: acetonitrile. Gradient: 50-80% B, 0-10 min; 100% B, 10.5-12.5 min; 5% B, 13-15 min] to give the title compound. $^1$H NMR (400 MHz, MeOD-d$_4$) δ: 8.08 (s, 1H), 7.56 (d, 1H, J=10.6 Hz), 7.37 (t, 1H, J=6.4 Hz), 7.12 (d, 1H, J=8.4 Hz), 6.86-6.83 (m, 2H), 6.62 (s, 1H), 5.48 (s, 2H), 4.06 (t, 2H, J=6.8 Hz), 3.28 (s, 1H), 3.08 (d, 1H, J=18.8 Hz), 2.94 (d, 1H, J=6.4 Hz), 2.45 (br, 1H), 1.92 (t, 2H, J=6.8 Hz), 1.84 (d, 3H, J=2.8 Hz), 1.23 (s, 6H), 1.17 (s, 1H). MS (ESI) m/e (M+H$^+$): 559.

Examples 2 to 4 was prepared in a similar manner to Example 1 using the appropriate intermediates and commercially available starting materials.

| Example | Structure | M.W. | Compound Name | LC/MS (ESI) observed [M + 1]+ |
|---|---|---|---|---|
| 2 | ![structure] | 593 | (5aR,6S,6aS)-3-((4-fluoro-2'-methyl-4'-(3-(methyl-sulfonyl)-propoxy)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 594 |
| 3 | ![structure] | 560 | (5aR,6S,6aS)-3-((2-fluoro-5-(6-(3-hydroxy-3-methylbutoxy)-2-methyl-pyridin-3-yl)-4-(trifluoromethyl)-benzyl)-oxy)-5,5a,6,6a-tetrahydro-cyclopropa[4,5]cyclopenta[1,2-c]pyridine-6- | 561 |

| Example | Structure | M.W. | Compound Name | LC/MS (ESI) observed [M + 1]+ |
|---|---|---|---|---|
| | | | carboxylic acid | |
| 4 | 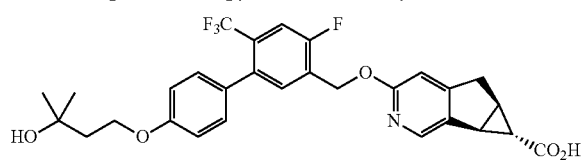 | 541 | (5aR,6S,6aS)-3-((6-(difluoromethyl)-4-fluoro-4'-(3-hydroxy-3-methyl-butoxy)-2'-methyl-[1,1'-biphenyl]-3-yl)methoxy)-5,5a,6,6a-tetrahydrocyclopropa[4,5]cyclopenta[1,2-c]pyridine-6-carboxylic acid | 542 |

Example 5

(5aR,6S,6aS)-3-((4-fluoro-4'-(3-hydroxy-3-methyl-butoxy)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid

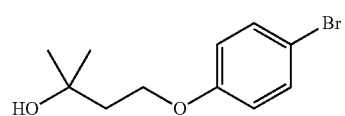

Step A: 4-(4-bromophenoxy)-2-methylbutan-2-ol

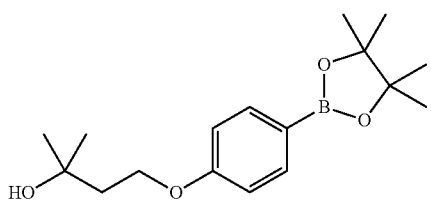 [SMILES: CC(C)(O)CCOc1ccc(B2OC(C)(C)C(C)(C)O2)cc1]

To a solution of 4-bromophenol (1 g, 5.78 mmol) in DMF (10 ml) were added Intermediate 2 (1.49 g, 5.78 mmol) and K$_2$CO$_3$ (2.4 g, 17.34 mmol). The mixture was stirred at 100° C. for 4 h. Then the reaction mixture was cooled to 25° C., washed with brine (30 mL) and extracted with EtOAc (10 mL×2). The combined organic layers were separated, dried and concentrated under vacuum. The resulting crude residue was purified by chromatography over silica gel (eluting with PE:EA=5:1) to give the title compound.

Step B: 2-methyl-4-(4-(4,4,5,5-tetramethyl-1,3,2-dioxaborolan-2-yl)phenoxy)butan-2-ol A mixture of the product from Step A (1.41 g, 5.44 mmol), bis(pinacolato)diboron (1.52 g, 5.98 mmol), Pd(dppf)Cl$_2$ (398 mg, 0.544 mmol) and KOAc (1.07 g, 10.88 mmol) in dioxane (14 mL) was stirred at 90-100° C. under N$_2$ for 18 h. Then the reaction mixture was filtered and concentrated under vacuum. The resulting crude product was purified by chromatography over silica gel (eluting with PE:EA=5:1) to give compound the title compound.

Step C: (5aR,6S,6aS)-ethyl 3-((4-fluoro-4'-(3-hydroxy-3-methylbutoxy)-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylate

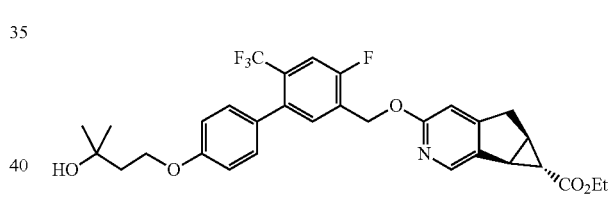

A mixture of Intermediate 5 (774 mg, 1.63 mmol), the product from Step B (500 mg, 1.63 mmol), Pd(dtbpf)Cl$_2$ (104 mg, 0.16 mmol) and K$_3$PO$_4$ (691 mg, 3.26 mmol) in THF/H$_2$O (5/1 mL) was stirred at 100° C. under N$_2$ for 15 min in a microwave. The reaction mixture was washed with brine (20 mL) and extracted with EtOAc (6 mL×3). The combined organic layers were concentrated under vacuum. The resulting crude product was purified by chromatography over silica gel (eluting with PE:EA=10:1) to give the title compound. MS (ESI) m/e (M+H$^+$): 574.

Step D: (5aR,6S,6aS)-3-((4-fluoro-4'-(3-hydroxy-3-methylbutoxy)-6-(trifluoromethyl)-[1,1'-biphenyl]-3-yl) methoxy)-5,5a,6,6a-tetrahydrocyclopropa[4,5]cyclopenta[1,2-c]pyridine-6-carboxylic acid

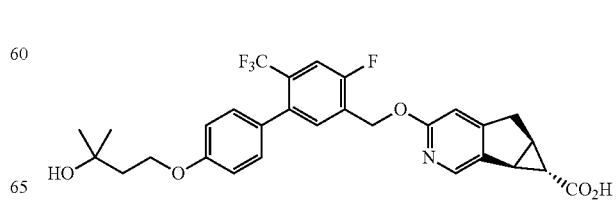

To a solution of the product from Step C (400 mg, 0.698 mmol) in EtOH/H$_2$O (6/1 mL) was added LiOH (293 mg, 6.98 mmol). The reaction mixture was stirred at 20-24° C. for 18 h. Then HCl (2 mol/L) was added to the reaction to adjust the pH to 5, and the reaction mixture was washed with brine (15 mL) and extracted with EtOAc (5 mL×3). The combined organic layers were concentrated under vacuum. The resulting residue was purified by preparative HPLC on a GILSON 281 instrument fitted with a Diamonsil (150×20 mm×5 um) column, using water and acetonitrile as the eluents. Mobile phase A: water (containing 0.1% TFA, v/v), mobile phase B: acetonitrile. Gradient: 49-79% B, 0-10 min; 100% B, 10.5-12.5 min; 5% B, 13-15 min] to give the title compound. $^1$HNMR (400 MHz, MeOH) δ: 8.06 (s, 1H), 7.51 (d, J=10.2 Hz, 1H), 7.45 (d, J=7.0 Hz, 1H), 7.16 (d, J=8.6 Hz, 2H), 6.93 (d, J=8.6 Hz, 2H), 6.74 (s, 1H), 5.44 (s, 2H), 4.15 (t, J=6.8 Hz, 2H), 3.23 (d, J=6.3 Hz, 1H), 3.04 (d, J=18.4 Hz, 1H), 2.92 (d, J=5.5 Hz, 1H), 2.46-2.39 (m, 1H), 2.02-1.93 (m, 3H), 1.27 (s, 6H), 1.14 (br. s., 1H). MS (ESI) m/e (M+H$^+$): 546.

Examples 6 to 11 were prepared in a similar manner to Example 5 using the appropriate intermediates and commercially available starting materials.

| Example | Structure | M.W. | Compound Name | LC/MS (ESI) observed [M + 1]+ |
|---|---|---|---|---|
| 6 | 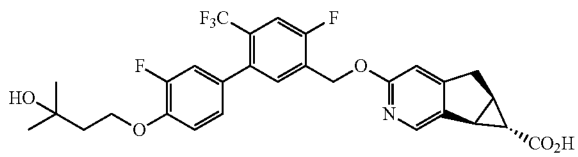 [SMILES: CC(C)(O)CCOc1ccc(-c2cc(COc3cc4c(cn3)[C@H]3[C@@H](C4)[C@@H]3C(=O)O)c(F)cc2C(F)(F)F)cc1F] | 563 | (5aR,6S,6aS)-3-((3',4-difluoro-4'-(3-hydroxy-3-methyl-butoxy)-6-(trifluoro-methyl)-[1,1'-biphenyl]-3-yl)methoxy)-5,5a,6,6a-tetrahydrocyclopropa[4,5]cyclopenta[1,2-c]pyridine-6-carboxylic acid | 564 |
| 7 | 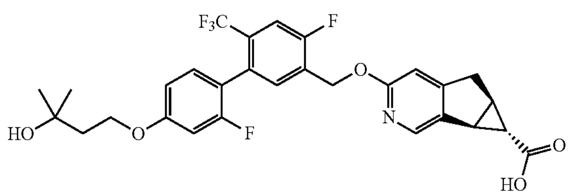 [SMILES: CC(C)(O)CCOc1ccc(-c2cc(COc3cc4c(cn3)[C@H]3[C@@H](C4)[C@@H]3C(=O)O)c(F)cc2C(F)(F)F)c(F)c1] | 563 | (5aR,6S,6aS)-3-((2',4-difluoro-4'-(3-hydroxy-3-methylbutoxy)-6-(trifluoro-methyl)-[1,1'-biphenyl]-3-yl)methoxy)-5,5a,6,6a-tetrahydrocyclopropa[4,5]cyclopenta[1,2-c]pyridine-6-carboxylic acid | 564 |
| 8 | 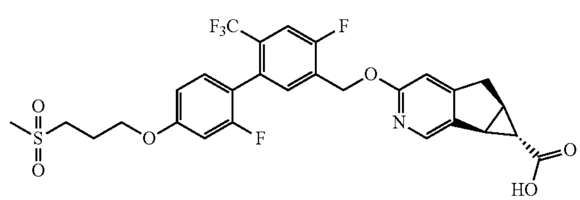 [SMILES: CS(=O)(=O)CCCOc1ccc(-c2cc(COc3cc4c(cn3)[C@H]3[C@@H](C4)[C@@H]3C(=O)O)c(F)cc2C(F)(F)F)c(F)c1] | 597 | (5aR,6S,6aS)-3-((2',4-difluoro-4'-(3-(methyl-sulfonyl)-propoxy)-6-(trifluoromethyl)-[1,1'-biphenyl]-3-yl)methoxy)-5,5a,6,6a-tetrahydro-cyclopropa[4,5]cyclo-penta[1,2-c]pyridine-6-carboxylic acid | 598 |
| 9 | 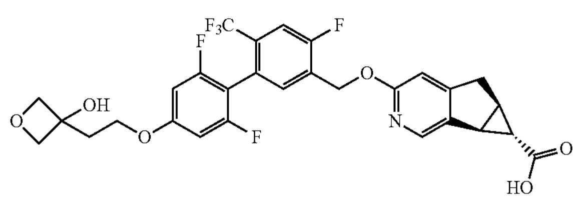 [SMILES: O=C(O)[C@H]1[C@@H]2Cc3cc(OCc4cc(-c5c(F)cc(OCCC6(O)COC6)cc5F)c(C(F)(F)F)cc4F)ncc3[C@@H]21] | 595 | (5aR,6S,6aS)-3-((2',4,6'-trifluoro-4'-(2-(3-hydroxy-oxetan-3-yl)ethoxy)-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid | 596 |
| 10 | 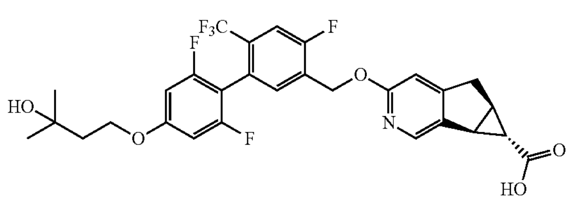 [SMILES: CC(C)(O)CCOc1cc(F)c(-c2cc(COc3cc4c(cn3)[C@H]3[C@@H](C4)[C@@H]3C(=O)O)c(F)cc2C(F)(F)F)c(F)c1] | 581 | (5aR,6S,6aS)-3-((2',4,6'-trifluoro-4'-(3-hydroxy-3-methylbutoxy)-6-(trifluoromethyl)-[1,1'-biphenyl]-3-yl)methoxy)-5,5a,6,6a-tetrahydrocyclo-propa[4,5]cyclopenta[1,2-c]pyridine-6-carboxylic acid | 582 |

| Example | Structure | M.W. | Compound Name | LC/MS (ESI) observed [M + 1]+ |
|---|---|---|---|---|
| 11 | 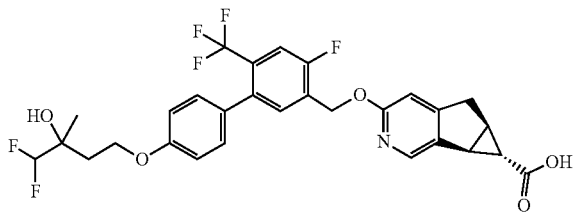 [SMILES: CC(O)(CCOc1ccc(-c2cc(COc3cc4c(cn3)[C@H]3[C@@H](C4)[C@@H]3C(=O)O)c(F)cc2C(F)(F)F)cc1)C(F)F] | 545 | (5aR,6S,6aS)-3-((6-(difluoro-methyl)-3',4-difluoro-4'-(3-hydroxy-3-methyl-butoxy)-[1,1'-biphenyl]-3-yl)methoxy)-5,5a,6,6a-tetrahydro-cyclopropa[4,5]cyclopenta[1,2-c]pyridine-6-carboxylic acid | 546 |

Example 12

(5aR,6S,6aS)-3-((4'-(4,4-difluoro-3-hydroxy-3-methylbutoxy)-4-fluoro-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid

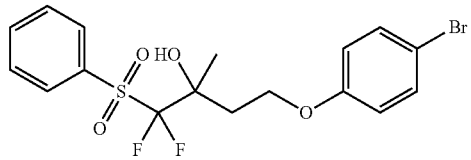 [SMILES: CC(O)(CCOc1ccc(Br)cc1)C(F)(F)S(=O)(=O)c1ccccc1]

Step A: 4-(4-bromophenoxy)-1,1-difluoro-2-methyl-1-(phenylsulfonyl)butan-2-ol

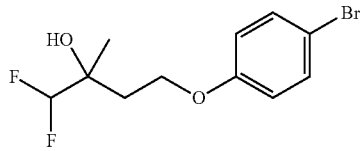 [SMILES: CC(O)(CCOc1ccc(Br)cc1)C(F)F]

A mixture of Intermediate 4 (434.37 mg, 1 mmol, 4-bromophenol (138 mg, 0.8 mmol) and K₂CO₃ (276 mg, 2.0 mmol) in DMF (10 mL) was stirred at room temperature overnight. The resulting mixture was filtered and the filtrate was partitioned between EtOAc and water. The aqueous phase was separated, washed with brine, dried over Na₂SO₄, filtered and concentrated under vacuum. The resulting residue was purified by chromatography over silica gel (eluting with PE:EA=4:1) to give the title compound as a yellow oil. MS (ESI) m/e (M+H⁺): 463.0

Step B: 4-(4-bromophenoxy)-1,1-difluoro-2-methylbutan-2-ol

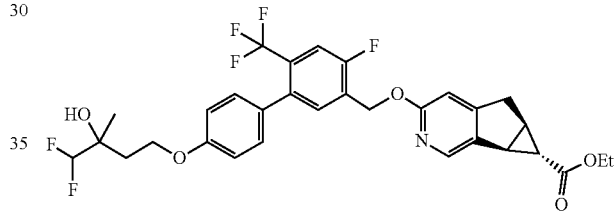

To a suspension of the product from Step A (300 mg, 0.69 mmol), NaOAc (1.3 g, 15.85 mmol) in AcOH/H₂O/DMF (2 mL/8 mL/20 mL) was added Mg powder (251 mg, 10.34 mmol) and the mixture was stirred at room temperature overnight. The reaction mixture was then partitioned between EtOAc and water. The aqueous layer was separated, and extracted with EtOAc three times. The combined organic layers were washed with water, dried and concentrated in vacuo. The resulting crude product was purified by chromatography over silica gel (eluting with PE:EA=5:1) to afford the title compound as a yellow oil. MS (ESI) m/e (M+H⁺): 295.1.

Step C: (5aR,6S,6aS)-ethyl3-((4'-(4,4-difluoro-3-hydroxy-3-methylbutoxy)-4-fluoro-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylate

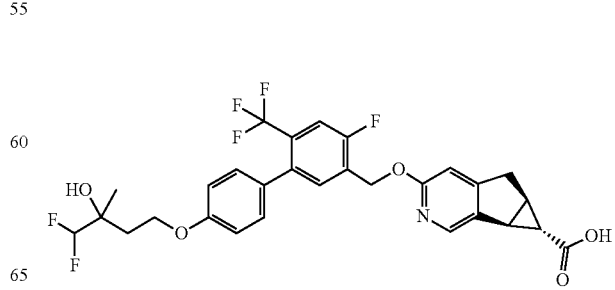

A mixture of the product from Step B (30 mg, 0.102 mmol), Intermediate 6 (63.6 mg, 0.122 mmol), K₃PO₄ (64.7 mg, 0.305 mmol) and Pd(dppf)Cl₂ (13.25 mg, 0.020 mmol) in THF (3 ml) and water (1 ml) was heated in a microwave at 100° C. for 30 min under a nitrogen atmosphere. After cooling to room temperature, the reaction mixture was filtered, the insoluble part was removed. The filtrate was extracted with EtOAc. The organic layer was separated, washed with water, dried and concentrated to give the title compound as a brown oil, which was used in the next step without further purification. MS (ESI) m/e (M+H⁺): 609.2.

Step D: (5aR,6S,6aS)-3-((4'-(4,4-difluoro-3-hydroxy-3-methylbutoxy)-4-fluoro-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylic acid To a mixture of the crude product from Step C (55 mg, crude) in MeOH (1.00 mL), THF (1.00 mL) and water (1.00 mL) was added lithium hydroxide (33 mg, 0.835 mmol), and the reaction mixture was stirred at room temperature for 2 hrs. The resulting mixture was acidified with HCl (2 N) to pH=3, and extracted with ethyl acetate. The combined organic layers were washed with water, brine, dried over $Na_2SO_4$ and concentrated in vacuo to afford a residue, which was purified by preparative HPLC on a GILSON 281 instrument fitted with a Waters XSELECT C18 (150×30 mm×5 um) column using water and acetonitrile as the eluents. Mobile phase A: water (containing 0.1% TFA, v/v), mobile phase B: acetonitrile. Gradient: 55-75% B, 0-10 min; 100% B, 10.5-12.5 min; 5% B, 13-15 min] to provide the title compound as a yellow solid. $^1$HNMR (400 MHz, $CDCl_3$) δ: 8.17 (s, 1H), 7.49-7.42 (m, 2H), 7.23 (d, J=8.5 Hz, 2H), 6.93 (d, J=8.5 Hz, 2H), 6.70 (s, 1H), 5.69 (s, 1H), 5.46 (s, 2H), 4.27 (t, J=6.0 Hz, 2H), 3.32 (br. s., 1H), 3.12-3.00 (m, 2H), 2.59-2.51 (m, 1H), 2.24-2.02 (m, 2H), 1.36 (s, 3H), 1.26 (br. s., 1H). MS (ESI) m/e (M+H$^+$): 581.2.

Example 13 was prepared in a similar manner to Example 12 using the appropriate intermediates and commercially available starting materials.

washed with water, dried and concentrated in vacuo to yield a residue, which was purified by flash chromatography over silica gel (eluting with PE:EA=4:1) to afford the title compound as a yellow oil. MS (ESI) m/e (M+H$^+$): 288.

Step B: (5aR,6S,6aS)-ethyl 3-((4-fluoro-4'-(2-(3-hydroxyoxetan-3-yl)ethoxy)-2'-methyl-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylate

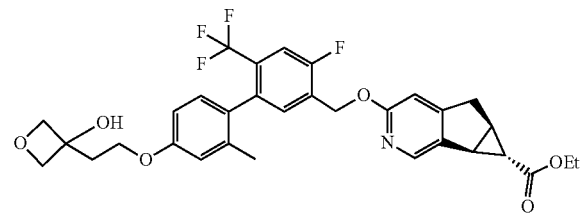

| Example | Structure | M.W. | Compound Name | LC/MS (ESI) observed [M + 1]+ |
|---|---|---|---|---|
| 13 | 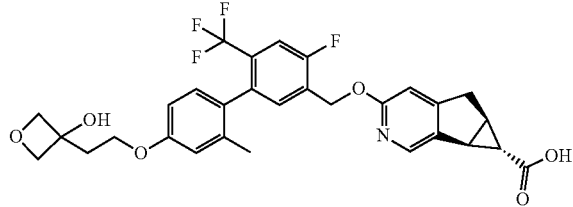 | 595 | (5aR,6S,6aS)-3-((2'-(difluoromethyl)-4-fluoro-4'-(3-hydroxy-3-methyl-butoxy)-6-(trifluoromethyl)-[1,1'-biphenyl]-3-yl)-methoxy)-5,5a,6,6a-tetra-hydrocyclo-propa[4,5]cyclopenta[1,2-c]pyridine-6-carboxylic acid | 596 |

Example 14

(5aR,6S,6aS)-3-((4-fluoro-4'-(2-(3-hydroxyoxetan-3-yl)ethoxy)-2'-methyl-6-(trifluoromethyl)-[1,1'-biphenyl]-3-yl)methoxy)-5,5a,6,6a-tetrahydrocyclopropa[4,5]cyclopenta[1,2-c]pyridine-6-carboxylic acid

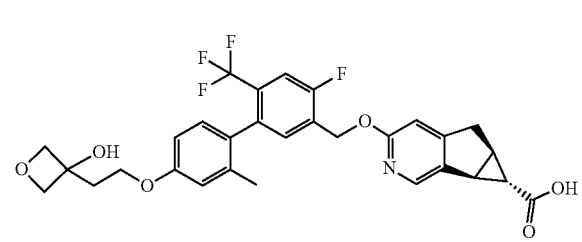 [SMILES: Cc1cc(OCCC2(O)COC2)ccc1-c1cc(COc2cc3c(cn2)[C@H]2[C@@H](C3)[C@@H]2C(=O)O)c(F)cc1C(F)(F)F]

Step A: 3-(2-(4-bromo-3-methylphenoxy)ethyl)oxetan-3-ol

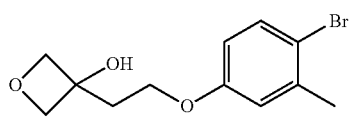 [SMILES: Cc1cc(OCCC2(O)COC2)ccc1Br]

A mixture of intermediate 3 (200 mg, 0.734 mmol), 4-bromo-3-methylphenol (137 mg, 0.732 mmol) and $K_2CO_3$ (152 mg, 1.102 mmol) in acetonitrile (4 ml) was stirred at 80° C. overnight. The reaction mixture was extracted with EtOAc three times. The combined organic layers were A mixture of the product from Step A (50 mg, 0.174 mmol), Intermediate 6 (109 mg, 0.209 mmol), Pd(dtbpf)Cl$_2$ (11.35 mg, 0.017 mmol) and $K_3PO_4$ trihydrate (93 mg, 0.348 mmol) in THF (3 mL) and water (1 mL) was heated in a microwave at 100° C. for 30 min under a nitrogen atmosphere. After cooling to room temperature, the reaction mixture was filtered and the filtrate was extracted with EtOAc. The combined organic layers were washed with water, dried and concentrated in vacuo to give the title compound as a crude product, which was used in the next step without purification. MS (ESI) m/e (M+H$^+$): 602.

Step C: (5aR,6S,6aS)-3-((4-fluoro-4'-(2-(3-hydroxyoxetan-3-yl)ethoxy)-2'-methyl-6-(trifluoromethyl)-[1,1'-biphenyl]-3-yl)methoxy)-5,5a,6,6a-tetrahydrocyclopropa[4,5]-cyclopenta[1,2-c]pyridine-6-carboxylic acid To a mixture of the product from Step B (31 mg, 0.052 mmol) in MeOH (3.00 ml), THF (3.00 ml) and water (3.00 ml) was added lithium hydroxide (4.94 mg, 0.206 mmol), and the reaction was stirred at room temperature for 2 hrs. The resulting mixture was acidified with 2N HCl to pH=3 and extracted with ethyl acetate. The combined organic layers were washed with water, brine, dried over $Na_2SO_4$ and concentrated in vacuo to afford a residue, which was purified by preparative HPLC on a GILSON 281 instrument fitted with a Phenomenex Gemini C18 (150×30 mm×5 um) column, using water and acetonitrile as the eluents. Mobile phase A: water (containing 0.1% TFA, v/v), mobile phase B: acetonitrile. Gradient: 45-65% B, 0-10 min; 100% B, 10.5-12.5 min; 5% B, 13-15 min] to provide the title compound as a yellow solid. $^1$H NMR (400 MHz, MeOH-$d_4$) δ: 8.05 (br. s., 1H), 7.54 (d, J=9.4 Hz, 1H), 7.33 (t, J=5.7 Hz, 1H), 6.96 (d, J=6.7 Hz, 1H), 6.83-6.60 (m, 3H), 5.46 (br. s., 2H), 4.71 (d, J=6.3 Hz, 2H), 4.62 (d, J=6.7 Hz, 2H), 4.18 (br. s., 2H), 3.24 (d, J=18.8 Hz, 1H), 3.03 (d, J=17.6 Hz, 1H), 2.91 (br. s., 1H), 2.43 (br. s., 1H), 2.30 (t, J=5.7 Hz, 2H), 2.00 (d, J=8.6 Hz, 1H), 1.89 (br. s., 3H), 1.13 (br. s., 1H). MS (ESI) m/e (M+H$^+$): 574.

Example 15

(5aR,6S,6aS)-3-((2-fluoro-5-(5-fluoro-6-(3-hydroxy-3-methylbutoxy)pyridin-3-yl)-4-(trifluoromethyl)benzyl)oxy)-5,5a,6,6a-tetrahydrocyclopropa[4,5]cyclopenta[1,2-c]pyridine-6-carboxylic acid

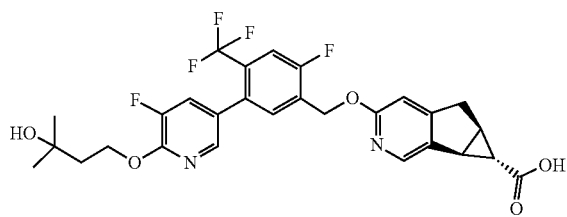 [SMILES: CC(C)(O)CCOc1ncc(-c2cc(COc3cc4c(cn3)[C@H]3[C@@H](C4)[C@@H]3C(=O)O)c(F)cc2C(F)(F)F)cc1F]

Step A: 5-bromo-3-fluoropyridin-2-ol

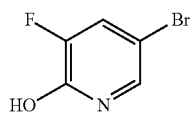

A mixture of 5-bromo-3-fluoro-2-methoxypyridine (1.2 g, 5.82 mmol) in concentrated HCl (5 ml, 60.9 mmol) was stirred at 100° C. for 12 h. Then the mixture was concentrated in vacuo to give the title compound as a white solid. MS (ESI) m/e (M+H$^+$): 192, 194.

Step B: 4-((5-bromo-3-fluoropyridin-2-yl)oxy)-2-methylbutan-2-ol

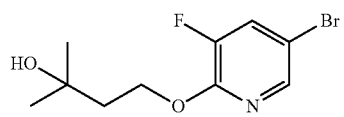

To a mixture of Intermediate 2 (740 mg, 2.86 mmol) and the product from Step A (500 mg, 2.60 mmol) in DMF (4 mL) was added $K_2CO_3$ (720 mg, 5.21 mmol). The resulting reaction mixture was stirred at 80° C. for 3 h, and then filtered. The filtrate was concentrated and the resulting residue was purified by chromatography over silica gel (eluting with PE:EA=1:1), to give the title compound. MS (ESI) m/e (M+H$^+$): 278, 280.

Step C: (5aR,6S,6aS)-3-((2-fluoro-5-(5-fluoro-6-(3-hydroxy-3-methylbutoxy)pyridin-3-yl)-4-(trifluoromethyl)benzyl)oxy)-5,5a,6,6a-tetrahydrocyclopropa[4,5]cyclopenta[1,2-c]pyridine-6-carboxylic acid

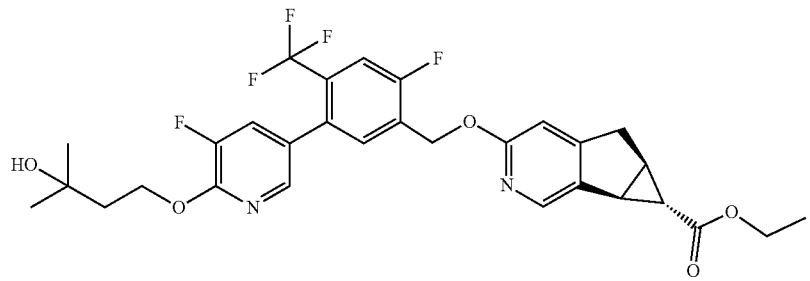 [SMILES: CCOC(=O)[C@H]1[C@@H]2Cc3cc(OCc4cc(-c5cnc(OCCC(C)(C)O)c(F)c5)c(C(F)(F)F)cc4F)ncc3[C@@H]21]

To a solution of the product from Step B (30 mg, 0.108 mmol) in THF (2.0 mL) was added Intermediate 6 (45 mg, 0.086 mmol), $K_3PO_4/H_2O$ (0.5 ml, 1 mol/L) and Pd(dtbpf)Cl$_2$ (8 mg, 0.01 mmol). The resulting mixture was heated at 100° C. in a microwave for 15 min. Then the reaction mixture was purified by chromatography over silica gel (eluting with PE:EA=3:1) to give the title compound. MS (ESI) m/e (M+H$^+$): 593.

Step D: (5aR,6S,6aS)-3-((2-fluoro-5-(5-fluoro-6-(3-hydroxy-3-methylbutoxy)pyridin-3-yl)-4-(trifluoromethyl)benzyl)oxy)-5,5a,6,6a-tetrahydrocyclopropa[4,5]cyclopenta[1,2-c]pyridine-6-carboxylic acid

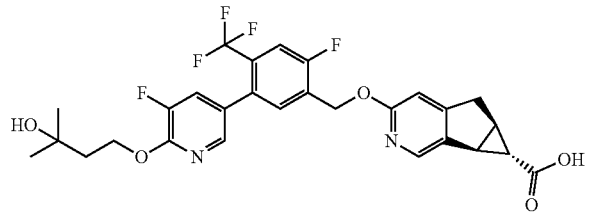 [SMILES: CC(C)(O)CCOc1ncc(-c2cc(COc3cc4c(cn3)[C@H]3[C@@H](C4)[C@@H]3C(=O)O)c(F)cc2C(F)(F)F)cc1F]

To a solution of the product from Step C (16 mg, 0.027 mmol) in MeOH (3 mL) and water (1 mL) was added LiOH (50 mg, 2 mmol). The resulting mixture was stirred at rt. for 2 hours. Then water was added and the solution was acidified with HCl (1M) to pH=2.5, and extracted with EtOAc (10 mL×3). The combined organic layers were washed with brine, dried and concentrated in vacuo to give the title compound. $^1$H NMR (400 MHz, CDCl$_3$) δ: 7.33 (d, J=10.0 Hz, 1H), 6.65 (s, 1H), 5.53-5.44 (m, 2H), 4.63 (t, J=7.0 Hz, 2H), 3.23 (d, J=6.0 Hz, 1H), 3.09-2.95 (m, 2H), 2.53 (dt, J=3.5, 6.3 Hz, 1H), 2.07 (t, J=7.0 Hz, 2H), 1.35 (s, 6H), 1.26 (s, 1H). MS (ESI) m/e (M+H$^+$): 565.

Examples 16 and 17 were prepared in a similar manner to Example 15 using the appropriate intermediates and commercially available starting materials.

| Example | Structure | M.W. | Compound Name | LC/MS (ESI) observed [M + 1]+ |
|---|---|---|---|---|
| 16 | 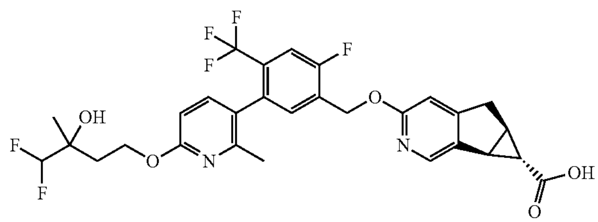 [SMILES: Cc1nc(OCCC(C)(O)C(F)F)ccc1-c1cc(COc2cc3c(cn2)[C@H]2[C@@H](C3)[C@@H]2C(=O)O)c(F)cc1C(F)(F)F] | 595 | (5aR,6S,6aS)-3-((5-(6-(4,4-difluoro-3-hydroxy-3-methylbutoxy)-2-methylpyridin-3-yl)-2-fluoro-4-(trifluoromethyl)-benzyl)-oxy)-5,5a,6,6a-tetrahydro-cyclopropa[4,5]cyclopenta[1,2-c]pyridine-6-carboxylic acid | 597 |
| 17 | 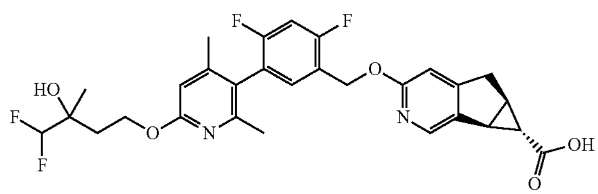 [SMILES: Cc1cc(OCCC(C)(O)C(F)F)nc(C)c1-c1cc(COc2cc3c(cn2)[C@H]2[C@@H](C3)[C@@H]2C(=O)O)c(F)cc1F] | 560 | (5aR,6S,6aR)-3-((5-(6-(4,4-difluoro-3-hydroxy-3-methylbutoxy)-2,4-dimethylpyridin-3-yl)-2,4-difluorobenzyl)oxy)-5,5a,6,6a-tetrahydrocyclopropa[4,5]cyclopenta[1,2-c]pyridine-6-carboxylic acid | 561 |

Example 18

(5aR,6S,6aS)-3-((4'-((3,4-dihydroxy-4-methylpentyl)oxy)-4,6-difluoro-2',6'-dimethyl-[1,1'-biphenyl]-3-yl)methoxy)-5,5a,6,6a-tetrahydrocycloprop[4,5]cyclopenta[1,2-c]pyridine-6-carboxylic acid

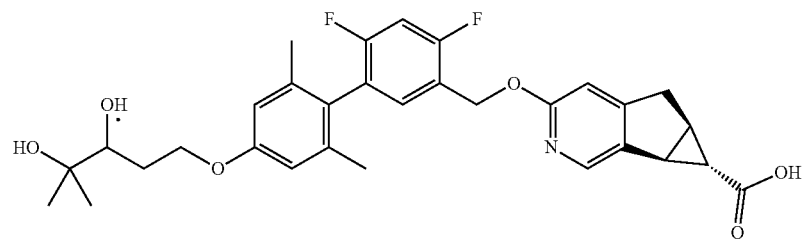

Step A: 2-bromo-1,3-dimethyl-5-((4-methylpent-3-en-1-yl)oxy)benzene

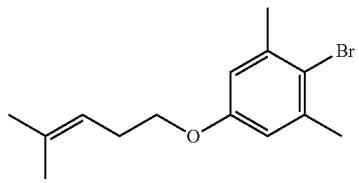 [SMILES: CC(C)=CCCOc1cc(C)c(Br)c(C)c1]

A mixture of 5-bromo-2-methylpent-2-ene (500 mg, 3.07 mmol), 4-bromo-3,5-dimethylphenol (617 mg, 3.07 mmol), $K_2CO_3$ (848 mg, 6.13 mmol) and acetone (10 mL) was stirred at 60° C. for 18 hours. Then the reaction was cooled to rt and poured into water (30 mL), and the resulting mixture was extracted with EtOAc. The combined organic layers were washed with brine, dried over $Na_2SO_4$, filtered and the solvent was evaporated under reduced pressure. The resulting residue was purified by chromatography over silica gel (eluting with PE:EA=100:1 to 50:1) to give the title compound.

Step B: 5-(4-bromo-3,5-dimethylphenoxy)-2-methylpentane-2,3-diol

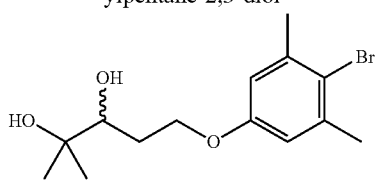

To a mixture of 2-bromo-1,3-dimethyl-5-((4-methylpent-3-en-1-yl)oxy)benzene (600 mg, 2.12 mmol) and 4-methylmorpholine 4-oxide (745 mg, 6.36 mmol) in a co-solvent of acetone and water (22 mL, 10:1) was added osmium(VIII) oxide (26.9 mg, 0.106 mmol) at room temperature. The resulting mixture was stirred at room temperature for 12 hrs, then quenched by the addition of solid $Na_2SO_3$ (1.0 g). The resulting mixture was stirred for 1.5 hrs at room temperature, then diluted with DCM and washed with water, followed by saturated $NaHCO_3$ solution, water, and brine. The separated organic layer was then dried over $Na_2SO_4$, filtered and concentrated in vacuo. The resulting residue was purified by chromatography over silica gel (eluting with PE:EA=1:1) to give the title compound. MS (ESI) m/e $(M+H^+)$: 317.1/319.1.

Step C: (5aR,6S,6aS)-tert-butyl 3-((4'-((3,4-dihydroxy-4-methylpentyl)oxy)-4,6-difluoro-2',6'-dimethyl-[1,1'-biphenyl]-3-yl)methoxy)-5,5a,6,6a-tetrahydrocyclopropa[4,5]-cyclopenta[1,2-c]pyridine-6-carboxylate

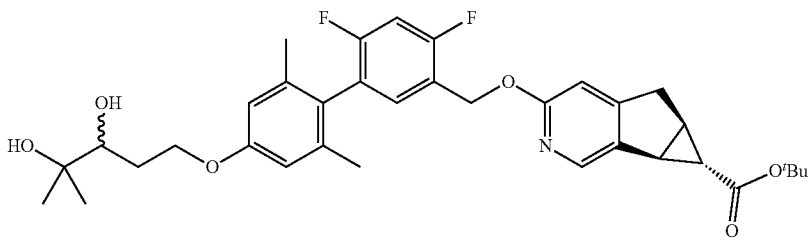 [SMILES: Cc1cc(OCCC(O)C(C)(C)O)cc(C)c1-c1cc(COc2cc3c(cn2)[C@H]2[C@@H](C3)[C@@H]2C(=O)OC(C)(C)C)c(F)cc1F]

A mixture of $PdCl_2(dppf)$ (27.7 mg, 0.038 mmol), $K_2CO_3$ (131 mg, 0.946 mmol), intermediate 11 (208 mg, 0.416 mmol), and 5-(4-bromo-3,5-dimethyl phenoxy)-2-methylpentane-2,3-diol (120 mg, 0.378 mmol) in a co-solvent of THF (2.0 mL) and water (0.7 mL) was charged in a sealed tube under $N_2$ atmosphere, and then radiated by microwave at 100° C. for 30 mins. After cooling to room temperature, the mixture was filtered. The filtrate was diluted with DCM (25 mL) and washed with water (20 mL), dried over $Na_2SO_4$ and filtered, concentrated in vacuo to give the crude product, which was purified by chromatography over silica gel (eluting with PE:EA=2:1) to give the title compound. MS (ESI) m/e $(M+H^+)$: 610.3.

Step D: (5aR,6S,6aS)-tert-butyl 3-((4'-((3,4-dihydroxy-4-methylpentyl)oxy)-4,6-difluoro-2',6'-dimethyl-[1,1'-biphenyl]-3-yl)methoxy)-5,5a,6,6a-tetrahydrocyclopropa[4,5]-cyclopenta[1,2-c]pyridine-6-carboxylate

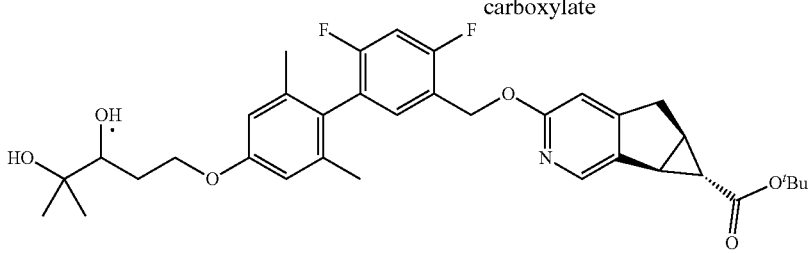

(5aR,6S,6aS)-tert-butyl 3-((4'-((3,4-dihydroxy-4-methylpentyl)oxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate (180 mg, 0.295 mmol) was resolved by SFC (Column: Chiralcel OD-H 250×4.6 mm I.D., 5 um Mobile phase: methanol (0.05% DEA) in CO$_2$ from 5% to 40% Flow rate: 2.35 mL/min Wavelength: 220 nm) to afford the first peak isomer with shorter retention time in chiral HPLC (5aR,6S,6aS)-tert-butyl 3-((4'-((3,4-dihydroxy-4-methylpentyl)oxy)-4,6-difluoro-2',6'-dimethyl-[1,1'-biphenyl]-3-yl) methoxy)-5,5a,6,6a-tetrahydrocyclopropa[4,5]cyclopenta[1,2-c]pyridine-6-carboxylate; and the second peak isomer with longer retention time in chiral HPLC (5aR,6S,6aS)-tert-butyl 3-((4'-((3,4-dihydroxy-4-methylpentyl)oxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6. MS (ESI) m/e (M+H$^+$): 610.3 for both.

Step E: (5aR,6S,6aS)-3-((4'-((3,4-dihydroxy-4-methylpentyl)oxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid To a mixture of (5aR,6S,6aS)-tert-butyl 3-((4'-((3,4-dihydroxy-4-methyl pentyl)oxy)-4,6-difluoro-2',6'-dimethyl-[1,1'-biphenyl]-3-yl)methoxy)-5,5a,6,6a-tetrahydrocyclopropa-[4,5]cyclopenta[1,2-c]pyridine-6-carboxylate (first peak isomer, 75 mg, 0.123 mmol) in a co-solvent of THF (2 ml), MeOH (2 mL) and H$_2$O (2 mL) was added NaOH (24.60 mg, 0.615 mmol) and the resulting mixture was stirred at 60° C. for 2 hrs. Then the resulting mixture was cooled to rt, acidified by HCl (2 N) to pH=6, and then extracted with EtOAc. The organic layer was separated, washed with water (20 mL) and brine, dried over Na$_2$SO$_4$ and concentrated in vacuo to get the crude product, which was purified by silica gel preparative TLC (PE/EA=1:1) to give the title compound. $^1$H NMR (400 MHz, MeOD-d$_4$) δ: 7.97-8.09 (m, 1H), 7.16-7.27 (m, 1H), 6.97-7.09 (m, 1H), 6.66 (s, 2H), 6.63 (s, 1H), 5.33 (s, 2H), 4.07-4.17 (m, 2H), 3.51-3.59 (m, 1H), 3.14-3.25 (m, 1H), 2.94-3.04 (m, 1H), 2.85-2.91 (m, 1H), 2.34-2.45 (m, 1H), 2.03-2.17 (m, 1H), 1.91 (s, 6H), 1.62-1.75 (m, 1H), 1.18 (d, J=10.96 Hz, 6H), 1.06-1.13 (m, 1H). MS (ESI) m/e (M+H$^+$): 554.2.

Examples 19 to 21 were prepared in a similar manner to Example 18 using the appropriate intermediates and commercially available starting materials.

| Example | Structure | M.W. | Compound Name | LC/MS (ESI) observed [M + 1]+ |
|---|---|---|---|---|
| 19 | 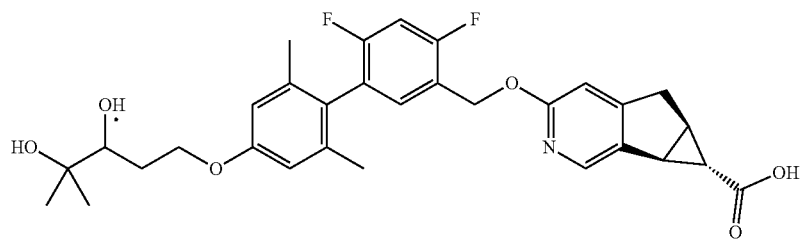 | 539 | (5aR,6S,6aS)-3-((4'-(3,4-dihydroxy-3-methyl-butoxy)-4,6-difluoro-2',6'-dimethyl-[1,1'-biphenyl]-3-yl)methoxy)-5,5a,6,6a-tetrahydro-cyclopropa[4,5]-cyclopenta[1,2-c]pyridine-6-carboxylic acid | 540 |

| Example | Structure | M.W. | Compound Name | LC/MS (ESI) observed [M + 1]+ |
|---|---|---|---|---|
| 20 | 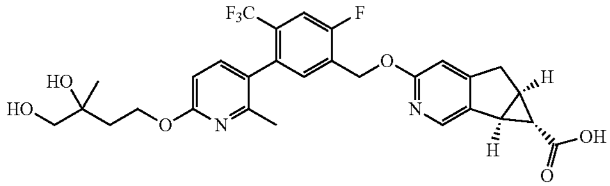 [SMILES: Cc1nc(OCCC(C)(O)CO)ccc1-c1cc(COc2cc3c(cn2)[C@H]2[C@@H](C3)[C@@H]2C(=O)O)c(F)cc1C(F)(F)F] | 576 | (5aR,6S,6aS)-3-((5-(6-(3,4-dihydroxy-3-methyl-butoxy)-2-methylpyridin-3-yl)-2-fluoro-4-(tri-fluoromethyl)benzyl)-oxy)-5,5a,6,6a-tetra-hydro-cyclopropa[4,5]-cyclopenta[1,2-c]-pyridine-6-carboxylic acid | 577 |
| 21 | 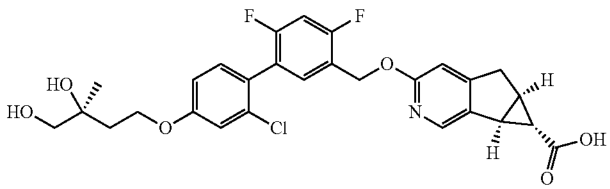 [SMILES: C[C@@](O)(CO)CCOc1ccc(-c2cc(COc3cc4c(cn3)[C@H]3[C@@H](C4)[C@@H]3C(=O)O)c(F)cc2F)c(Cl)c1] | 545 | (5aR,6S,6aS)-3-((2'-chloro-4'-((S)-3,4-dihydroxy-3-methyl-butoxy)-4,6-di-fluoro-[1,1'-biphenyl]-3-yl)methoxy)-5,5a,6,6a-tetrahydrocyclopropa[4,5]cyclopenta[1,2-c]pyridine-6-carboxylic acid | 546 |

Example 22

(5aR,6S,6aS)-3-((4,6-difluoro-4'-(3-hydroxy-2-(2-hydroxypropan-2-yl)-3-methylbutoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid

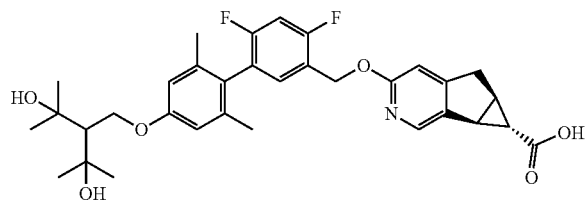 [SMILES: Cc1cc(OCC(C(C)(C)O)C(C)(C)O)cc(C)c1-c1cc(COc2cc3c(cn2)[C@H]2[C@@H](C3)[C@@H]2C(=O)O)c(F)cc1F]

Step A: 3-methylbut-2-en-1-yl benzoate

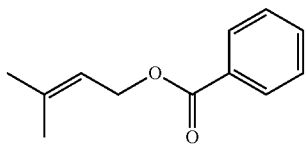

Benzoyl chloride (9.71 mL, 84 mmol) was added to a stirred, cooled mixture of 3-methylbut-2-en-1-ol (6 g, 69.7 mmol) in pyridine (30 ml) at 0° C. and the mixture was stirred at 20° C. for 16 hours. Then the mixture was quenched with water, and extracted with EtOAc. The combined organic layer was washed with 2 N aqueous HCl, dried over anhydrous Na₂SO₄, filtered, and the filtrate was concentrated in vacuo to give the crude product. The resulting residue was purified by chromatography over silica gel (eluting with PE) to give the title compound.

Step B: (3,3-dimethyloxiran-2-yl)methyl benzoate

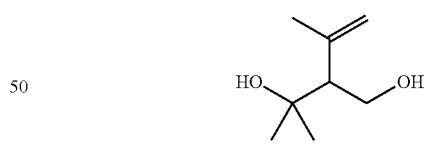

m-CPBA (7.65 g, 35.5 mmol) was added to a stirred, cooled mixture of 3-methylbut-2-en-1-yl benzoate (5 g, 23.65 mmol) in DCM (100 mL) at 0° C., and the mixture was stirred at 20° C. for 16 hours. Then the mixture was quenched with water and extracted with DCM. The combined organic layers were washed with saturated Na₂S₂O₃, dried over anhydrous Na₂SO₄ and filtered. The filtrate was concentrated in vacuo to give the crude product, which was purified by chromatography over silica gel (eluting with PE:EA=20:1 to 10:1) to provide the title compound.

Step C: 3-methyl-2-(prop-1-en-2-yl)butane-1,3-diol

Prop-1-en-2-ylmagnesium bromide (38.8 ml, 19.40 mmol, 0.5 M in THF) was added to a stirred, cooled mixture of copper(I) bromide-dimethyl sulfide (997 mg, 4.85 mmol) and dimethylsulfane (0.7 ml, 9.53 mmol) in Et₂O (10 mL) at −25° C., then a solution of (3,3-dimethyloxiran-2-yl) methyl benzoate (500 mg, 2.424 mmol) in Et₂O (5 mL) was added dropwise. The resulting mixture was stirred at −25° C. for 5 hours then allowed to warm to 20° C. and stirred for 16 hours. The mixture was poured into saturated NH₄Cl/NaOH (pH=8) at 0° C., and extracted with EtOAc. The combined organic layers were washed with brine, dried over anhydrous Na₂SO₄, and filtered. The filtrate was concentrated in vacuo to give the crude product which was purified by chromatography over silica gel (eluting with PE:EA=10:1 to 1:1) to give the title compound.

Step D: 2-(2-hydroxypropan-2-yl)-3-methylbut-3-en-1-yl 4-methylbenzenesulfonate

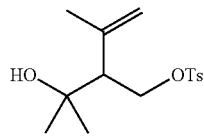

4-Methylbenzene-1-sulfonyl chloride (436 mg, 2.288 mmol) was added to a stirred, cooled mixture of 3-methyl-2-(prop-1-en-2-yl)butane-1,3-diol (300 mg, 2.080 mmol), triethylamine (0.870 ml, 6.24 mmol) and DMAP (50.8 mg, 0.416 mmol) in DCM (20 ml) at 0° C., and the resulting mixture was stirred at 20° C. for 16 hours. The mixture was quenched with water, and extracted with DCM. Then the combined organic layers were washed with brine, dried over anhydrous $Na_2SO_4$ and filtered. The filtrate was concentrated in vacuo. The resulting residue was purified by chromatography over silica gel (eluting with PE:EA=10:1 to 2:1) to give the title compound.

Step E: 3-((4-bromo-3,5-dimethylphenoxy)methyl)-2,4-dimethylpent-4-en-2-ol

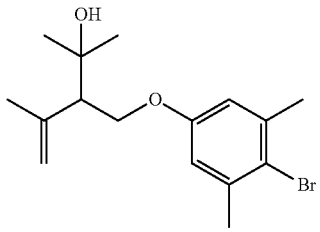 [SMILES: C=C(C)C(COc1cc(C)c(Br)c(C)c1)C(C)(C)O]

A mixture of 2-(2-hydroxypropan-2-yl)-3-methylbut-3-en-1-yl 4-methylbenzenesulfonate (356 mg, 1.194 mmol), 4-bromo-3,5-dimethylphenol (200 mg, 0.995 mmol) and $Cs_2CO_3$ (648 mg, 1.989 mmol) in NMP (5 mL) was stirred at 100° C. for 16 hours under nitrogen. After cooling to room temperature, the mixture was diluted with EtOAc. The organic layer was separated, and washed with water. The water layer was separated and extracted with EtOAc. The combined organic layers were washed with brine, dried over anhydrous $Na_2SO_4$, filtered and concentrated in vacuo to afford the title compound, which was used in the next step without further purification.

Step F: 4-(4-bromo-3,5-dimethylphenoxy)-2-methyl-3-(2-methyloxiran-2-yl)butan-2-ol

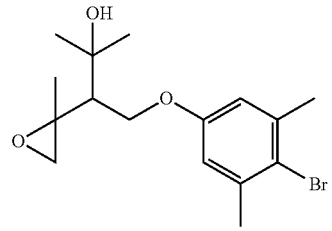 [SMILES: Cc1cc(OCC(C(C)(C)O)C2(C)CO2)cc(C)c1Br]

m-CPBA (222 mg, 1.029 mmol) was added to a stirred, cooled mixture of 3-((4-bromo-3,5-dimethylphenoxy)methyl)-2,4-dimethylpent-4-en-2-ol (374 mg, 0.686 mmol) in DCM (5 mL) at 0° C. and the mixture was stirred at 20° C. for 16 hours. The mixture was then quenched with water, and extracted with DCM. The combined organic layers were washed with saturated $Na_2S_2O_3$, dried over anhydrous $Na_2SO_4$, and filtered. The filtrate was concentrated in vacuo to give the title compound, which was used in the next step without further purification.

Step G: 3-((4-bromo-3,5-dimethylphenoxy)methyl)-2,4-dimethylpentane-2,4-diol

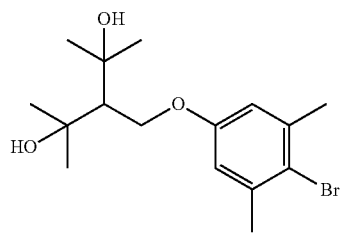 [SMILES: Cc1cc(OCC(C(C)(C)O)C(C)(C)O)cc(C)c1Br]

$LiAlH_4$ (39.2 mg, 1.032 mmol) was added to a stirred, cooled mixture of 4-(4-bromo-3,5-dimethylphenoxy)-2-methyl-3-(2-methyloxiran-2-yl)butan-2-ol (253 mg, 0.516 mmol) in THF (5 mL) at 0° C. and the mixture was stirred at 20° C. for 16 hours. Then the mixture was quenched with water (0.2 mL), NaOH (15%) (0.2 mL) and water (0.6 mL) again, and stirred for 15 minutes. The resulting mixture was filtered and the filtrate was concentrated in vacuo to give a residue, which was purified by chromatography over silica gel (eluting with PE:EA=2:1) to afford the title compound.

Step H: (5aR,6S,6aS)-tert-butyl 3-((4,6-difluoro-4'-(3-hydroxy-2-(2-hydroxypropan-2-yl)-3-methylbutoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate

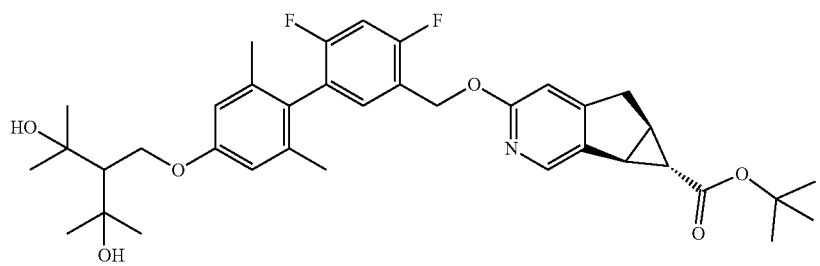 [SMILES: Cc1cc(OCC(C(C)(C)O)C(C)(C)O)cc(C)c1-c1cc(COc2cc3c(cn2)[C@H]2[C@@H](C3)[C@@H]2C(=O)OC(C)(C)C)c(F)cc1F]

A mixture of 3-((4-bromo-3,5-dimethylphenoxy)methyl)-2,4-dimethylpentane-2,4-diol (100 mg, 0.290 mmol), intermediate 11 (145 mg, 0.290 mmol), K$_2$CO$_3$ (80 mg, 0.579 mmol) and Pd(dtbpf)Cl$_2$ (18.88 mg, 0.029 mmol) in THF (2 ml) and water (0.5 ml) was charged in a sealed tube and heated at 100° C. with microwave irradation for 30 mins under N$_2$ protection. After cooling to room temperature, the mixture was filtered through Celite™, and rinsed with EtOAc. The organic layer was washed with water, and the water layer was extracted with EtOAc. The combined organic layers were washed with brine, dried over anhydrous Na$_2$SO$_4$, and filtered. The filtrate was concentrated in vacuo to give a residue, which was purified via silica gel preparative TLC (eluting with PE:EA=3:1) to give the title compound. MS (ESI) m/e (M+H$^+$): 638.2.

Step I: (5aR,6S,6aS)-3-((4,6-difluoro-4'-(3-hydroxy-2-(2-hydroxypropan-2-yl)-3-methylbutoxy)-2',6'-dimethyl-[1,1'-biphenyl]-3-yl)methoxy)-5,5a,6,6a-tetrahydro-cyclopropa-[4,5]cyclopenta[1,2-c]pyridine-6-carboxylic acid

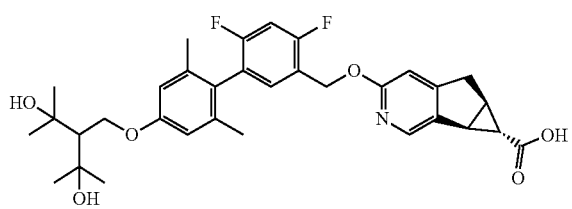 [SMILES: Cc1cc(OCC(C(C)(C)O)C(C)(C)O)cc(C)c1-c1cc(COc2cc3c(cn2)[C@H]2[C@@H](C3)[C@@H]2C(=O)O)c(F)cc1F]

A mixture of (5aR,6S,6aS)-tert-butyl 3-((4,6-difluoro-4'-(3-hydroxy-2-(2-hydroxypropan-2-yl)-3-methylbutoxy)-2',6'-dimethyl-[1,1'-biphenyl]-3-yl)methoxy)-5,5a,6,6a-tetrahydrocyclopropa[4,5]cyclopenta[1,2-c]pyridine-6-carboxylate (63 mg, 0.099 mmol) and LiOH.H$_2$O (124 mg, 2.96 mmol) in THF (4 ml), MeOH (1 ml) and water (1 ml) was stirred at 50° C. for 16 hours. After cooling to room temperature, the mixture was acidified with 2N HCl to pH=3, and then extracted with EtOAc. The combined organic layers were washed with brine, dried over anhydrous Na$_2$SO$_4$, and filtered. The filtrate solvent was evaporated under reduced pressure to give a residue, which was purified by reverse preparative HPLC (preparative HPLC on a GILSON 281 instrument fitted with a Diamonsil 150*20 mm*5um using water and acetonitrile as the eluents. Mobile phase A: water (containing 0.1% TFA, v/v), mobile phase B: acetonitrile. Gradient: 48-78% B, 0-10 min; 100% B, 10.5-12.5 min; 5% B, 13-15 min) to give the title compound. $^1$H NMR (400 MHz, MeOD-d$_4$) δ: 8.08 (s, 1H), 7.26 (t, J=8.22 Hz, 1H), 7.07 (t, J=9.68 Hz, 1H), 6.83 (s, 1H), 6.67 (s, 2H), 5.38 (s, 2H), 3.99 (d, J=4.30 Hz, 2H), 3.25 (br. s., 1H), 3.08 (d, J=18.98 Hz, 1H), 2.94 (d, J=4.89 Hz, 1H), 2.43-2.47 (m, 1H), 2.08 (t, J=4.11 Hz, 1H), 1.93 (s, 6H), 1.42 (s, 6H), 1.33 (s, 6H), 1.16 (br. s., 1H). MS (ESI) m/e (M+H$^+$): 582.2.

Example 23

(5aR,6S,6aS)-3-((4'-(3,4-dihydroxy-3-methylbutyl)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid

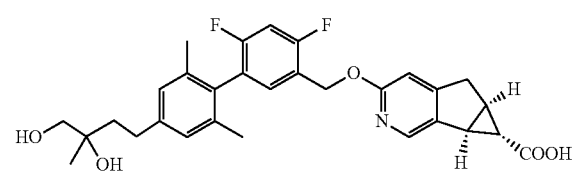 [SMILES: Cc1cc(CCC(C)(O)CO)cc(C)c1-c1cc(COc2cc3c(cn2)[C@H]2[C@@H](C3)[C@@H]2C(=O)O)c(F)cc1F]

Step A: (4-bromo-3, 5-dimethylphenyl) methanol

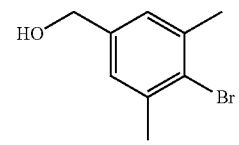

NaBH$_4$ (0.710 g, 18.77 mmol) was added to a stirred, cooled mixture of 4-bromo-3,5-dimethyl-benzaldehyde (2 g, 9.39 mmol) in MeOH (20 mL) at 0° C. Then the mixture was allowed to warm to rt and stirred for 2 h. The mixture was quenched by adding 1N HCl dropwise until the mixture pH=7, and then extracted with DCM. The organic layer was separated, dried over anhydrous Na$_2$SO$_4$, filtered and concentrated in vacuo to give the title compound, which was used in the next step without further purification.

Step B: 2-bromo-5-(bromomethyl)-1,3-dimethylbenzene

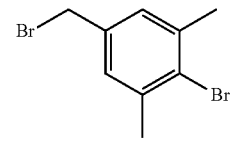

Phosphorous tribromide (0.539 ml, 5.72 mmol) was added to a stirred, mixture of (4-bromo-3, 5-dimethylphenyl) methanol (2.05 g, 9.53 mmol) in DCM (20 mL) at 0° C., and the mixture was allowed to warm to rt and stirred for 2 h. Then water (50 mL) was added to the mixture at 0° C., and the mixture was extracted with DCM. The organic layer was separated, washed with brine, dried with anhydrous Na$_2$SO$_4$, and filtered. The filtrate solvent was concentrated in vacuo to give the title compound, which was used in the next step without further purification.

Step C: 4-(4-bromo-3,5-dimethylphenyl)butan-2-one

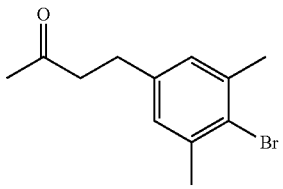

A mixture of 2-bromo-5-(bromomethyl)-1,3-dimethylbenzene (2.45 g, 8.81 mmol), pentane-2,4-dione (0.882 g, 8.81 mmol) and K₂CO₃ (1.218 g, 8.81 mmol) in MeOH (25 ml) was stirred at 80° C. for 16 h. Then the mixture was concentrated in vacuo, and diluted with water and EtOAc. The aqueous layer was separated and extracted with EtOAc. The combined organic layers were washed with brine, dried with anhydrous Na₂SO₄, filtered and concentrated in vacuo to give a residue, which was purified via silica gel chromatography (eluting with PE to PE:EA=92:8) to give the title compound.

Step D: 2-bromo-1,3-dimethyl-5-(3-methylbut-3-en-1-yl)benzene

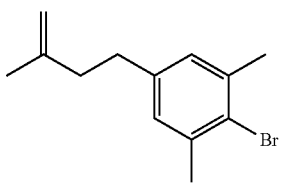

To a mixture of PPh₃CH₃Br (3.36 g, 9.41 mmol) in THF (15 mL) was added dropwise t-BuOK (8.82 ml, 8.82 mmol), followed by the dropwise addition of 4-(4-bromo-3,5-dimethylphenyl)-butan-2-one (1.5 g, 5.88 mmol) in THF (5 mL) The reaction mixture was stirred at 20° C. for 15 h, then concentrated in vacuo and diluted with water and EtOAc. The aqueous layer was separated and extracted with EtOAc. The combined organic layers were washed with brine, dried over anhydrous Na₂SO₄, filtered and concentrated in vacuo. The resulting residue was purified by silica gel chromatography (eluting with PE to PE:EA=95:5) to give the title compound.

Step E: 4-(4-bromo-3,5-dimethylphenyl)-2-methylbutane-1,2-diol

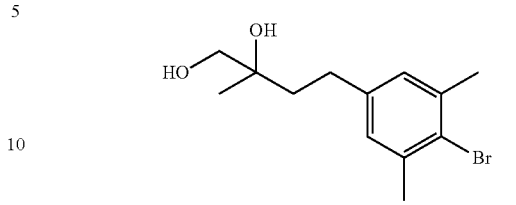

To a mixture of 2-bromo-1,3-dimethyl-5-(3-methylbut-3-en-1-yl)benzene (1.0 g, 3.95 mmol) and N-methylmorpholine N-oxide (1.388 g, 11.85 mmol) in acetone (15 ml) and water (1.5 ml) was added OsO₄ (0.100 g, 0.395 mmol) and the resulting mixture was stirred at 22° C. for 18 h. Then the mixture was quenched by adding Na₂S₂O₃ and stirred for 1 h. The resulting mixture was diluted with water and EtOAc. The aqueous layer was separated, extracted with EtOAc, dried over anhydrous Na₂SO₄, filtered and concentrated in vacuo to give the title compound, which was used in the next step without further purification.

Step F: (5aR,6S,6aS)-tert-butyl 3-((4'-(3,4-dihydroxy-3-methylbutyl)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate

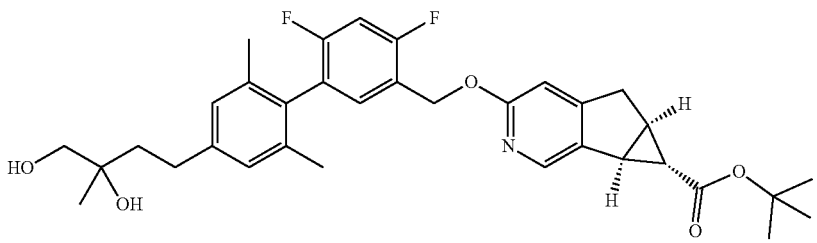 [SMILES: Cc1cc(CCC(C)(O)CO)cc(C)c1-c1cc(COc2cc3c(cn2)[C@H]2[C@@H](C3)[C@@H]2C(=O)OC(C)(C)C)c(F)cc1F]

To a mixture of 4-(4-bromo-3,5-dimethylphenyl)-2-methylbutane-1,2-diol (200 mg, 0.696 mmol), intermediate 11 (383 mg, 0.766 mmol), K₂CO₃ (289 mg, 2.089 mmol) in THF (3 ml) and water (1 ml) was added Pd(dtbpf)Cl₂ (45.4 mg, 0.070 mmol). The resulting mixture was sealed in a 10 mL vial/autoclave and stirred at 100° C. for 0.5 h under N₂ protection. After cooling to room temperature, the mixture was filtered over Celite', and then diluted with EtOAc and water. The aqueous layer was separated and extracted with EOAc. The combined organic layers were washed with brine, dried over anhydrous Na₂SO₄, filtered and concentrated in vacuo. The resulting residue was purified by prep-HPLC to give the title compound. MS (ESI) m/e (M+H⁺): 580.2.

Step G: (5aR,6S,6aS)-3-((4'-(3,4-dihydroxy-3-methylbutyl)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid

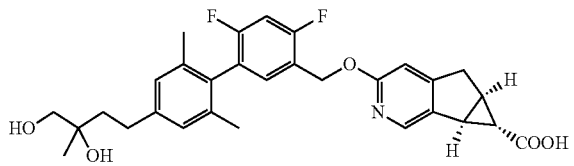 [SMILES: Cc1cc(CCC(C)(O)CO)cc(C)c1-c1cc(COc2cc3c(cn2)[C@H]2[C@@H](C3)[C@@H]2C(=O)O)c(F)cc1F]

LiOH.H$_2$O (213 mg, 5.07 mmol) was added to a stirred, solution of (5aR,6S,6aS)-tert-butyl 3-((4'-(3,4-dihydroxy-3-methylbutyl)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate (245 mg, 0.423 mmol) in water (0.5 mL), THF (0.5 mL) and MeOH (2 mL) The reaction was stirred at 50° C. for 13 h, then the reaction was cooled and acidified with 1N HCl to pH=3. Then the reaction mixture was extracted with EtOAc. The combined organic layers were washed with brine, dried over anhydrous Na$_2$SO$_4$, filtered and concentrated in vacuo. The resulting residue was purified via silica gel preparative TLC (eluting with ethyl acetate) to afford the title compound. $^1$H NMR (400 MHz, CD$_3$OD-d$_4$) δ: 8.04 (s, 1H), 7.22 (t, J=8.0 Hz, 1H), 7.05 (t, J=9.6 Hz, 1H), 6.95 (s, 2H), 6.67 (s, 1H), 5.35 (s, 2H), 3.41 (s, 2H), 3.26-3.17 (m, 1H), 3.07-2.98 (m, 1H), 2.90 (d, J=5.2 Hz, 1H), 2.65-2.59 (m, 2H), 2.46-2.38 (m, 1H), 1.92 (s, 6H), 1.82-1.68 (m, 2H), 1.20 (s, 3H), 1.11 (br. s., 1H). MS (ESI) m/e (M+H$^+$): 524.2.

Example 24

Sodium (5aR,6S,6aS)-3-((4'-((S)-3,4-dihydroxybutoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate

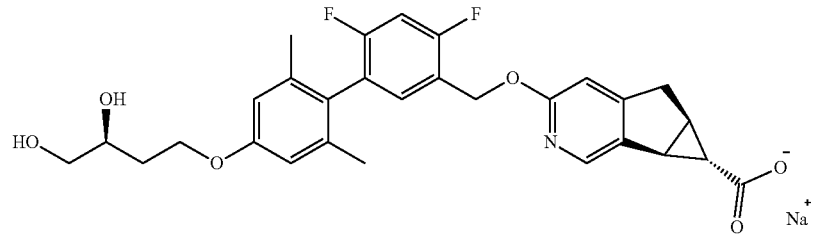 [SMILES: Cc1cc(OCC[C@H](O)CO)cc(C)c1-c1cc(COc2cc3c(cn2)[C@H]2[C@@H](C3)[C@@H]2C(=O)[O-])c(F)cc1F ; [Na+]]

Step A: (S)-4-(2-(4-bromo-3, 5-dimethylphenoxy)ethyl)-2, 2-dimethyl-1, 3-dioxolane

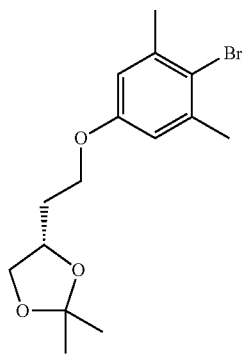 [SMILES: Cc1cc(OCC[C@H]2COC(C)(C)O2)cc(C)c1Br]

To a solution of 4-bromo-3,5-dimethylphenol (15 g, 74.6 mmol), (4S)-(+)-4-(2-hydroxyethyl)-2,2-dimethyl-1,3-dioxolane (14.18 g, 97 mmol) and tris-N-butylphosphine (24.22 ml, 97 mmol) in THF (200 ml) at 0° C. was added DIAD (18.86 ml, 97 mmol). The reaction mixture was warmed to room temperature and stirred overnight for 3 days. Then the mixture was concentrated in vacuo and the resulting residue was purified via silica gel chromatography (eluting with hexanes to hexanes:ethyl acetate=75:25) to provide the title compound.

Step B: (S)-4-(4-bromo-3,5-dimethylphenoxy)butane-1,2-diol

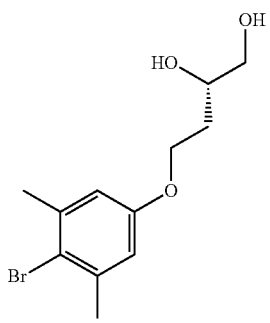 [SMILES: Cc1cc(OCC[C@H](O)CO)cc(C)c1Br]

To a solution of (S)-4-(2-(4-bromo-3,5-dimethylphenoxy)ethyl)-2,2-dimethyl-1,3-dioxolane (8.1 g, 24.60 mmol) in MeOH (700 ml) and water (30 ml) at room temperature was added hydrochlorid acid (4M in Dioxane, 7.38 ml, 29.5 mmol). The reaction mixture was stirred overnight, then concentrated in vacuo. The resulting mixture was neutralized with saturated aqueous NaHCO$_3$, and extracted with EtOAc. The combined organic layers were washed with brine, dried over anhydrous Na$_2$SO$_4$, filtered and concentrated in vacuo to provide the title compound, which was used directly in the next step. MS (ESI) m/e (M+H$^+$): 289.2.

Step C: (5aR,6S,6aS)-tert-butyl 3-((4'-((S)-3,4-dihydroxybutoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate

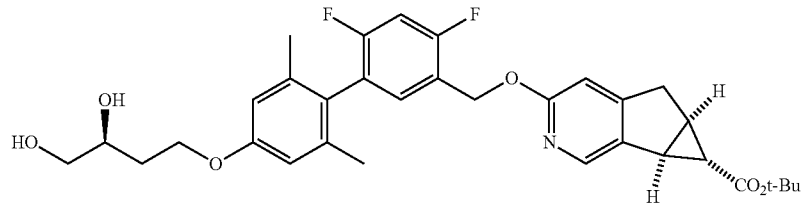 [SMILES: Cc1cc(OCC[C@H](O)CO)cc(C)c1-c1cc(COc2cc3c(cn2)[C@H]2[C@@H](C3)[C@@H]2C(=O)OC(C)(C)C)c(F)cc1F]

To a mixture of X-Phos Second Generation Precatalyst (473 mg, 0.601 mmol), intermediate 11 (3.1 g, 6.21 mmol) and (S)-4-(4-bromo-3,5-dimethylphenoxy)butane-1,2-diol (2.154 g, 7.45 mmol) under $N_2$ was added degassed THF (60 ml) and $K_3PO_4$ (18.62 ml, 18.62 mmol). The reaction was then stirred at 40° C. for 45 min, and stirred overnight at room temperature. Then the reaction was diluted with EtOAc, washed with water, dried over anhydrous $Na_2SO_4$, filtered and concentrated in vacuo. The resulting residue was purified by chromatography over silica gel (eluting with hexanes to ethyl acetate) to give the title compound. MS (ESI) m/e (M+H$^+$): 581.6.

Step D: Sodium (5aR,6S,6aS)-3-((4'-((S)-3,4-dihydroxybutoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate

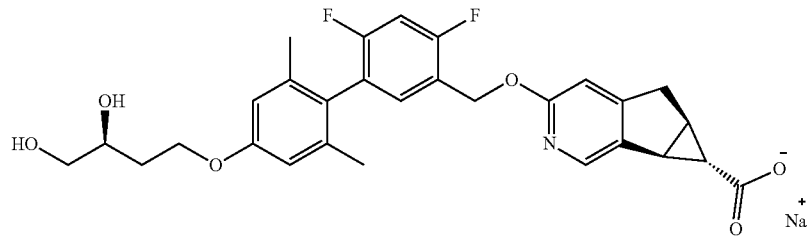 [SMILES: Cc1cc(OCC[C@H](O)CO)cc(C)c1-c1cc(COc2cc3c(cn2)[C@H]2[C@@H](C3)[C@@H]2C(=O)[O-])c(F)cc1F ; [Na+]]

To a solution of (5aR,6S,6aS)-tert-butyl 3-((4'-((S)-3,4-dihydroxybutoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylate (3.57 g, 6.14 mmol) in THF (60 ml) and MeOH (60 ml) at room temperature was added 10 N NaOH (1.841 ml, 18.41 mmol). The mixture was warmed to 40° C. and stirred for 3 h, and then stirred at rt overnight. Then NaOH (10 N, 0.4 ml) was added and the reaction was stirred at rt overnight. The mixture was then quenched at room temperature with 1N HCl and extracted with EtOAc. The combined organic layers were washed with brine, dried over $Na_2SO_4$, filtered and concentrated in vacuo. The resulting residue was purified via silica gel column (120 g, eluting with 0-20% MeOH in DCM) to give the title compound as the acid. To a solution of crude title compound in acetonitrile (40 ml) at room temperature was added NaOH (3.81 ml, 3.81 mmol) and the mixture was lyophilized to give the title compound as the sodium salt. ($^1$HNMR (500 MHz, CD3OD) δ: 7.98 (S, 1H), 7.23 (t, 1H, J=8.3 Hz), 7.08 (t, 1H, J=9.3 Hz), 6.69 (s, 2H), 6.64 (s, 1H), 5.34 (s, 2H), 4.12 (broad multiplet, 2H), 3.88 (broad multiplet, 1H), 3.54 (m, 2H0, 3.18 (dd, 1H, $J_{13}$=18.6 Hz, $J_{12}$=6.4 Hz), 2.98 (s, 1H), 2.75 (d, 1H, J=4.9 Hz), 2.30 (s, 1H), 1.94 (s, 6H), 1.81 (1H). (m/z): 525.5 (M+H).

Examples 25 and 26 were prepared in a similar manner to Example 24 using the appropriate intermediates and commercially available starting materials.

| Example | Structure | M.W. | Compound Name | LC/MS (ESI) observed [M + 1]+ |
|---|---|---|---|---|
| 25 | ![structure] | 524 | (5aR,6S,6aS)-3-((4'-((R)-3,4-dihydroxybutoxy)-4,6-difluoro-2',6'-dimethyl-[1,1'-biphenyl]-3-yl)methoxy)-5,5a,6,6a-tetrahydrocyclopropa[4,5]cyclopenta[1,2-c]pyridine-6-carboxylic acid | 525 |

-continued

| Example | Structure | M.W. | Compound Name | LC/MS (ESI) observed [M + 1]+ |
|---|---|---|---|---|
| 26 | (structure) | 545 | (5aR,6S,6aS)-3-((6-chloro-4'-((R)-3,4-dihydroxybutoxy)-4,5,-difluoro-2'-methyl-[1,1'-biphenyl]-3-yl)methoxy)-5,5a,6,6a-tetrahydrocyclopropa[4,5]cyclopenta[1,2-c]pyridine-6-carboxylic acid | 546 |

Biological Assays

Generation of GPR40-Expressing Cells:

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

FLIPR Assays:

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 µL medium/well. The cells were incubated with 20 µl/well of the assay buffer (HBSS, 0.1% BSA, 20 mM HEPES, 2.5 mM probenecid, pH 7.4) containing 8 µM fluo-4, AM, 0.08% pluronic acid at room temperature for 100 minutes. Fluorescence output was measured using FLIPR. Compounds were dissolved in DMSO and diluted to desired concentrations with assay buffer. 13.3 µL/well of compound solution was added.

The compounds of the present invention, including the compounds in Examples 1-16, have $EC_{50}$ values less than 100 nanomolar (nM) in the FLIPR assay described above. The compounds in Examples 1-16 have the $EC_{50}$ values in the FLIPR assay listed in Table I.

Inositol Phosphate Turnover Assay 1:

The assay was performed in 96-well format. HEK cells stably expressing human GPR40 were plated to be 60-80% confluent within 72 h. After 72 h, the plates were aspirated and the cells washed with inositol-free DMEM (ICN). The wash media was replaced with 150 µL of 3H-inositol labeling media (inositol-free media containing 0.4% human albumin or 0.4% mouse albumin, 1× pen/strep antibiotics, glutamine, 25 mM HEPES to which was added 3H-myo-inositol NEN #NET114A 1 mCi/mL, 25 Ci/mmol diluted 1:150 in loading media with a final specific radioactivity of 1 µCi/150 µL). Alternatively, the human and mouse albumin can be added after the overnight labeling step before the addition of LiCl.

The assay was typically run the next day after 18 h labeling. On the day of the assay, 5 µL of 300 mM LiCl was added to all wells and incubated at 37 degrees for 20 min 0.75 µL of 200× compounds were added and incubated with the cells for 60 min at 37 degrees. The media was then aspirated off and the assay terminated with the addition of 60 µL 10 mM formic acid. The cells were lysed for 60 min at room temperature. 15-30 µL of lysate was mixed with 70 µL/1 mg YSi SPA beads (Amersham) in clear bottom Isoplates. The plates were shaken for 2 h at room temperature. Beads were allowed to settle and the plates were counted in the Wallac Microbeta.

The compounds of the present invention, including the compounds in Examples 1-16, 18, 24 and 25 have $EC_{50}$ values less than 3000 nanomolar (nM) in the Inositol Phosphate Turnover (IP1) Assay 1 described above. The compounds in Examples 1-16, 18, 24 and 25 have the $EC_{50}$ values in the Inositol Phosphate Turnover (IP1) Assay 1 listed in Table I.

Inositol Phosphate Turnover (IP1) Assay 2:

The assay was performed in 384-well format. HEK cells stably expressing human GPR40 were plated at 15,000 cells per well in growth medium (DMEM/10% fetal calf serum). Cell plates were then incubated 16 hours at 37 degrees in a 5% $CO_2$ incubator.

Measurement of Inositol Phosphate Turnover (IP1) was performed using the CisBio IP-One kit (Part number 62IPA-PEB). After the 16 hour incubation, the cells were washed with HEPES buffer and 10 ul of stimulation buffer (prepared as described in the kit) was added to each well. In a separate plate, compounds were diluted in DMSO (400-fold over the final concentration in the assay well) and 25 nl was acoustically transferred to the appropriate well in the assay cell plate. The plates were then incubated for 60 minutes at 37 degrees. 10 ul of detection buffer (also prepared as described in the IP-One kit) was added to each well and the plates were incubated for 60 minutes in the dark. The plates were then read in a Perkin Elmer EnVision or equivalent reader able to measure FRET. Fluorescent ratio of emission at 665 and 620 nm was then converted to IP1 concentration by back calculating from an IP1 standard curve prepared at the time of the assay.

The compounds of the present invention, including the compounds in Examples 17 and 19-26, have $EC_{50}$ values less than 3000 nanomolar (nM) in the Inositol Phosphate Turnover (IP1) Assay 2 described above. The compounds in Examples 17 and 19-26 have the $EC_{50}$ values in the Inositol Phosphate Turnover (IP1) Assay 2 listed in Table I.

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood.

Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

TABLE I. $EC_{50}$ values (nM) for Examples in Human GPR40 FLIPR and IP1 Assays

| Example Number | Human GPR40, FLIPR, $EC_{50}$, nM | Human GPR40 IP1, Assay 1, $EC_{50}$, nM | Human GPR40 IP1 Assay 2, $EC_{50}$, nM |
|---|---|---|---|
| 1 | 16.75 | 9.889 | ND |
| 2 | 5.746 | 2.981 | ND |
| 3 | 1.524 | 4.949 | ND |
| 4 | 14.38 | 5.245 | ND |
| 5 | 24.93 | 6.243 | ND |
| 6 | 10.89 | 14.75 | ND |
| 7 | 11.23 | 11.39 | ND |
| 8 | 9.202 | 6.54 | ND |
| 9 | 6.894 | 11.12 | ND |
| 10 | 6.404 | 27.22 | ND |
| 11 | 16.66 | 17.61 | ND |
| 12 | 12.46 | 20.34 | ND |
| 13 | 9.658 | 5.941 | ND |
| 14 | 10.37 | 5.538 | ND |
| 15 | 4.884 | 7.966 | ND |
| 16 | ND | 10.4 | ND |
| 17 | ND | ND | 2.1 |
| 18 | ND | 19.2 | ND |
| 19 | ND | ND | 1.6 |
| 20 | ND | ND | 3.1 |
| 21 | ND | ND | 2.2 |
| 22 | ND | ND | 3.1 |
| 23 | ND | ND | 5.2 |
| 24 | ND | 4.6 | 1.3 |
| 25 | ND | 4.7 | 3.8 |
| 26 | ND | ND | 0.7 |

ND is not determined

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

The invention claimed is:
1. A compound of structural formula I:

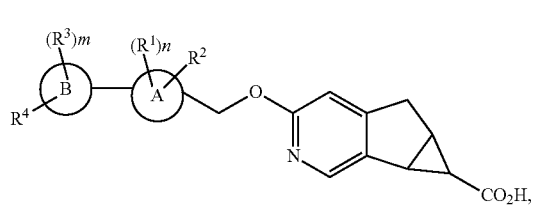

or a pharmaceutically acceptable salt thereof; wherein
A is phenyl;
B is selected from the group consisting of:
  (1) phenyl, and
  (2) pyridyl;
$R^1$ is selected from the group consisting of:
  (1) halogen,
  (2) —CN,
  (3) —$C_{1-6}$alkyl,
  (4) —$(CH_2)_r OC_{1-6}$alkyl,
  (5) —$(CH_2)_r C_{3-6}$cycloalkyl, and
  (6) —$(CH_2)_r$—O—$(CH_2)_r$—$C_{3-6}$cycloalkyl,
wherein each $CH_2$, —$C_{1-6}$alkyl, —$OC_{1-6}$alkyl and —$C_{3-6}$cycloalkyl is unsubstituted or substituted with one to four substituents selected from halogen, —$C_{1-6}$alkyl and —$(CH_2)_v$—$C_{3-6}$cycloalkyl;
$R^2$ is halogen;
$R^3$ when present is selected from the group consisting of:
  (1) halogen,
  (2) —$C_{1-6}$alkyl, and
  (3) —$(CH_2)_u$—$C_{3-6}$cycloalkyl,
wherein each $C_{1-6}$alkyl and $C_{3-6}$cycloalkyl is unsubstituted or substituted with one to three substituents selected from halogen;
$R^4$ is —$OC_{1-6}$alkyl, wherein $C_{1-6}$alkyl is unsubstituted or substituted with one, two, three or four substituents selected from $R^5$;
$R^5$ is selected from the group consisting of:
  (1) —$C_{1-6}$alkyl,
  (2) —$(CH_2)_s OH$, and

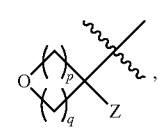

(3)

wherein each $CH_2$ and $C_{1-6}$alkyl is unsubstituted or substituted with one to three substituents selected from halogen;
wherein each $CH_2$, $C_{1-6}$alkyl and $C_{3-6}$cycloalkyl is unsubstituted or substituted with one to three substituents selected from halogen and $(CH_2)_w OH$;
Z is selected from:
  (1) hydrogen,
  (2) —$C_{1-6}$alkyl,
  (3) —$(CH_2)_s$—O—$C_{1-6}$alkyl, (4) —(CH$_2$)$_s$—OH,
(5) —(CH$_2$)$_s$SO$_2$C$_{1-6}$alkyl,
(6) —(CH$_2$)$_s$SO$_2$—(CH$_2$)$_t$—C$_{3-6}$cycloalkyl,
(7) —(CH$_2$)$_s$C$_{3-6}$cycloalkyl, and
(8) —(CH$_2$)$_s$—O—(CH$_2$)$_t$—C$_{3-6}$cycloalkyl, wherein each CH$_2$, C$_{1-6}$alkyl and C$_{3-6}$cycloalkyl is unsubstituted or substituted with one to three substituents selected from halogen;
m is 0, 1, 2 or 3;
n is 1 or 2;
p is 0, 1, 2 or 3;
q is 0,1, 2 or 3, provided that p+q is at least 2;
r is 0, 1, 2 or 3;
s is 0, 1, 2 or 3;
t is 0, 1, 2 or 3;
u is 0, 1, 2 or 3;
v is 0, 1, 2 or 3; and
w is 0, 1, 2 or 3.

2. The compound of claim 1 of structural formula I:

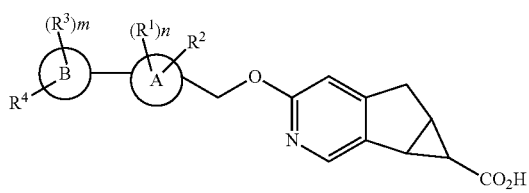

I or a pharmaceutically acceptable salt thereof; wherein
A is phenyl;
B is selected from the group consisting of:
  (1) phenyl, and
  (2) pyridyl;
R$^1$ is selected from the group consisting of:
  (1) halogen,
  (2) —CN,
  (3) —C$_{1-6}$alkyl,
  (4) —OC$_{1-6}$alkyl, and
  (5) —C$_{3-6}$cycloalkyl,
wherein each —C$_{1-6}$alkyl, —OC$_{1-6}$alkyl and —C$_{3-6}$cycloalkyl is unsubstituted or substituted with one to four substituents selected from halogen;
R$^2$ is halogen;
R$^3$ is selected from the group consisting of:
  (1) halogen,
  (2) —C$_{1-6}$alkyl, and
  (3) —C$_{3-6}$ cycloalkyl,
wherein each C$_{1-6}$alkyl and C$_{3-6}$cycloalkyl is unsubstituted or substituted with one to three substituents selected from halogen;
R$^4$ is —OC$_{1-6}$alkyl, wherein C$_{1-6}$alkyl is unsubstituted or substituted with one, two, three or four substituents selected from R$^5$;
R$^5$ is selected from the group consisting of:
  (1) —C$_{1-6}$alkyl,
  (2) —(CH$_2$)$_s$OH, and

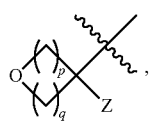

(3)

wherein each CH$_2$ and C$_{1-6}$alkyl is unsubstituted or substituted with one to three substituents selected from halogen;
Z is selected from:
  (1) hydrogen,
  (2) —C$_{1-6}$alkyl,
  (3) —(CH$_2$)$_s$—O—C$_{1-6}$alkyl,
  (4) —(CH$_2$)$_s$—OH, and
  (5) —(CH$_2$)$_s$C$_{3-6}$cycloalkyl,
wherein each CH$_2$, C$_{1-6}$alkyl and C$_{3-6}$cycloalkyl is unsubstituted or substituted with one to three substituents selected from halogen;
m is 0, 1, 2 or 3;
n is 1 or 2;
p is 0, 1, 2 or 3;
q is 0,1, 2 or 3, provided that p+q is at least 2; and
s is 0, 1, 2 or 3;
or a pharmaceutically acceptable salt thereof.

3. The compound according to claim 1 wherein A is:

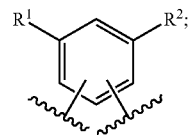

or a pharmaceutically acceptable salt thereof.

4. The compound according to claim 1 wherein A is

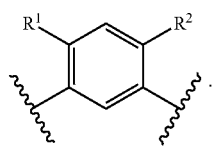

or a pharmaceutically acceptable salt thereof.

5. The compound according to claim 1 wherein B is phenyl, wherein phenyl is unsubstituted or substituted with one, two or three substituents selected from R$^3$;
or a pharmaceutically acceptable salt thereof.

6. The compound according to claim 1 wherein R$^1$ is selected from the group consisting of:
  (1) halogen, and
  (2) —C$_{1-6}$alkyl,
wherein —C$_{1-6}$alkyl is unsubstituted or substituted with one to four substituents selected from halogen; or a pharmaceutically acceptable salt thereof.

7. The compound according to claim 1 wherein R$^1$ is —C$_{1-6}$alkyl, wherein each —C$_{1-6}$alkyl is substituted with one, two or three substituents selected from halogen; or a pharmaceutically acceptable salt thereof.

8. The compound according to claim 1 wherein R$^2$ is F; or a pharmaceutically acceptable salt thereof.

9. The compound according to claim 1 wherein R$^3$ when present is selected from the group consisting of:
  (1) halogen, and
  (2) —C$_{1-6}$alkyl,
wherein each C$_{1-6}$alkyl is unsubstituted or substituted with one to three substituents selected from halogen; or a pharmaceutically acceptable salt thereof.

10. The compound according to claim 1 wherein R$^4$ is —OC$_{1-6}$alkyl, wherein C$_{1-6}$alkyl is substituted with one substituent selected from R$^5$; or a pharmaceutically acceptable salt thereof.

11. The compound according to claim 1 wherein $R^5$ is selected from the group consisting of:
(1) —$C_{1-6}$alkyl,
(2) —OH, and
(3)

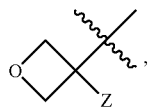

wherein each $C_{1-6}$alkyl is unsubstituted or substituted with one to three substituents selected from halogen; or a pharmaceutically acceptable salt thereof.

12. The compound according to claim 1 wherein Z is selected from:
(1) hydrogen,
(2) —$C_{1-6}$alkyl,
(3) —$(CH_2)_s$—O—$C_{1-6}$alkyl, and
(4) —$(CH_2)_s$—OH, wherein each $CH_2$, and $C_{1-6}$alkyl is unsubstituted or substituted with one to three substituents selected from halogen; or a pharmaceutically acceptable salt thereof.

13. The compound according to claim 1 wherein $R^5$ is selected from the group consisting of:
(1) —$C_{1-6}$alkyl, and
(2) —$(CH_2)_s$OH, wherein each $CH_2$ and $C_{1-6}$alkyl is unsubstituted or substituted with one to three substituents selected from halogen; or a pharmaceutically acceptable salt thereof.

14. The compound according to claim 1 wherein the absolute stereochemistry at the two stereogenic carbon centers is indicated below:

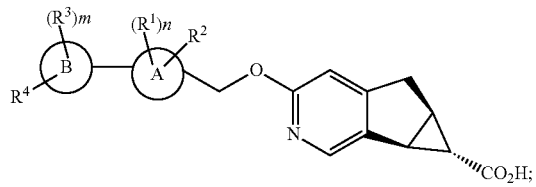

or a pharmaceutically acceptable salt thereof.

15. The compound according to claim 1 wherein:
A is phenyl;
B is phenyl or pyridyl;
$R^1$ is selected from the group consisting of:
(1) halogen, and
(2) —$C_{1-6}$alkyl,
wherein —$C_{1-6}$alkyl is unsubstituted or substituted with one to four substituents selected from halogen;
$R^2$ is halogen;
$R^3$ when present is selected from the group consisting of:
(1) halogen, and
(2) —$C_{1-6}$alkyl,
wherein each $C_{1-6}$alkyl is unsubstituted or substituted with one to three substituents selected from halogen;
$R^4$ is —$OC_{1-6}$alkyl, wherein $C_{1-6}$alkyl is substituted with one substituent selected from $R^5$;

$R^5$ is selected from the group consisting of:
(1) —$C_{1-6}$alkyl,
(2) —$(CH_2)_s$OH, and

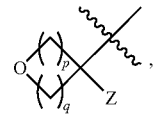

wherein each $CH_2$ and $C_{1-6}$alkyl is unsubstituted or substituted with one to three substituents selected from halogen; and
Z is selected from:
(1) hydrogen,
(2) —$C_{1-6}$alkyl,
(3) —$(CH_2)_s$—O—$C_{1-6}$alkyl, and
(4) —$(CH_2)_s$—OH,
wherein each $CH_2$, and $C_{1-6}$alkyl is unsubstituted or substituted with one to three substituents selected from halogen;
m is 0, 1, 2 or 3;
n is 1 or 2;
p is 0, 1, 2 or 3;
q is 0, 1, 2 or 3, provided that p+q is at least 2; and
s is 0, 1, 2 or 3;
or a pharmaceutically acceptable salt thereof.

16. The compound according to claim 1 wherein:
A is:

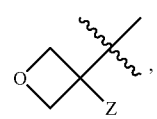

B is phenyl or pyridyl;
$R^1$ is selected from the group consisting of:
(1) halogen, and
(2) —$C_{1-6}$alkyl,
wherein —$C_{1-6}$alkyl is unsubstituted or substituted with one to four substituents selected from halogen;
$R^2$ is halogen;
$R^3$ when present is selected from the group consisting of:
(1) halogen, and
(2) —$C_{1-6}$alkyl,
wherein each $C_{1-6}$alkyl is unsubstituted or substituted with one to three substituents selected from halogen;
$R^4$ is —$OC_{1-6}$alkyl, wherein $C_{1-6}$alkyl is substituted with one substituent selected from $R^5$;
$R^5$ is selected from the group consisting of:
(1) —$C_{1-6}$alkyl,
(2) —OH, and (3)

wherein each $C_{1-6}$alkyl is unsubstituted or substituted with one to three substituents selected from halogen;

Z is —(CH₂)$_s$—OH;
m is 0, 1, 2 or 3; and
or a pharmaceutically acceptable salt thereof.
17. The compound according to claim 1 wherein
A is

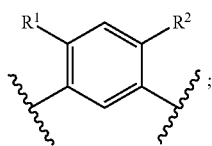

B is phenyl;
R$^1$ is —C$_{1-6}$alkyl, wherein each —C$_{1-6}$alkyl is substituted with one, two or three substituents selected from halogen;
R$^2$ is F;
R$^3$ when present is selected from the group consisting of:
  (1) halogen, and
  (2) —C$_{1-6}$alkyl,
wherein each C$_{1-6}$alkyl is unsubstituted or substituted with one to three substituents selected from halogen;
R$^4$ is —OC$_{1-6}$alkyl, wherein C$_{1-6}$alkyl is substituted with one substituent selected from R$^5$;
R$^5$ is selected from the group consisting of:
  (1) —C$_{1-6}$alkyl, and
  (2) —(CH₂)$_s$OH,
wherein each CH₂ and C$_{1-6}$alkyl is unsubstituted or substituted with one to three substituents selected from halogen;
m is 0, 1, 2 or 3; and
or a pharmaceutically acceptable salt thereof.
18. A compound selected from:

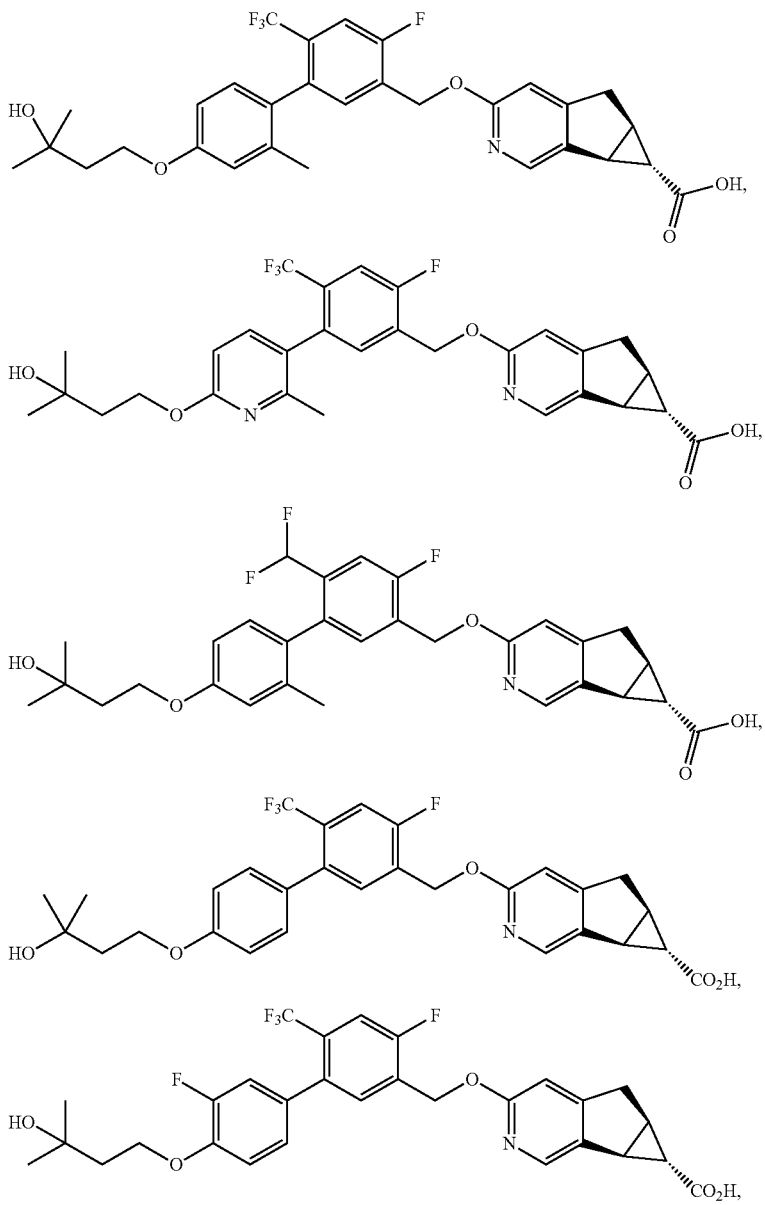

-continued
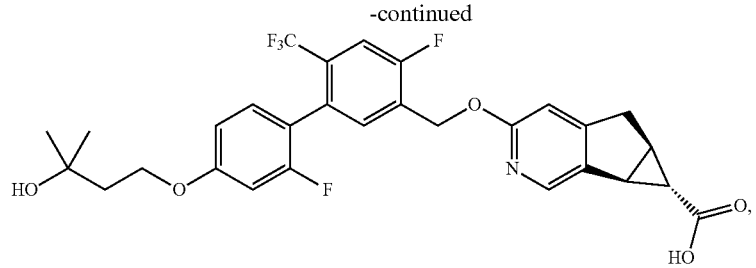
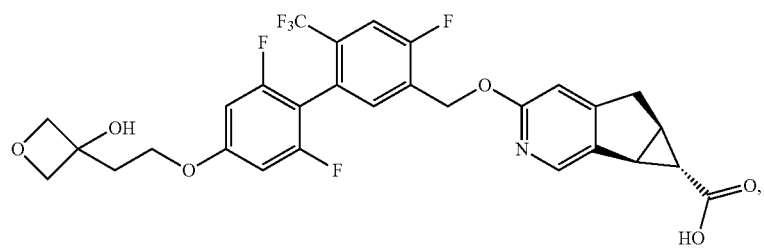
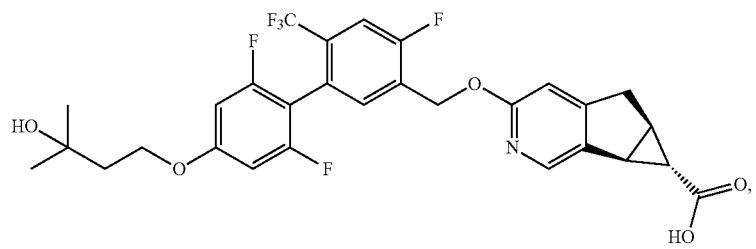
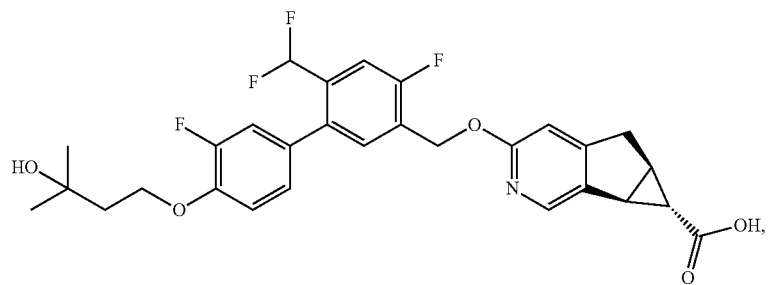
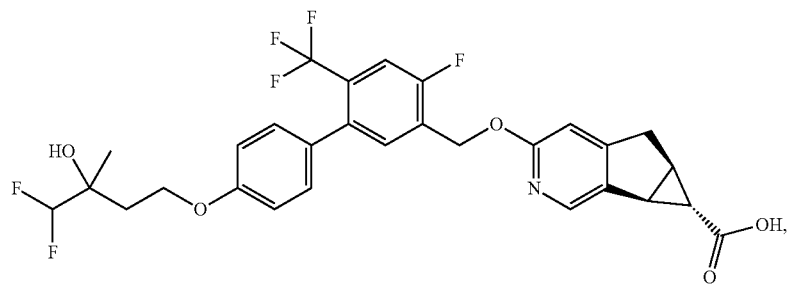
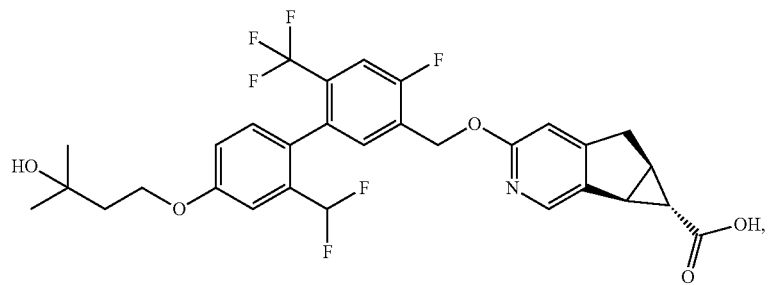

or a pharmaceutically acceptable salt thereof.

19. A pharmaceutical composition comprising a compound of claim 1, or a pharmaceutically acceptable salt thereof, and a pharmaceutically acceptable carrier.

20. A method of treating type 2 diabetes mellitus in a patient in need of treatment comprising the administration to the patient of a therapeutically effective amount of a compound of claim 1, or a pharmaceutically acceptable salt thereof.

21. A pharmaceutical composition comprising
(1) a compound of claim 1 or a pharmaceutically acceptable salt thereof;
(2) one or more compounds selected from the group consisting of:
  (a) PPAR gamma agonists and partial agonists;
  (b) biguanides;
  (c) protein tyrosine phosphatase-1B (PTP-1B) inhibitors;
  (d) dipeptidyl peptidase IV (DP-IV) inhibitors;
  (e) insulin or an insulin mimetic;
  (f) sulfonylureas;
  (g) α-glucosidase inhibitors;
  (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA: cholesterol acyltransferase (ACAT) inhibitors, (vii) CETP inhibitors, and (viii) phenolic anti-oxidants;
  (i) PPARα/γ dual agonists,
  (j) PPARδ agonists,
  (k) antiobesity compounds,
  (l) ileal bile acid transporter inhibitors;
  (m) anti-inflammatory agents;
  (n) glucagon receptor antagonists;
  (o) GLP-1;
  (p) GIP-1;
  (q) GLP-1 analogs;
  (r) HSD-1 inhibitors;
  (s) SGLT 1 inhibitors; and
  (t) SGLT 2 inhibitors; and
(3) a pharmaceutically acceptable carrier.

22. A pharmaceutical composition comprising a compound according to claim 1, or a pharmaceutically acceptable salt thereof, and a compound selected from simvastatin, ezetimibe and sitagliptin; and a pharmaceutically acceptable carrier.

23. A compound selected from:

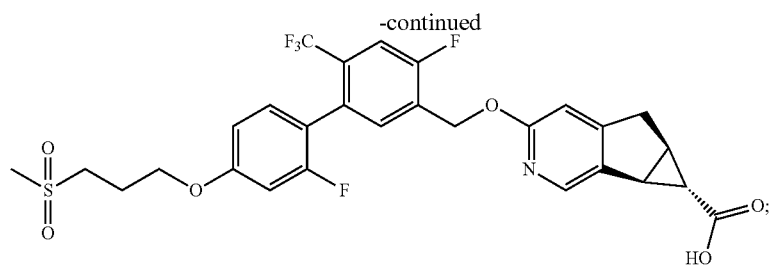
or a pharmaceutically acceptable salt thereof.
24. A compound selected from:
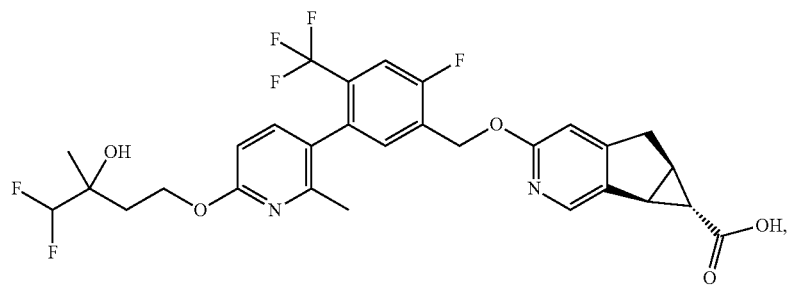
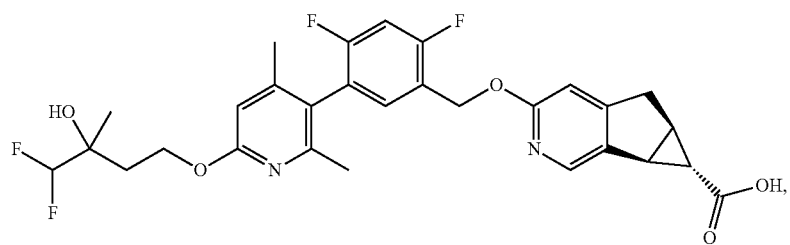
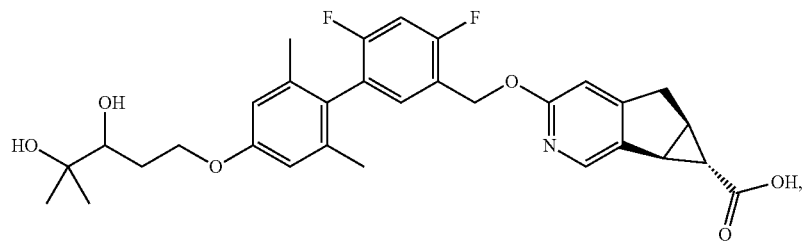
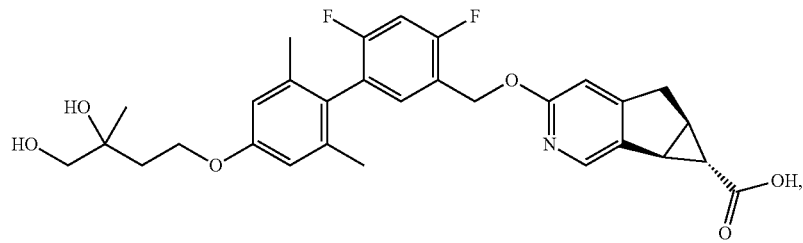
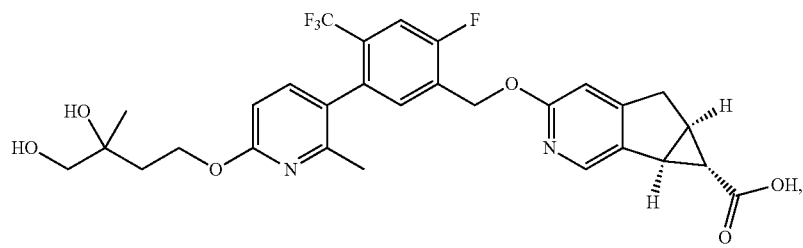

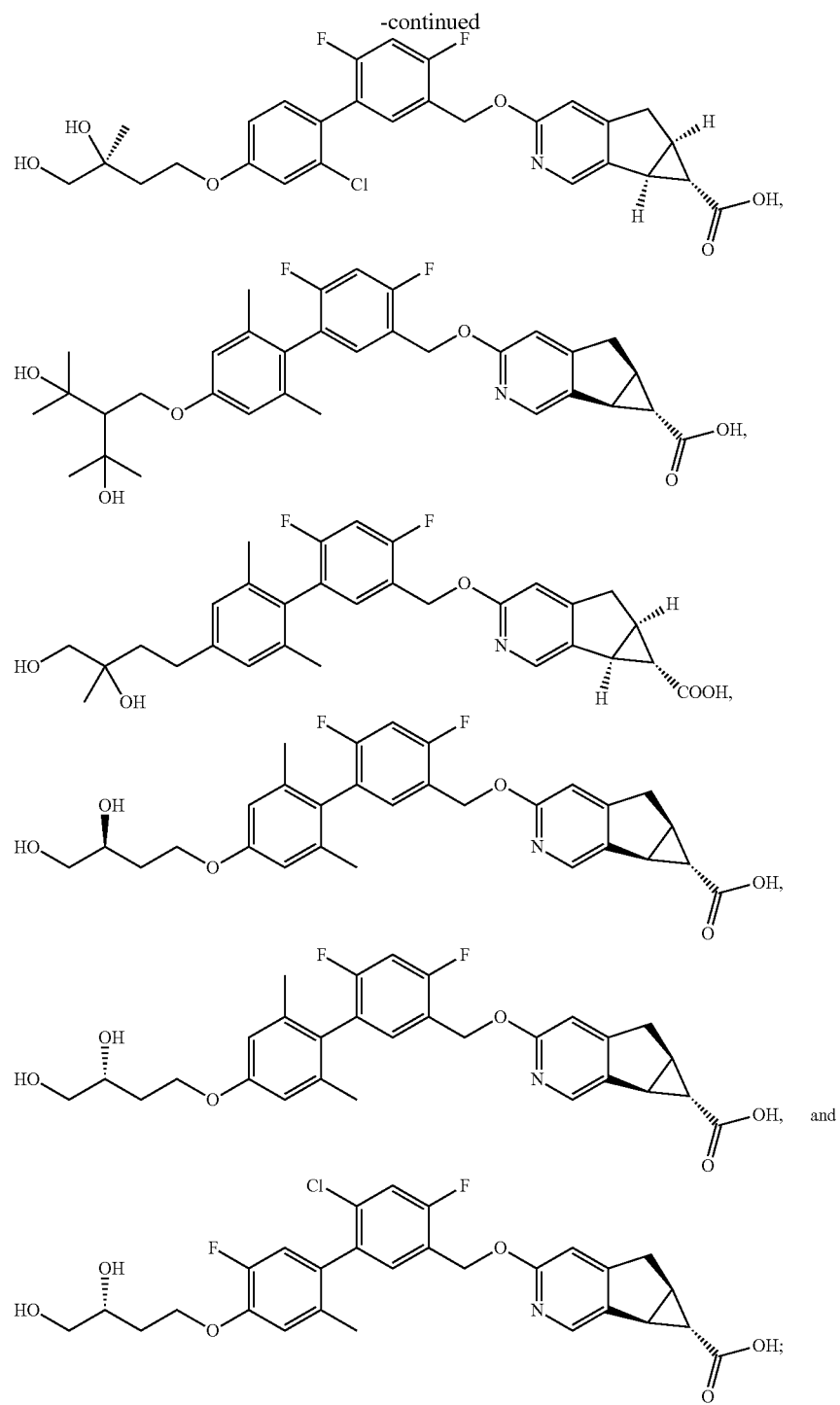
or a pharmaceutically acceptable salt thereof.
* * * * *